US007507242B2

(12) United States Patent
Triplett et al.

(10) Patent No.: US 7,507,242 B2
(45) Date of Patent: Mar. 24, 2009

(54) SURGICAL MEASUREMENT AND RESECTION FRAMEWORK

(75) Inventors: Daniel J. Triplett, Providence, UT (US);
T. Wade Fallin, Hyde Park, UT (US);
Robert W. Hoy, Paradise, UT (US);
Alan Chervitz, Palm Harbor, FL (US);
Joel Dever, Millville, UT (US)

(73) Assignee: Facet Solutions, Hopkinton, MA (US)

( * ) Notice: Subject to any disclaimer, the term of this patent is extended or adjusted under 35 U.S.C. 154(b) by 497 days.

(21) Appl. No.: 10/990,191

(22) Filed: Nov. 15, 2004

(65) Prior Publication Data

US 2005/0273167 A1  Dec. 8, 2005

Related U.S. Application Data

(63) Continuation-in-part of application No. 10/860,778, filed on Jun. 2, 2004, and a continuation-in-part of application No. 10/860,543, filed on Jun. 2, 2004, and a continuation-in-part of application No. 10/860,495, filed on Jun. 2, 2004, and a continuation-in-part of application No. 10/860,487, filed on Jun. 2, 2004.

(51) Int. Cl.
*A61F 5/00* (2006.01)
(52) U.S. Cl. .......................................... 606/87
(58) Field of Classification Search .................. 606/73, 606/90, 99, 104; 403/53–55, 63; 623/17.11–17.16; 600/594
See application file for complete search history.

(56) References Cited

U.S. PATENT DOCUMENTS 2,677,369 A    5/1954   Knowles (Continued)

FOREIGN PATENT DOCUMENTS

CN    2386790 Y    7/2000

(Continued)

OTHER PUBLICATIONS

Archus Orthopedics; *Total Facet Arthroplasty System (TFAS™)*. Website; http://www.archususa.com/Product.html.

(Continued)

*Primary Examiner*—Eduardo C Robert
*Assistant Examiner*—Nicholas Woodall
(74) *Attorney, Agent, or Firm*—David W. Meibos; Daniel F. Justin; Barbara Daniels

(57) ABSTRACT

A frame is attachable to first and second bone portions of a patient to facilitate measurement and resection of one or more bony landmarks. The frame has two anchoring features, each of which has a semispherical surface that permits rotational adjustment of the frame against the bone portions until the frame is secured. A bridging structure couples the anchoring features together such that the anchoring features are lockably movable with respect to each other. The bridging structure may have three linear sliders that provide the relative motion. A locking mechanism exerts pressure on all three sliders to lock them in place. An external anchoring feature enables attachment of the frame to a stationary reference to stabilize the frame. The frame also has registration features that permit attachment of measurement or resection tools to the frame. The frame is particularly useful for measuring and resecting spinal facets for facet replacement.

34 Claims, 48 Drawing Sheets

U.S. PATENT DOCUMENTS

| | | | |
|---|---|---|---|
| 3,247,000 A | 4/1966 | Taylor | |
| 3,298,372 A | 1/1967 | Feinberg | |
| 3,394,459 A | 7/1968 | Grant | |
| 3,426,364 A | 2/1969 | Lumb | |
| 3,486,505 A | 12/1969 | Morrison | |
| 3,508,954 A | 4/1970 | White et al. | |
| 3,648,691 A | 3/1972 | Lumb et al. | |
| 3,857,642 A | 12/1974 | Miller | |
| 3,857,643 A * | 12/1974 | Bardocz | 403/63 |
| 3,867,728 A | 2/1975 | Stubstad et al. | |
| 3,875,595 A | 4/1975 | Froning | |
| 4,003,376 A | 1/1977 | McKay et al. | |
| 4,092,078 A | 5/1978 | Klotz et al. | |
| 4,175,555 A * | 11/1979 | Herbert | 606/73 |
| 4,289,123 A | 9/1981 | Dunn | |
| 4,306,550 A | 12/1981 | Forte | |
| 4,349,921 A | 9/1982 | Kuntz | |
| 4,369,769 A | 1/1983 | Edwards | |
| 4,479,491 A | 10/1984 | Martin | |
| 4,483,334 A | 11/1984 | Murray | |
| 4,487,203 A | 12/1984 | Androphy | |
| 4,501,269 A | 2/1985 | Bagby | |
| 4,554,914 A | 11/1985 | Kapp et al. | |
| 4,567,885 A | 2/1986 | Androphy | |
| 4,567,886 A | 2/1986 | Petersen | |
| 4,574,794 A | 3/1986 | Cooke et al. | |
| 4,587,964 A | 5/1986 | Walker et al. | |
| 4,599,086 A | 7/1986 | Doty | |
| 4,604,995 A | 8/1986 | Stephens et al. | |
| 4,611,581 A | 9/1986 | Steffee | |
| 4,638,798 A | 1/1987 | Shelden et al. | |
| 4,641,636 A | 2/1987 | Cotrel | |
| 4,653,481 A | 3/1987 | Howland et al. | |
| 4,653,509 A | 3/1987 | Oloff et al. | |
| 4,657,550 A | 4/1987 | Daher | |
| 4,696,290 A | 9/1987 | Steffee | |
| 4,722,330 A | 2/1988 | Russell et al. | |
| 4,743,260 A | 5/1988 | Burton | |
| 4,759,769 A | 7/1988 | Hedman et al. | |
| 4,772,287 A | 9/1988 | Ray et al. | |
| 4,777,942 A | 10/1988 | Frey et al. | |
| 4,787,383 A | 11/1988 | Kenna | |
| 4,790,303 A | 12/1988 | Steffee | |
| 4,800,874 A | 1/1989 | David et al. | |
| 4,805,599 A | 2/1989 | Ray | |
| 4,805,602 A | 2/1989 | Puno et al. | |
| 4,827,918 A | 5/1989 | Olerud | |
| 4,843,720 A | 7/1989 | Kim | |
| 4,863,476 A | 9/1989 | Shepperd | |
| 4,863,477 A | 9/1989 | Monson | |
| 4,892,545 A | 1/1990 | Day et al. | |
| 4,893,619 A | 1/1990 | Dale et al. | |
| 4,904,260 A | 2/1990 | Ray et al. | |
| 4,911,718 A | 3/1990 | Lee et al. | |
| 4,926,849 A | 5/1990 | Downey | |
| 4,938,762 A | 7/1990 | Wehrli | |
| 4,946,458 A | 8/1990 | Harms et al. | |
| 4,952,213 A | 8/1990 | Bowman et al. | |
| 4,952,214 A | 8/1990 | Comparetto | |
| 4,953,540 A | 9/1990 | Ray et al. | |
| 4,955,908 A | 9/1990 | Frey et al. | |
| 4,957,495 A * | 9/1990 | Kluger | 606/58 |
| 5,011,484 A | 4/1991 | Breard | |
| 5,015,255 A | 5/1991 | Kuslich | |
| 5,047,032 A | 9/1991 | Jellicoe | |
| 5,047,055 A | 9/1991 | Bao et al. | |
| 5,062,845 A | 11/1991 | Kuslich et al. | |
| 5,071,437 A | 12/1991 | Steffee | |
| 5,080,662 A | 1/1992 | Paul | |
| 5,092,866 A | 3/1992 | Breard et al. | |
| 5,092,867 A | 3/1992 | Harms et al. | |
| 5,092,893 A | 3/1992 | Smith | |
| 5,112,334 A | 5/1992 | Alchermes et al. | |
| 5,116,338 A | 5/1992 | Poggie et al. | |
| 5,122,144 A | 6/1992 | Bert et al. | |
| 5,122,145 A | 6/1992 | Fishbane | |
| 5,127,912 A | 7/1992 | Ray et al. | |
| 5,129,900 A | 7/1992 | Asher et al. | |
| 5,141,512 A | 8/1992 | Farmer et al. | |
| 5,147,361 A | 9/1992 | Ojima et al. | |
| 5,147,404 A | 9/1992 | Downey | |
| 5,169,401 A | 12/1992 | Lester et al. | |
| 5,171,279 A | 12/1992 | Mathews | |
| 5,171,280 A | 12/1992 | Baumgartner | |
| 5,180,393 A | 1/1993 | Commarmond | |
| 5,192,326 A | 3/1993 | Bao et al. | |
| 5,236,460 A | 8/1993 | Barber | |
| 5,246,458 A | 9/1993 | Graham | |
| 5,258,031 A | 11/1993 | Salib et al. | |
| 5,261,910 A | 11/1993 | Warden et al. | |
| 5,263,953 A | 11/1993 | Bagby | |
| 5,282,863 A | 2/1994 | Burton | |
| 5,284,130 A | 2/1994 | Ratliff | |
| 5,291,901 A * | 3/1994 | Graf | 600/594 |
| 5,304,178 A | 4/1994 | Stahurski | |
| 5,306,275 A | 4/1994 | Bryan | |
| 5,306,308 A | 4/1994 | Gross et al. | |
| 5,306,309 A | 4/1994 | Wagner et al. | |
| 5,308,352 A | 5/1994 | Koutrouvelis | |
| 5,313,962 A | 5/1994 | Obenchain | |
| 5,318,567 A | 6/1994 | Vichard | |
| 5,360,430 A | 11/1994 | Lin | |
| 5,364,401 A | 11/1994 | Ferrante et al. | |
| 5,366,455 A | 11/1994 | Dove et al. | |
| 5,370,697 A | 12/1994 | Baumgartner | |
| 5,375,823 A | 12/1994 | Navas | |
| 5,387,213 A | 2/1995 | Breard et al. | |
| 5,391,168 A | 2/1995 | Sanders et al. | |
| 5,401,269 A | 3/1995 | Buttner-Janz et al. | |
| 5,415,661 A | 5/1995 | Holmes | |
| 5,423,828 A | 6/1995 | Benson | |
| 5,437,669 A | 8/1995 | Yuan et al. | |
| 5,437,672 A | 8/1995 | Alleyne | |
| 5,439,464 A | 8/1995 | Shapiro | |
| 5,443,516 A | 8/1995 | Albrektsson et al. | |
| 5,445,642 A | 8/1995 | McNulty et al. | |
| 5,454,816 A | 10/1995 | Ashby | |
| 5,456,722 A | 10/1995 | Mcleod et al. | |
| 5,458,641 A | 10/1995 | Ramirez Jimenez | |
| 5,458,642 A | 10/1995 | Beer et al. | |
| 5,458,643 A | 10/1995 | Oka et al. | |
| 5,464,439 A | 11/1995 | Gendler | |
| 5,470,333 A | 11/1995 | Ray | |
| 5,476,463 A | 12/1995 | Boachie-Adjei et al. | |
| 5,480,401 A | 1/1996 | Navas | |
| 5,486,178 A | 1/1996 | Hodge | |
| 5,489,308 A | 2/1996 | Kuslich et al. | |
| 5,496,318 A | 3/1996 | Howland et al. | |
| 5,507,745 A | 4/1996 | Logroscino et al. | |
| 5,507,813 A | 4/1996 | Dowd et al. | |
| 5,514,180 A | 5/1996 | Heggeness et al. | |
| 5,520,694 A | 5/1996 | Dance et al. | |
| 5,522,899 A | 6/1996 | Michelson | |
| 5,527,312 A | 6/1996 | Ray | |
| 5,531,745 A | 7/1996 | Ray | |
| 5,531,747 A | 7/1996 | Ray | |
| 5,534,028 A | 7/1996 | Bao et al. | |
| 5,534,030 A | 7/1996 | Navarro et al. | |
| 5,534,031 A | 7/1996 | Matsuzaki et al. | |
| 5,540,688 A | 7/1996 | Navas | |
| 5,540,694 A | 7/1996 | DeCarlo, Jr. et al. | |
| 5,540,696 A | 7/1996 | Booth, Jr. et al. | |
| 5,545,166 A | 8/1996 | Howland | |
| 5,545,229 A | 8/1996 | Parsons et al. | |

| | | | | | | |
|---|---|---|---|---|---|---|
| 5,549,607 | A | 8/1996 | Olson et al. | 5,860,977 A | 1/1999 | Zucherman et al. |
| 5,556,431 | A | 9/1996 | Buttner-Janz | 5,860,981 A | 1/1999 | Bertin et al. |
| 5,556,687 | A | 9/1996 | McMillin | 5,865,846 A | 2/1999 | Bryan et al. |
| 5,562,675 | A | 10/1996 | McNulty et al. | 5,868,745 A | 2/1999 | Alleyne |
| 5,562,735 | A | 10/1996 | Margulies | 5,876,404 A | 3/1999 | Zucherman et al. |
| 5,562,736 | A | 10/1996 | Ray et al. | 5,885,297 A | 3/1999 | Matsen, III |
| 5,562,737 | A | 10/1996 | Graf | 5,888,223 A | 3/1999 | Bray, Jr. |
| 5,569,248 | A | 10/1996 | Mathews | 5,893,889 A | 4/1999 | Harrington |
| 5,571,189 | A | 11/1996 | Kuslich | RE36,221 E | 6/1999 | Breard et al. |
| 5,571,191 | A | 11/1996 | Fitz | 5,911,724 A | 6/1999 | Wehrli |
| 5,572,191 | A | 11/1996 | Lundberg | 5,916,219 A | 6/1999 | Matsuno et al. |
| 5,578,037 | A | 11/1996 | Sanders et al. | 5,916,221 A | 6/1999 | Hodorek et al. |
| 5,582,612 | A | 12/1996 | Lin | 5,916,267 A | 6/1999 | Tienboon |
| 5,584,832 | A | 12/1996 | Schlapfer | 5,919,195 A | 7/1999 | Wilson et al. |
| 5,598,269 | A | 1/1997 | Kitaevich et al. | 5,925,049 A | 7/1999 | Gustilo et al. |
| 5,601,563 | A | 2/1997 | Burke et al. | 5,928,139 A * | 7/1999 | Koros et al. ................. 600/205 |
| 5,603,713 | A | 2/1997 | Aust et al. | 5,938,665 A | 8/1999 | Martin |
| 5,609,634 | A | 3/1997 | Voydeville | 5,951,555 A | 9/1999 | Rehak et al. |
| 5,611,353 | A | 3/1997 | Dance et al. | 5,961,516 A | 10/1999 | Graf |
| 5,616,146 | A | 4/1997 | Murray | 5,986,169 A | 11/1999 | Gjunter |
| 5,616,147 | A | 4/1997 | Gadelius | 5,989,261 A | 11/1999 | Walker et al. |
| 5,645,597 | A | 7/1997 | Krapiva | 5,997,543 A | 12/1999 | Truscott |
| 5,645,599 | A | 7/1997 | Samani | 6,001,130 A | 12/1999 | Bryan et al. |
| 5,649,926 | A | 7/1997 | Howland | 6,004,322 A | 12/1999 | Bernstein |
| 5,649,928 | A | 7/1997 | Grundei | 6,014,588 A | 1/2000 | Fitz |
| 5,653,762 | A | 8/1997 | Pisharodi | 6,019,759 A | 2/2000 | Rogozinski |
| 5,662,656 | A | 9/1997 | White | 6,019,792 A | 2/2000 | Cauthen |
| 5,665,095 | A | 9/1997 | Jacobson | 6,024,746 A | 2/2000 | Katz |
| 5,666,243 | A | 9/1997 | Brent | 6,039,761 A | 3/2000 | Li et al. |
| 5,672,175 | A | 9/1997 | Martin | 6,039,763 A | 3/2000 | Shelokov |
| 5,674,223 | A | 10/1997 | Cipolletti | 6,048,342 A | 4/2000 | Zucherman et al. |
| 5,674,295 | A | 10/1997 | Ray et al. | 6,063,088 A | 5/2000 | Winslow |
| 5,674,296 | A | 10/1997 | Bryan | 6,063,121 A | 5/2000 | Xavier et al. |
| 5,676,701 | A | 10/1997 | Yuan et al. | 6,066,325 A | 5/2000 | Wallace et al. |
| 5,681,310 | A | 10/1997 | Yuan et al. | 6,068,630 A | 5/2000 | Zucherman et al. |
| 5,681,320 | A | 10/1997 | McGuire | RE36,758 E | 6/2000 | Fitz |
| 5,683,464 | A | 11/1997 | Wagner et al. | 6,074,390 A | 6/2000 | Zucherman et al. |
| 5,683,465 | A | 11/1997 | Shinn et al. | 6,080,157 A | 6/2000 | Cathro et al. |
| 5,688,272 | A | 11/1997 | Montague et al. | 6,090,112 A | 7/2000 | Zucherman et al. |
| 5,688,279 | A | 11/1997 | McNulty et al. | 6,090,114 A | 7/2000 | Matsuno et al. |
| 5,688,280 | A | 11/1997 | Booth, Jr. et al. | 6,093,205 A | 7/2000 | McLeod et al. |
| 5,690,629 | A | 11/1997 | Asher et al. | 6,096,082 A | 8/2000 | Stegmuller et al. |
| 5,700,268 | A | 12/1997 | Bertin | 6,106,529 A | 8/2000 | Techiera |
| 5,702,392 | A | 12/1997 | Wu et al. | 6,113,637 A | 9/2000 | Gill et al. |
| 5,702,450 | A | 12/1997 | Bisserie | 6,113,639 A | 9/2000 | Ray et al. |
| 5,702,453 | A | 12/1997 | Rabbe et al. | 6,120,507 A | 9/2000 | Allard et al. |
| 5,704,936 | A | 1/1998 | Mazel | 6,120,510 A | 9/2000 | Albrektsson et al. |
| 5,713,900 | A | 2/1998 | Benzel et al. | 6,132,464 A * | 10/2000 | Martin .................... 623/17.15 |
| 5,716,415 | A | 2/1998 | Steffee | 6,132,465 A | 10/2000 | Ray et al. |
| 5,725,582 | A | 3/1998 | Bevan et al. | 6,146,421 A | 11/2000 | Gordon et al. |
| 5,728,097 | A | 3/1998 | Mathews | 6,149,652 A | 11/2000 | Zucherman et al. |
| 5,735,899 | A | 4/1998 | Schwartz et al. | 6,151,934 A | 11/2000 | Chong et al. |
| 5,741,264 | A | 4/1998 | Cipolletti | 6,152,926 A | 11/2000 | Zucherman et al. |
| 5,743,915 | A | 4/1998 | Bertin et al. | 6,156,038 A | 12/2000 | Zucherman et al. |
| 5,746,743 | A | 5/1998 | Greenberg | 6,156,067 A | 12/2000 | Bryan et al. |
| 5,749,873 | A | 5/1998 | Fairley | 6,159,216 A | 12/2000 | Burkinshaw et al. |
| 5,755,796 | A | 5/1998 | Ibo et al. | 6,174,314 B1 | 1/2001 | Waddell |
| 5,769,854 | A | 6/1998 | Bastian et al. | 6,176,861 B1 | 1/2001 | Bernstein et al. |
| 5,769,855 | A | 6/1998 | Bertin et al. | 6,179,838 B1 | 1/2001 | Fiz |
| 5,772,661 | A | 6/1998 | Michelson | 6,183,471 B1 | 2/2001 | Zucherman et al. |
| 5,776,137 | A | 7/1998 | Katz | 6,190,387 B1 | 2/2001 | Zucherman et al. |
| 5,779,710 | A | 7/1998 | Matsen, III | 6,190,414 B1 | 2/2001 | Young et al. |
| 5,797,909 | A | 8/1998 | Michelson | 6,193,724 B1 | 2/2001 | Chan |
| 5,810,829 | A | 9/1998 | Elliott et al. | 6,206,882 B1 | 3/2001 | Cohen |
| 5,810,830 | A | 9/1998 | Noble et al. | 6,206,922 B1 | 3/2001 | Zdeblick et al. |
| 5,814,046 | A | 9/1998 | Hopf | 6,221,082 B1 | 4/2001 | Marino et al. |
| 5,814,050 | A | 9/1998 | Benson | 6,228,090 B1 | 5/2001 | Waddell |
| 5,817,097 | A | 10/1998 | Howard et al. | 6,228,118 B1 | 5/2001 | Gordon |
| 5,824,093 | A | 10/1998 | Ray et al. | 6,235,030 B1 | 5/2001 | Zucherman et al. |
| 5,824,094 | A | 10/1998 | Serhan et al. | 6,238,397 B1 | 5/2001 | Zucherman et al. |
| 5,830,216 | A | 11/1998 | Insall et al. | 6,241,730 B1 | 6/2001 | Alby |
| 5,836,948 | A | 11/1998 | Zucherman et al. | 6,258,095 B1 | 7/2001 | Lombardo et al. |
| 5,853,415 | A | 12/1998 | Bertin et al. | 6,264,655 B1 | 7/2001 | Pisharodi |

| | | | | | | |
|---|---|---|---|---|---|---|
| 6,267,764 B1 | 7/2001 | Elberg | | 6,835,205 B2 | 12/2004 | Atkinson et al. |
| 6,280,444 B1 | 8/2001 | Zucherman et al. | | 6,835,207 B2 | 12/2004 | Zacouto et al. |
| 6,290,700 B1 | 9/2001 | Schmotzer | | 7,087,084 B2 | 8/2006 | Reiley |
| 6,290,704 B1 | 9/2001 | Burkinshaw et al. | | 2001/0007073 A1 | 7/2001 | Zucherman et al. |
| 6,293,949 B1 | 9/2001 | Justis et al. | | 2001/0012938 A1 | 8/2001 | Zucherman et al. |
| 6,302,890 B1 | 10/2001 | Leone, Jr. | | 2001/0016743 A1 | 8/2001 | Zucherman et al. |
| 6,312,469 B1 | 11/2001 | Gielen et al. | | 2001/0021850 A1 | 9/2001 | Zucherman et al. |
| 6,314,325 B1 | 11/2001 | Fitz | | 2001/0031965 A1 | 10/2001 | Zucherman et al. |
| 6,332,882 B1 | 12/2001 | Zucherman et al. | | 2001/0039452 A1 | 11/2001 | Zucherman et al. |
| 6,332,883 B1 | 12/2001 | Zucherman et al. | | 2002/0010474 A1 | 1/2002 | Chan |
| 6,344,043 B1 | 2/2002 | Pappas | | 2002/0029039 A1 | 3/2002 | Zucherman et al. |
| 6,379,355 B1 | 4/2002 | Zucherman et al. | | 2002/0065557 A1 | 5/2002 | Goble et al. |
| 6,395,005 B1 | 5/2002 | Lovell | | 2002/0072800 A1 | 6/2002 | Goble et al. |
| 6,402,750 B1 | 6/2002 | Atkinson et al. | | 2002/0091446 A1 | 7/2002 | Zucherman et al. |
| 6,413,259 B1 | 7/2002 | Lyons et al. | | 2002/0099384 A1 | 7/2002 | Scribner et al. |
| 6,419,676 B1 | 7/2002 | Zucherman et al. | | 2002/0116000 A1 | 8/2002 | Zucherman et al. |
| 6,419,677 B2 | 7/2002 | Zucherman et al. | | 2002/0123806 A1 | 9/2002 | Reiley |
| 6,419,703 B1 | 7/2002 | Fallin et al. | | 2002/0143331 A1 | 10/2002 | Zucherman et al. |
| 6,419,704 B1 | 7/2002 | Ferree | | 2002/0151895 A1 | 10/2002 | Soboleski et al. |
| 6,440,169 B1 | 8/2002 | Elberg et al. | | 2002/0165552 A1 | 11/2002 | Duffner |
| 6,447,546 B1 | 9/2002 | Bramlet et al. | | 2002/0183746 A1 | 12/2002 | Zucherman et al. |
| 6,451,019 B1 | 9/2002 | Zucherman et al. | | 2003/0004572 A1 | 1/2003 | Goble et al. |
| 6,451,020 B1 | 9/2002 | Zucherman et al. | | 2003/0009226 A1 | 1/2003 | Graf |
| 6,458,131 B1 | 10/2002 | Ray | | 2003/0028250 A1 | 2/2003 | Reiley et al. |
| 6,458,135 B1 | 10/2002 | Harwin et al. | | 2003/0040797 A1 | 2/2003 | Fallin et al. |
| 6,461,359 B1 | 10/2002 | Tribus et al. | | 2003/0055427 A1 | 3/2003 | Graf |
| 6,471,704 B2 | 10/2002 | Gertzbein et al. | | 2003/0065330 A1 | 4/2003 | Zucherman et al. |
| 6,475,219 B1 | 11/2002 | Shelokov | | 2003/0073998 A1 | 4/2003 | Pagliuca et al. |
| 6,478,796 B2 | 11/2002 | Zucherman et al. | | 2003/0074005 A1 | 4/2003 | Roth et al. |
| 6,481,440 B2 | 11/2002 | Gielen et al. | | 2003/0093080 A1 | 5/2003 | Brown et al. |
| 6,485,518 B1 | 11/2002 | Cornwall et al. | | 2003/0109880 A1 | 6/2003 | Shirado et al. |
| 6,500,178 B2 | 12/2002 | Zucherman et al. | | 2003/0130665 A1 | 7/2003 | Pinczewski et al. |
| 6,503,255 B1 | 1/2003 | Albrektsson et al. | | 2003/0153912 A1 | 8/2003 | Graf |
| 6,514,239 B2 * | 2/2003 | Shimmura et al. ............. 606/1 | | 2003/0187451 A1 | 10/2003 | Ball et al. |
| 6,514,256 B2 | 2/2003 | Zucherman et al. | | 2003/0187452 A1 | 10/2003 | Smith et al. |
| 6,514,259 B2 | 2/2003 | Picard et al. | | 2003/0191470 A1 | 10/2003 | Ritland |
| 6,527,806 B2 | 3/2003 | Ralph et al. | | 2003/0212403 A1 | 11/2003 | Swanson |
| 6,540,747 B1 | 4/2003 | Marino | | 2003/0220642 A1 | 11/2003 | Freudiger |
| 6,540,785 B1 | 4/2003 | Gill et al. | | 2003/0220643 A1 | 11/2003 | Ferree |
| 6,565,605 B2 | 5/2003 | Goble et al. | | 2003/0236524 A1 | 12/2003 | Squires et al. |
| 6,579,319 B2 | 6/2003 | Goble et al. | | 2004/0006341 A1 | 1/2004 | Shaolian et al. |
| 6,582,433 B2 | 6/2003 | Yun | | 2004/0006391 A1 | 1/2004 | Reiley |
| 6,585,769 B1 | 7/2003 | Muhanna et al. | | 2004/0009232 A1 | 1/2004 | Reiner |
| 6,595,997 B2 | 7/2003 | Axelson, Jr. | | 2004/0015173 A1 | 1/2004 | Irving |
| 6,610,091 B1 | 8/2003 | Reiley | | 2004/0024458 A1 | 2/2004 | Senegas et al. |
| 6,613,052 B1 | 9/2003 | Kinnett | | 2004/0049189 A1 | 3/2004 | Le Couedic et al. |
| 6,616,669 B2 | 9/2003 | Ogilvie et al. | | 2004/0049190 A1 | 3/2004 | Biedermann et al. |
| 6,623,488 B1 | 9/2003 | Leone, Jr. | | 2004/0049272 A1 | 3/2004 | Reiley |
| 6,626,909 B2 | 9/2003 | Chin | | 2004/0049273 A1 | 3/2004 | Reiley |
| 6,626,944 B1 | 9/2003 | Taylor | | 2004/0049274 A1 | 3/2004 | Reiley |
| 6,632,226 B2 | 10/2003 | Chan | | 2004/0049275 A1 | 3/2004 | Reiley |
| 6,635,061 B1 | 10/2003 | Snyder | | 2004/0049276 A1 | 3/2004 | Reiley |
| 6,645,214 B2 | 11/2003 | Brown et al. | | 2004/0049277 A1 | 3/2004 | Reiley |
| 6,648,891 B2 * | 11/2003 | Kim .......................... 606/69 | | 2004/0049278 A1 | 3/2004 | Reiley |
| 6,652,527 B2 | 11/2003 | Zucherman et al. | | 2004/0049281 A1 | 3/2004 | Reiley |
| 6,652,534 B2 | 11/2003 | Zucherman et al. | | 2004/0073215 A1 | 4/2004 | Carli |
| 6,652,585 B2 | 11/2003 | Lange | | 2004/0078042 A1 | 4/2004 | Masini |
| 6,660,041 B1 | 12/2003 | Grundei | | 2004/0078082 A1 | 4/2004 | Lange |
| 6,669,698 B1 * | 12/2003 | Tromanhauser et al. ....... 606/61 | | 2004/0082954 A1 | 4/2004 | Teitelbaum et al. |
| 6,669,729 B2 | 12/2003 | Chin | | 2004/0087950 A1 | 5/2004 | Teitelbaum |
| 6,673,077 B1 | 1/2004 | Katz | | 2004/0087960 A1 | 5/2004 | Kinnett |
| 6,695,842 B2 | 2/2004 | Zucherman et al. | | 2004/0097951 A1 | 5/2004 | Steffensmeier |
| 6,699,246 B2 | 3/2004 | Zucherman et al. | | 2004/0098131 A1 | 5/2004 | Bryan |
| 6,699,247 B2 | 3/2004 | Zucherman et al. | | 2004/0106995 A1 | 6/2004 | Le Couedic et al. |
| 6,702,824 B2 | 3/2004 | Maroney et al. | | 2004/0111154 A1 | 6/2004 | Reiley |
| 6,733,534 B2 | 5/2004 | Sherman | | 2004/0116927 A1 | 6/2004 | Graf |
| 6,740,087 B2 | 5/2004 | Knox | | 2004/0117017 A1 | 6/2004 | Pasquet et al. |
| 6,761,719 B2 | 7/2004 | Justis et al. | | 2004/0122439 A1 | 6/2004 | Dwyer et al. |
| 6,761,720 B1 | 7/2004 | Senegas | | 2004/0127989 A1 | 7/2004 | Dooris et al. |
| 6,783,527 B2 | 8/2004 | Drewry et al. | | 2004/0143264 A1 | 7/2004 | Mcafee |
| 6,796,983 B1 | 9/2004 | Zucherman et al. | | 2004/0147928 A1 | 7/2004 | Landry et al. |
| 6,796,986 B2 | 9/2004 | Duffner | | 2004/0153071 A1 | 8/2004 | Zucherman et al. |
| 6,811,567 B2 | 11/2004 | Reiley | | 2004/0153086 A1 | 8/2004 | Sanford |

| Publication No. | Date | Name | | Country | Number | Date |
|---|---|---|---|---|---|---|
| 2004/0158245 A1 | 8/2004 | Chin | | SU | 1517953 A1 | 10/1989 |
| 2004/0167520 A1 | 8/2004 | Zucherman et al. | | SU | 1547813 | 3/1990 |
| 2004/0172025 A1 | 9/2004 | Drewry et al. | | WO | WO8707827 A1 | 12/1987 |
| 2004/0181282 A1 | 9/2004 | Zucherman et al. | | WO | WO9414366 A2 | 7/1994 |
| 2004/0181285 A1 | 9/2004 | Simonson | | WO | WO9421185 A1 | 9/1994 |
| 2004/0186475 A1 | 9/2004 | Falahee | | WO | WO9505783 A1 | 3/1995 |
| 2004/0204718 A1* | 10/2004 | Hoffman ................. 606/108 | | WO | WO9505784 A1 | 3/1995 |
| 2004/0220568 A1 | 11/2004 | Zucherman et al. | | WO | WO9505785 A1 | 3/1995 |
| 2004/0225289 A1 | 11/2004 | Biedermann et al. | | WO | WO9505786 A1 | 3/1995 |
| 2004/0230192 A1 | 11/2004 | Graf | | WO | WO9600049 A1 | 1/1996 |
| 2004/0230201 A1 | 11/2004 | Yuan et al. | | WO | WO9721389 A1 | 6/1997 |
| 2004/0230304 A1 | 11/2004 | Yuan | | WO | WO9729695 A1 | 8/1997 |
| 2004/0236327 A1 | 11/2004 | Paul et al. | | WO | WO9730641 A1 | 8/1997 |
| 2004/0236328 A1 | 11/2004 | Paul et al. | | WO | WO9730648 A1 | 8/1997 |
| 2004/0236329 A1 | 11/2004 | Panjabi | | WO | WO9822033 A1 | 5/1998 |
| 2004/0243239 A1 | 12/2004 | Taylor | | WO | WO9832384 A1 | 7/1998 |
| 2005/0010291 A1 | 1/2005 | Stinson et al. | | WO | WO9848707 A1 | 11/1998 |
| 2005/0010293 A1 | 1/2005 | Zucherman et al. | | WO | WO9848717 A1 | 11/1998 |
| 2005/0010298 A1 | 1/2005 | Zucherman et al. | | WO | WO9856301 A1 | 12/1998 |
| 2005/0027361 A1 | 2/2005 | Reiley | | WO | WO9905995 A1 | 2/1999 |
| 2005/0033434 A1 | 2/2005 | Berry | | WO | WO9921500 A1 | 5/1999 |
| 2005/0033439 A1 | 2/2005 | Gordon et al. | | WO | WO9921501 A1 | 5/1999 |
| 2005/0043797 A1 | 2/2005 | Lee | | WO | WO9923863 A1 | 5/1999 |
| 2005/0043799 A1 | 2/2005 | Reiley | | WO | WO9925263 A1 | 5/1999 |
| 2005/0113927 A1 | 5/2005 | Malek | | WO | WO9940864 A1 | 8/1999 |
| 2005/0119748 A1 | 6/2005 | Reiley et al. | | WO | WO9960957 C2 | 12/1999 |
| 2005/0131406 A1 | 6/2005 | Reiley et al. | | WO | WO9965412 A1 | 12/1999 |
| 2005/0137705 A1 | 6/2005 | Reiley | | WO | WO0035359 A1 | 6/2000 |
| 2005/0137706 A1 | 6/2005 | Reiley | | WO | WO0038582 | 7/2000 |
| 2005/0143818 A1 | 6/2005 | Yuan et al. | | WO | WO0045715 A1 | 8/2000 |
| 2005/0149190 A1 | 7/2005 | Reiley | | WO | WO0062684 A1 | 10/2000 |
| 2005/0154467 A1 | 7/2005 | Peterman et al. | | WO | WO0100096 A1 | 1/2001 |
| 2005/0171609 A1 | 8/2005 | Humphreys | | WO | WO0130247 A1 | 5/2001 |
| 2005/0203532 A1* | 9/2005 | Ferguson et al. .......... 606/90 | | WO | WO0130248 A1 | 5/2001 |
| 2005/0203533 A1* | 9/2005 | Ferguson et al. .......... 606/90 | | WO | WO0145576 A1 | 6/2001 |
| 2006/0100634 A1* | 5/2006 | Ferguson ................ 606/90 | | WO | WO0149192 A1 | 7/2001 |
| 2006/0195114 A1* | 8/2006 | Bertagnoli .............. 606/90 | | WO | WO0156489 A1 | 8/2001 |
| | | | | WO | WO0164142 A1 | 9/2001 |
| FOREIGN PATENT DOCUMENTS | | | | WO | WO0164144 A2 | 9/2001 |
| DE | 10134505 A1 * | 1/2003 | | WO | WO0191657 A1 | 12/2001 |
| EP | 263292 A1 | 4/1988 | | WO | WO0191658 A1 | 12/2001 |
| EP | 275375 A1 | 7/1988 | | WO | WO0197721 A2 | 12/2001 |
| EP | 322363 A1 | 6/1989 | | WO | WO0197721 A3 | 12/2001 |
| EP | 408489 A1 | 1/1991 | | WO | WO0200124 A1 | 1/2002 |
| EP | 322334 B1 | 2/1992 | | WO | WO0203882 A2 | 1/2002 |
| EP | 661023 A2 | 7/1995 | | WO | WO0207621 A1 | 1/2002 |
| EP | 667127 A1 | 8/1995 | | WO | WO0207622 A1 | 1/2002 |
| EP | 502738 B1 | 11/1995 | | WO | WO0207623 A1 | 1/2002 |
| EP | 709062 A1 | 5/1996 | | WO | WO0211633 A2 | 2/2002 |
| EP | 720834 A2 | 7/1996 | | WO | WO0213732 A3 | 2/2002 |
| EP | 842639 A2 | 5/1998 | | WO | WO0230336 A2 | 4/2002 |
| EP | 555003 B1 | 11/1998 | | WO | WO0234120 A2 | 5/2002 |
| EP | 767637 B1 | 11/1998 | | WO | WO0243603 A1 | 6/2002 |
| EP | 768843 B1 | 2/1999 | | WO | WO02067792 A2 | 9/2002 |
| EP | 669109 B1 | 5/1999 | | WO | WO02067793 A2 | 9/2002 |
| EP | 923906 A2 | 6/1999 | | WO | WO02089712 A1 | 11/2002 |
| EP | 931513 A2 | 7/1999 | | WO | WO02089712 A2 | 11/2002 |
| EP | 962190 A2 | 12/1999 | | WO | WO02102259 A2 | 12/2002 |
| EP | 1025820 A2 | 8/2000 | | WO | WO03009737 A1 | 2/2003 |
| EP | 1356775 A2 | 10/2003 | | WO | WO03011147 A1 | 2/2003 |
| EP | 1442712 A1 | 8/2004 | | WO | WO03015646 A2 | 2/2003 |
| EP | 1239785 B1 | 9/2004 | | WO | WO03045262 A2 | 6/2003 |
| EP | 1343424 B1 | 9/2004 | | WO | WO03051211 A1 | 6/2003 |
| EP | 1399078 B1 | 12/2004 | | WO | WO03075740 A2 | 9/2003 |
| FR | 2721501 B1 | 8/1996 | | WO | WO03077806 A2 | 9/2003 |
| GB | 2322304 A | 8/1998 | | WO | WO2004017817 A2 | 3/2004 |
| JP | 1119244 A2 | 5/1989 | | WO | WO2004019762 A2 | 3/2004 |
| JP | 10179622 A2 | 7/1998 | | WO | WO2004024010 A1 | 3/2004 |
| JP | 10277070 A2 | 10/1998 | | WO | WO2004032794 A2 | 4/2004 |
| JP | 23339727 A2 | 12/2003 | | WO | WO2004032794 A3 | 4/2004 |
| SU | 1454428 A1 | 1/1989 | | WO | WO2004039239 A2 | 5/2004 |
| SU | 1468543 A1 | 3/1989 | | WO | WO2004039239 A3 | 5/2004 |
| | | | | WO | WO2004039243 A2 | 5/2004 |

| | | | |
|---|---|---|---|
| WO | WO2004039243 A3 | 5/2004 |
| WO | WO2004041066 A2 | 5/2004 |
| WO | WO2004041066 A3 | 5/2004 |
| WO | WO2004073533 A1 | 9/2004 |
| WO | WO2004098423 A1 | 11/2004 |
| WO | WO2004098452 A2 | 11/2004 |
| WO | WO2004105577 A2 | 12/2004 |
| WO | WO2004105580 A2 | 12/2004 |
| WO | WO2005013864 | 2/2005 |
| WO | WO2005037149 | 4/2005 |
| WO | WO2005044152 A1 | 5/2005 |
| WO | WO2006102443 | 9/2006 |

OTHER PUBLICATIONS

Todd Anres; *Facet Joint Arthroplasty: A Glimpse of the Future of Spine Technology*, Othopaedic Product News, Sep./Oct. 2005 p. 38,40.

Impliant ; *Posterior Fixation Website*; www.impliant.com, Jul. 14, 2006.

Shaw, M; Development of Artifical Facets—Biomechanical Perspective *51st Annual Metting of the Orthopaedic Research Society, Poster No. 1263*, Feb. 20, 2005.

Goh JC, et al., "Influence of PLIF cage size on lumbar spine stability", Spine, Jan. 2000 25:1, PubMed abstract.

Head WC, Wagner surface replacement arthroplasty of the hip. Analysis of fourteen failures in forty-one hips:, J Bone Joint Surg. [Am], Mar. 1981 63:3, PubMed Abstract.

Kotani Y, et al., "The effects of spinal fixation and destabilization on the biomechanical and histologic properties of spinal ligaments. An in vivo study.", Spine, Mar. 15, 1998 23:6, PubMed abstract.

Lemaire JP, et al., "Intervertebral Disc Prosthesis: Results and Prospects for the Year 2000", Clinical Orthopaedics and Related Research, PubMed abstract.

Nagata H, et al., "The effects of immobilization of long segments of the spine on the adjacent and distal facet force and lumbrosacral motion", Spine, Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compressive strength of posterior lumbar interbody fusion implants", Spine, Aug 1, 2000 25:15, PubMed abstract.

\* cited by examiner

SURGICAL MEASUREMENT AND RESECTION FRAMEWORK

CROSS-REFERENCE TO RELATED APPLICATIONS

This application is a continuation-in-part of U.S. patent application Ser. No. 10/860,778, filed on Jun. 2, 2004 and entitled SPINAL FACET IMPLANT WITH SPHERICAL IMPLANT APPOSITION SURFACE AND BONE BED AND METHODS OF USE, a continuation-in-part of U.S. patent application Ser. No. 10/860,543, filed on Jun. 2, 2004 and entitled SPINAL FACET IMPLANTS WITH MATING ARTICULATING BEARING SURFACE AND METHODS OF USE, a continuation-in-part of U.S. patent application Ser. No. 10/860,495, filed on Jun. 2, 2004 and entitled LINKED BILATERAL SPINAL FACET IMPLANTS AND METHODS OF USE, and a continuation-in-part of U.S. patent application Ser. No. 10/860,487, filed on Jun. 2, 2004 and entitled SPINAL FACET JOINT IMPLANT, the disclosures of which are incorporated herein by reference.

BACKGROUND OF THE INVENTION

1. The Field of the Invention

The present invention relates generally to systems and methods for measuring and/or resecting bone, and more particularly, to systems and methods for measuring and resecting spinal facets for replacement with facet prostheses.

2. The Relevant Technology

Many people experience back pain. Back pain is not only uncomfortable, but can be particularly debilitating. Many people who wish to participate in sports, manual labor, or even sedentary employment are unable to do so because of pains that arise from motion of or pressure on the spinal column. Such pains are often caused by traumatic, inflammatory, metabolic, synovial, neoplastic and degenerative disorders of the spine.

One of the most common surgical interventions today is arthrodesis, or spine fusion, of one or more motion segments, with approximately 300,000 procedures performed annually in the United States. Clinical success varies considerably, depending upon technique and indications, and consideration must be given to the concomitant risks and complications. For example, spine fusion may decrease function by limiting the range of motion for patients in flexion, extension, rotation, and lateral bending. Furthermore, spine fusion may create increased stresses and, therefore, accelerated degeneration of adjacent non-fused motion segments. Additionally, pseudoarthrosis, as a result of an incomplete or ineffective fusion, may reduce or even eliminate pain relief for the patient. Finally, the fusion device, whether artificial or biological, may migrate out of the fusion site.

Recently, several attempts have been made to recreate the natural biomechanics of the spine by use of an artificial disc. Artificial discs provide for articulation between vertebral bodies to recreate the full range of motion allowed by the elastic properties of the natural intervertebral disc which directly connects two opposed vertebral bodies. However, artificial discs do not fully address the mechanics of motion of the spinal column.

In addition to the intervertebral disc, posterior elements called the facet joints help to support axial, torsional and shear loads that act on the spinal column. The facet joints are diarthroidal joints that provide both sliding articulation and load transmission features. The facet joints also help to maintain the appropriate level of stiffness in the spinal column in all planes of motion, including flexion and extension, lateral bending, and rotation.

Recently, some procedures for replacing facet joints have been proposed. Unfortunately, spinal anatomy is very complex and highly variable from one person to another. Accordingly, making accurate spinal measurements and resections can be very difficult. Spinal resection is made even more difficult by the need to avoid nerve roots positioned in close proximity to the bony features that are to be resected. Facet joint replacement adds additional difficulties because the facet joints articulate to provide three distinct planes of motion. Accordingly, replacement of the facet joints requires that each plane of motion be reproduced in order to accurately preserve the natural biomechanics of the spine. Hence, a need exists for systems and methods that facilitate accurate measurement and resection of spinal bone tissue.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to more accurately measure and resect structural tissue, and more particularly, spinal bone tissue. The present invention can be used to facilitate facet joint replacement, thereby alleviating back pain resulting from traumatic, inflammatory, metabolic, synovial, neoplastic and degenerative spinal disorders. The configuration and operation of at least one embodiment of the invention will be shown and described in greater detail with reference to FIGS. 1 through 48, as follows.

In this application, "registration" refers to a process by which one object is coupled to another in such a manner that translation and/or rotation of the second object is limited relative to the first object, so that the first object serves as a reference frame for motion or operation of the second object. "Coupling" refers to direct contact between two objects or indirect contact (i.e., contact via a third object) by which relative motion between the first two objects is limited. Two objects that are integrally formed with each other may also be said to be "coupled" together (i.e., via integral formation).

A "registration feature" is any part of a first object that can be used as a coupling point for registration of a second object with respect to the first object. A "registration interface" is any part of a second object that can be used to register the second object to a first object. "Attachment" refers to a form of coupling in which a first object is restricted from translating or rotating away from a second object. "Connecting" does not require restriction of relative motion between two objects; any form of direct or indirect contact is sufficient.

"Semispherical" does not require a half sphere; rather, any shape with a surface that replicates any portion of the surface of a sphere may be termed "semispherical." A "bony landmark" is a pre-established portion of a bone having a recognizable shape. A "pivot feature" is any pivotable joint or rounded surface that provides generally rotary motion with respect to an object such as a bone. "Rotation" does not require full-circle motion; indeed, oscillatory pivotal motion is one form of rotation. A "displacement" refers to a linear or angular separation between two objects, or mathematical entities. An "axis" of an object is generally an axis of symmetry, or where the object is not symmetrical, may be a direction along which the length of the object is oriented.

A "cutting tool" is a tool designed to remove a portion of an object, such as a bone. A "resection tool" need not actually have an implement for cutting, but may simply be a guide for a cutting tool. A "guide feature" is any feature capable of guiding an object such as a cutting blade; accordingly, a guide feature may be a slot, hole, surface having a shape that provides a pre-established guide pattern, or the like.

Figure 1:
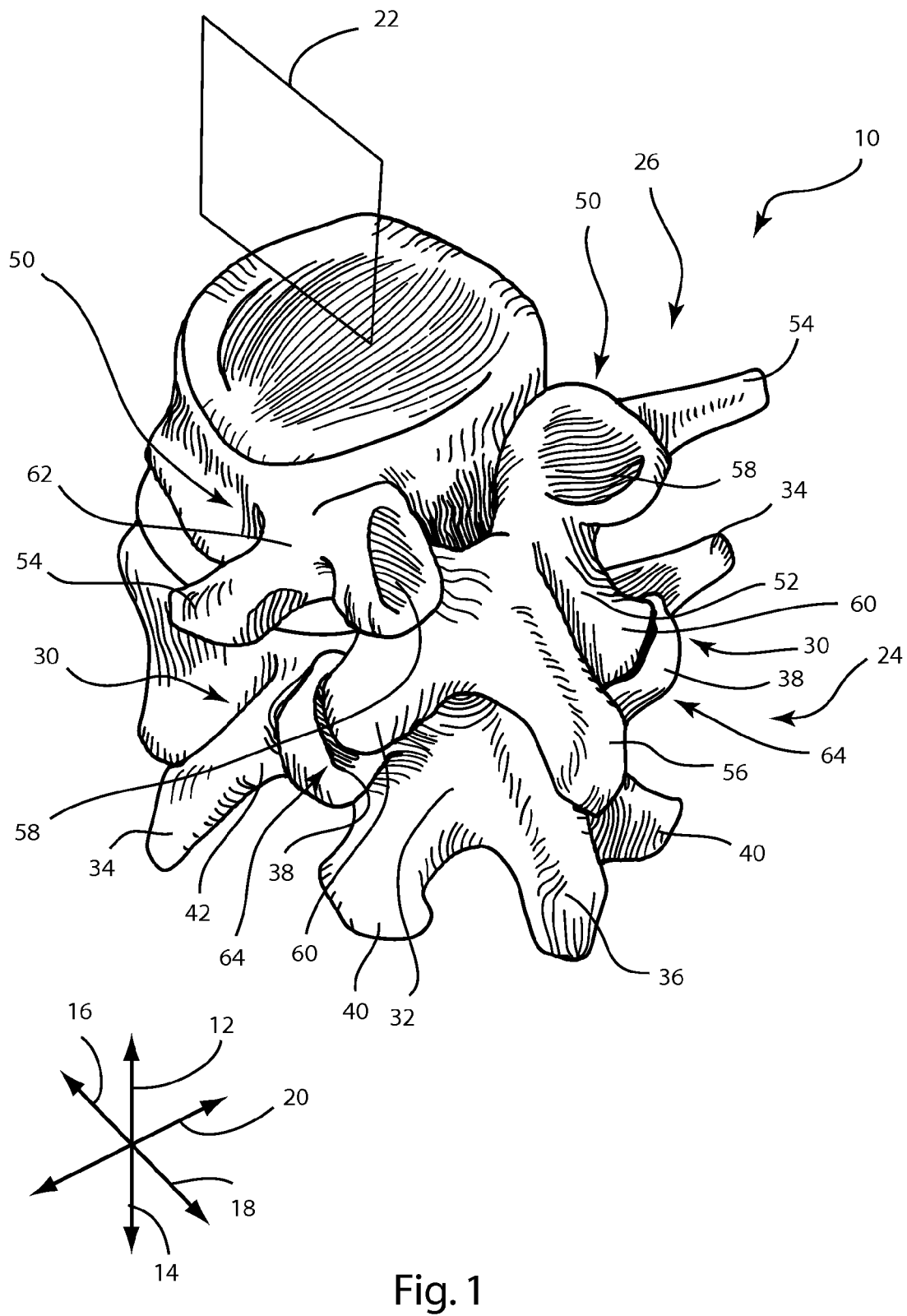
FIG. 1 is a perspective view of the L4 and L5 vertebrae of a spinal column.

Referring to FIG. 1, a perspective view illustrates a portion of a spine 10. The spine 10 has a cephalad direction 12, a caudal direction 14, an anterior direction 16, a posterior direction 18, and a medial/lateral axis 20, all of which are oriented as shown by the arrows bearing the same reference numerals. The spine 10 has a sagittal plane 22, which defines the plane of symmetry of the spine 10, and is thus positioned between the left and right sides of the spine 10. The sagittal plane 22 is perpendicular to the medial/lateral axis 20. In this context, "symmetry" is used loosely because natural anatomical differences will be present between the left and right sides of the spine 10. "Left" and "right" are used with reference to a posterior view, i.e., a view from behind the spine 10. "Medial" refers to a position or orientation toward the sagittal plane 22, and "lateral" refers to a position or orientation relatively further from the sagittal plane 22.

As shown, the portion of the spine 10 illustrated in FIG. 1 includes a first vertebra 24, which may be the L5 (Fifth Lumbar) vertebra of a patient, and a second vertebra 26, which may be the L4 (Fourth Lumbar) vertebra of the patient. The systems and methods may be applicable to any vertebra or vertebrae of the spine 10 and/or the sacrum (not shown); however, the embodiment shown the Figures may be particularly applicable to the L4 and L5 vertebrae. In this application, the term "vertebra" may be broadly interpreted to include the sacrum.

As shown, the first vertebra 24 has two pedicles 30 and a posterior arch, or lamina 32, that extends between the posterior ends of the pedicles 30 to couple the pedicles 30 together. The first vertebra 24 also has a pair of transverse processes 34 that extend laterally from the pedicles 30 generally along the medial/lateral axis 20, and a spinous process 36 that extends from the lamina 32 along the posterior direction 18.

The first vertebra 24 also has a pair of superior facets 38, which are positioned toward the top of the first vertebra 24 and face generally medially. Additionally, the first vertebra 24 has inferior facets 40, which are positioned toward the bottom of the first vertebra 24 and face generally laterally. Each of the pedicles 30 of the first vertebra 24 has a saddle point 42, which is positioned generally at the center of the juncture of each superior facet 38 with the adjacent transverse process 34.

Similarly, the second vertebra 26 has two pedicles 50 and a posterior arch, or lamina 52, that extends between the posterior ends of the pedicles 50 to couple the pedicles 50 together. The second vertebra 26 also has a pair of transverse processes 54 that extend from the pedicles 50 generally along the medial/lateral axis 20, and a spinous process 56 that extends from the lamina 52 along the posterior direction 18.

The second vertebra 26 also has a pair of superior facets 58, which are positioned toward the top of the second vertebra 26 and face generally inward. Additionally, the second vertebra 26 has inferior facets 60; which are positioned toward the bottom of the second vertebra 26 and face generally outward. Each of the pedicles 60 of the second vertebra 26 has a saddle point 62, which is positioned generally at the center of the juncture of each superior facet 58 with the adjacent transverse process 54.

The superior facets 38 of the first vertebra 24 articulate (i.e., slide and/or press) against the inferior facets 60 of the second vertebra 26 to limit relative motion between the first and second vertebrae 24, 26. Thus, the combination of each superior facet 38 with the adjacent inferior facet 60 provides a facet joint 64. The first and second vertebrae 24, 26 thus define two facet joints 64 that span the distance between the first and second vertebrae 24, 26. The inferior facets 40 of the first vertebra 40 and the superior facets 58 of the second vertebra 26 are part of other facet joints that control motion between the first and second vertebrae 24, 26 and adjacent vertebrae (not shown) and/or the sacrum (also not shown).

Each of the facet joints 64 may be covered by a capsule (not shown) containing a fluid (not shown) that reduces wear of the facets 38, 60 and facilitates articulation. Additionally, layers of cartilage (not shown) may cover the facets 38, 60 to further reduce wear and facilitate articulation. These anatomical structures, as well as the various muscles, ligaments, and nerves of the spine, will not be depicted in the Figures to enhance the clarity of the disclosure.

Figure 2:
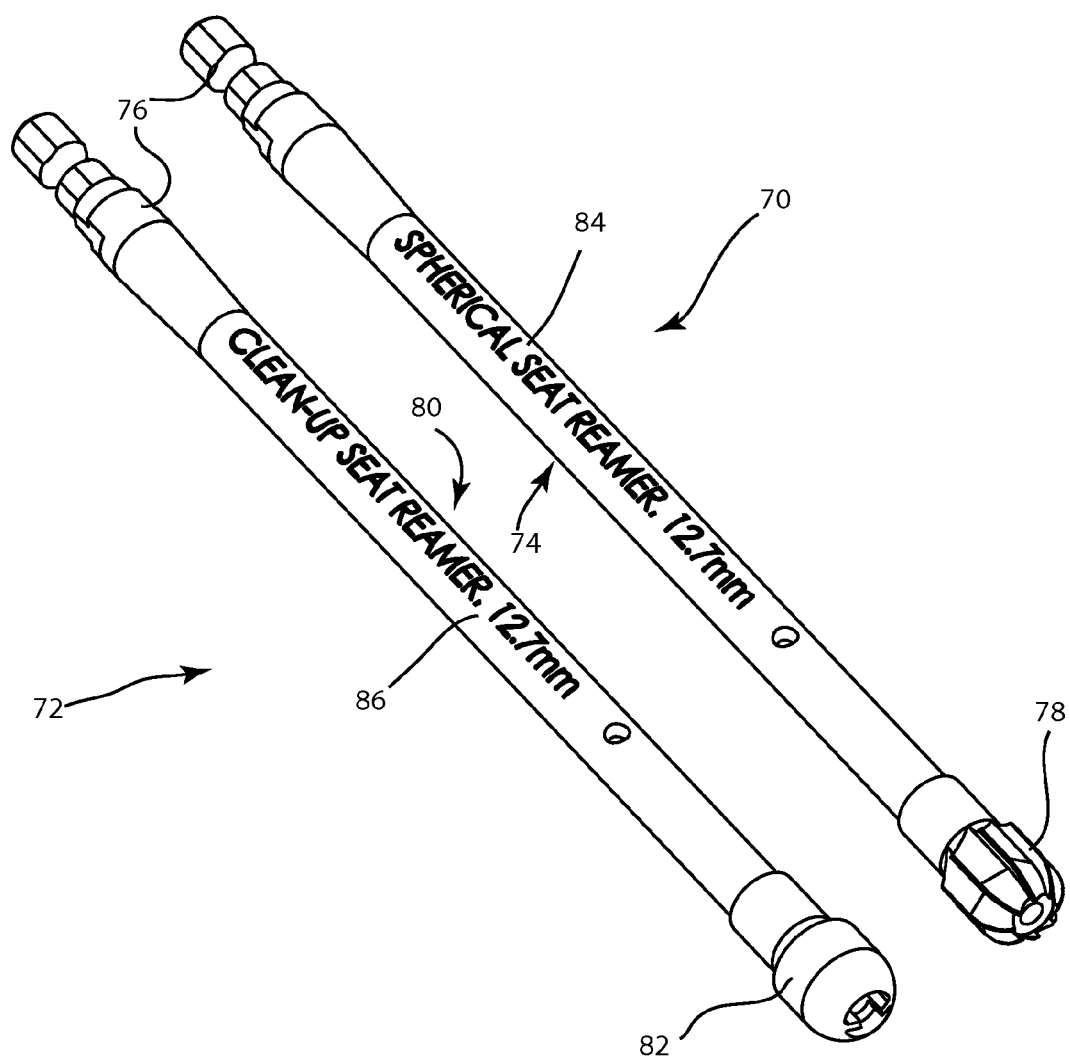
FIG. 2 is a perspective view of a primary reamer and a secondary reamer usable to provide semispherical resections in the spinal column of FIG. 1.

Referring to FIG. 2, a perspective view illustrates a primary reamer 70 and a secondary reamer 72 that may be used to form semispherical interfaces, or semispherical surfaces, on the saddle points 42, 62 of the vertebrae 24, 26, as will be illustrated subsequently. The primary reamer 70 has a shaft 74, a torque interface 76, which may include a hexagonal cross-section designed to facilitate receipt of torque from a source such as a handle or a motor, and a head 78 designed to cut away bone tissue. Similarly, the secondary reamer 72 has a shaft 80, a torque interface 76, and a head 82.

Each of the reamers 70, 72 may have an indicator that clearly specifies its identity and/or intended use. For example, the shaft of the primary reamer 70 has an indicator 84 that indicates that it is for primary reaming of a spherical seat, and the secondary reamer 72 has an indicator 86 that indicates that it may be used to clean or finish a previously reamed semispherical seat.

Figure 3:
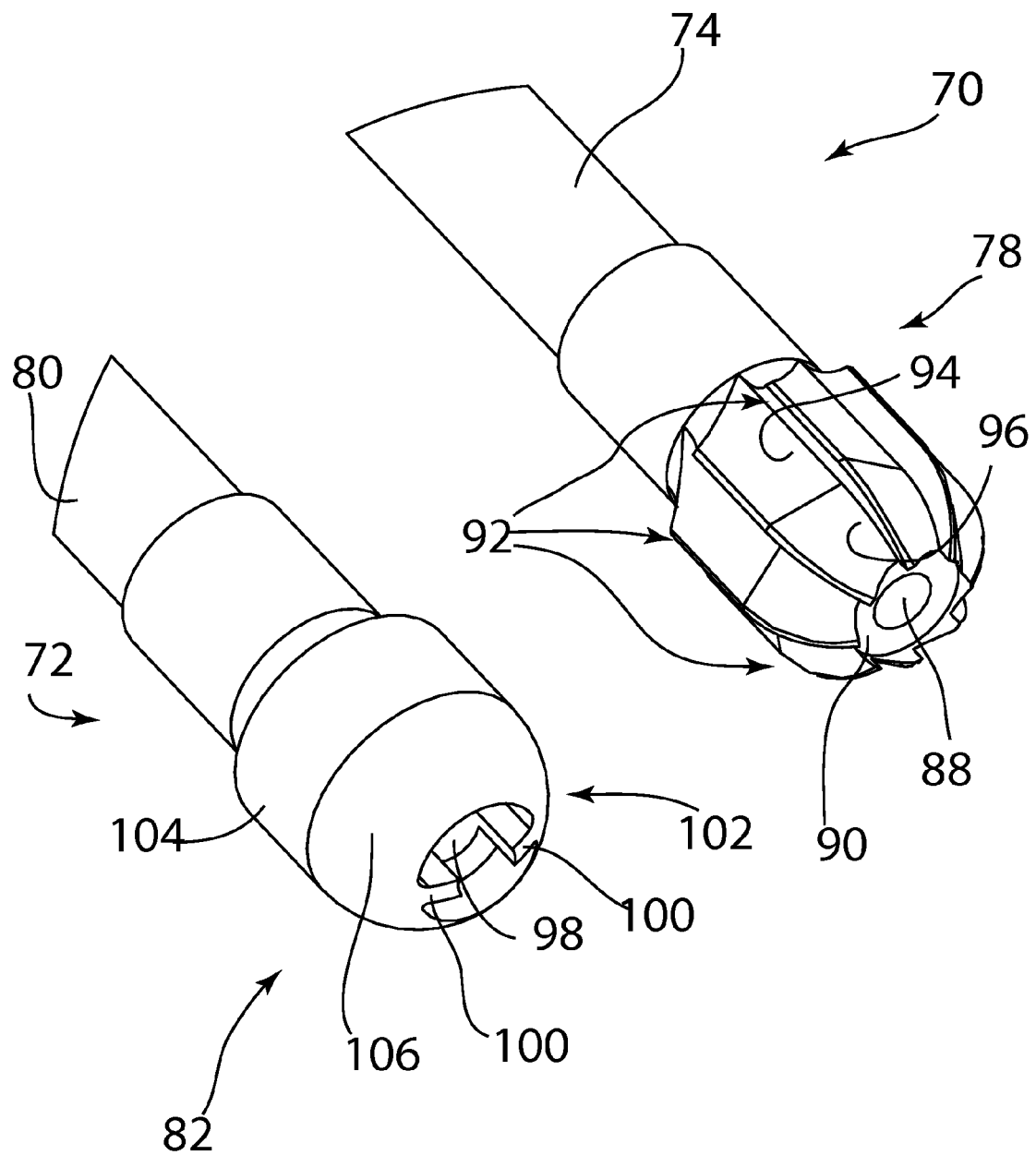
FIG. 3 is an enlarged, perspective view of the heads of the primary and secondary reamers of FIG. 2.

Referring to FIG. 3, an enlarged, perspective view illustrates the heads 78, 82 of the reamers 70, 72 of FIG. 2. As shown, the primary reamer 70 has a bore 88 that may pass through the head 78 and into the shaft 74. The bore 88 is sized to receive a guide wire or a similar structure to control the position of the head 78. Furthermore, the head 78 has a flat surface 90 oriented generally perpendicular to an axis (not shown) of the shaft 74. The head 78 also has a plurality of cutting flanges 92 distributed about the circumference of the head 78. Each of the cutting flanges 92 has a straight portion 94 and an arcuate portion 96 adjacent to the flat surface 90.

In operation, the primary reamer 70 is registered on a guide wire or the like, and advanced toward the bone surface to be resected. The arcuate portions 96 then contact the bone and resect away bone tissue to provide a generally semispherical indentation in the bone. The primary reamer 70 continues to advance into the bone until the flat surface 90 abuts the bone. The primary reamer 70 is then substantially unable to advance further. Thus, the flat surface 90 controls the depth of reaming.

The secondary reamer 72 also has a bore 98 that passes though the head 82 of the secondary reamer 72 and into the corresponding shaft 80. The bore 98 may also receive a guide wire or the like to help control positioning of the head 82. The head 82 has a pair of central teeth 100 that protrude inward on either side of an (not shown) of the shaft 80. The head 82 also has a dome 102 with a straight portion 104 having a generally cylindrical shape, and an arcuate portion 106 with a semispherical profile that caps the cylindrical shape of the straight portion 104.

In operation, the secondary reamer 72 may be used to remove bone tissue left by the primary reamer 70. More precisely, the primary reamer 70 leaves the portion of bone abutting the flat surface 90 intact, and thus forms a surface that is not entirely semispherical. The secondary reamer 72 removes the excess bone left by the primary reamer 70. The secondary reamer 72 may be registered in the same manner as the primary reamer 70, and advanced into the indentation formed by the primary reamer 70. The central teeth 82 remove the central bone portion that abutted the flat surface 90 to leave an indentation that is more precisely semispherical. The dome 102 is unable to remove any additional bone tissue, so the secondary reamer 72 is unable to significantly deepen the indentation.

Figure 4:
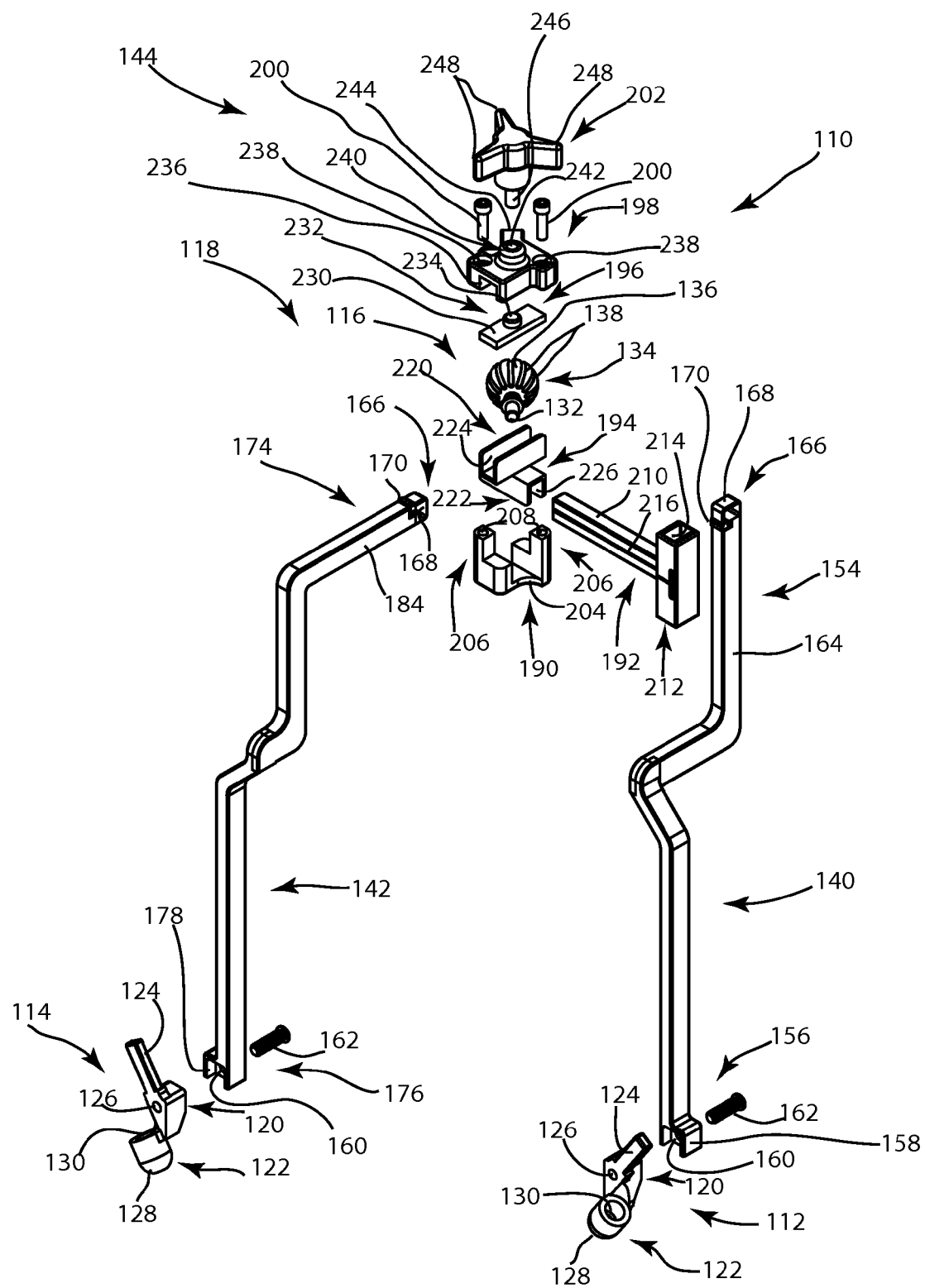
FIG. 4 is an exploded, perspective view of a frame attachable to the L5 vertebra of FIG. 1 to guide measurement and resection of bony landmarks of the spinal column.

Referring to FIG. 4, an exploded, perspective view illustrates a "sagittal bridge," or frame 110, that can be attached to the spine 10 to serve as a base for measurement and resection. The frame 110 includes a first anchor 112 and a second anchor 114 that may be generally symmetrically positioned on either side of the sagittal plane 22 and attached, for example, to the saddle points 42 of the pedicles 30 of the first vertebra 24. The frame 110 also has an external anchor 116 that facilitates attachment of the frame 110 to an external structure such as an operating table or the like. A bridging structure 118 couples the first anchor 112, second anchor 114, and external anchor 116 together in a manner that permits adjustment of the relative positions of the first and second anchors 112, 114 to account for anatomical differentiation in spinal anatomy.

As shown, each of the first and second anchors 112, 114 has a main body 120, an anchoring feature 122, and a registration feature in the form of a guide post 124. Each main body 120 has a generally rectangular, tapered shape and is integrally formed with the corresponding anchoring feature 122 and guide post 124. Each of the anchoring features 122 has a semispherical surface 128 that may be substantially halfspherical in shape. Each of the anchoring features 122 also has a bore 130 that extends through the corresponding semispherical surface 128.

Each of the guide posts 124 may have a generally rectangular cross section. The generally rectangular cross section may have two long sides and two short sides, so that a corresponding generally rectangular bore of a surgical instrument may only slide into engagement with the guide post 124 in two different orientations. Of the two orientations, the wrong orientation may be made obvious via interference of the frame 110 with the surgical instrument, handle positioning, marking of the surgical instrument, or any other method known in the art. In alternative embodiments, a registration post may have a shape that is engageable with a corresponding bore in only one orientation. For example, a circular shaft with a single flat side, a trapezoidal shape, or the like may be used to ensure that engagement is able to occur along only one relative orientation.

The external anchor 116 has an attachment post that permits attachment of the external anchor 116 to the bridging structure 118. Additionally, the external anchor 116 has an external anchoring feature 134 that can easily be gripped by a stationary external support. The external anchoring feature 134 has a generally spherical surface 136 with a plurality of grooves 138 distributed about its surface. The generally spherical surface may easily be gripped by a grip (not shown in FIG. 4) having a corresponding concave semispherical surface.

As shown in FIG. 4, the bridging structure 118 has a first arm 140 and a second arm 142 that cooperate to couple the first and second anchors 112, 114 and the external anchor 116 together. The first and second arms 140, 142 are movable with respect to each other in such a manner that the relative positions of the first and second anchors 112, 114 can be changed in three dimensions. A locking mechanism 144 enables the relative positions of the anchors 112, 114 to be simultaneously locked in all three dimensions. The manner in which the bridging structure 118 permits relative movement and locking of the arms 140, 142 will be described in greater detail subsequently.

The first arm 140 has a first end 154 coupled to the locking mechanism 144 and to the external anchor 116. Additionally, the first arm 140 has a second end 156 attached to the first anchor 112. The first end 156 has an alcove 158 with a generally rectangular shape. A hole 160 passes through one wall of the alcove 158 such that a fastener such as a screw 162 may be inserted through the hole 160 to engage the corresponding aperture 126 of the first anchor 112. The screw 162 and the aperture 126 may each be threaded so that the screw 162 threadably engages the aperture 126. The generally rectangular end of the main body 120 of the first anchor 112 fits into the alcove 158 in such a manner that relative rotation between the first anchor 112 and the second end 156 is unable to occur.

The first end 154 includes a first rod 164 along which relative sliding motion between the arms 140, 142 can occur to provide relative translation along one axis, or one dimension. The first end 154 also has a stop feature 166 that limits motion along the first rod 164. The stop feature 166 may include a flexible flange 168 that extends away from, and then back toward, the first rod 164 along a generally U-shaped path. The flange 168 terminates in a stopper 170 that protrudes outward from the flange 168 and the aligned surface of the first rod 164.

When a slider slides over the stop feature 166 and onto the first rod 164, the relatively small thickness of the flexible flange 168 enables it to bend inward to remove the stopper 170 from the pathway of the slider. However, when the slider slides back toward the stop feature 166, the flexible flange 168 is only able to spring outward such that the stopper 170 further impedes removal of the slider from the first rod 164. The stopper 170 may be ramped on one side, and not on the other, to permit one-way passage of the slider as outlined above.

Like the first arm 140, the second arm 142 has a first end 174 coupled to the locking mechanism 144 and to the external anchor 116. Additionally, the second arm 142 has a second end 176 attached to the first anchor 112. The second end 176 has an alcove 178 that is a substantial mirror image of the alcove 158 of the first arm 140. Thus, a second fastener such as a screw 162 may be inserted through a hole 160 formed in one wall of the alcove 178 and threaded into engagement with the aperture 126 of the second anchor 114. As with the alcove 158, the generally rectangular end of the main body 120 of the second anchor 114 fits into the alcove 178 in such a manner that relative rotation between the first anchor 114 and the second end 176 is unable to occur.

The first end 174 of the second arm 142 has a second rod 184 that permits relative sliding motion between the arms 140, 142 along a second axis perpendicular to the first rod 164. The first end 174 also has a stop feature 166 that limits motion along the second rod 164 in a manner similar to that of the stop feature 166 of the first end 154 of the first arm 140.

The locking mechanism 144 includes a variety of components that permit tri-axial relative translation between the first ends 154, 174 of the arms 140, 142. More precisely, the locking mechanism 144 includes a first retention member 190, a first slider member 192, a second slider member 194, a compression member 196, a second retention member 198, two fasteners such as screws 200, and a handle 202. The interaction of these components to provide relative motion and locking will be described in greater detail as follows.

The first retention member 190 has a base plate 204 and a pair of receiving posts 206 that extend from the base plate 204, toward the handle 202. Each of the receiving posts 206 has a hole 208 that may be threaded to enable threadable engagement with the screws 200.

The first slider member 192 may have a third rod 210 that enables relative motion between the first and second arms 140, 142 along a third axis orthogonal to the first and second rods 164, 184. Additionally, the first slider member 192 has a first slider 212 that captures and slides along the first rod 164. The first slider 212 has a bore 214 with a generally rectangular shape sized to receive the first rod 164 with clearance so that the first rod 164 is able to slide through the bore 214.

The first slider member 192 also has a slot 216 that bisects the third rod 210 and substantially bisects the first slider 212. The slot 216 has a certain width that can be compressed by pressing the two halves of the third rod 210 together, thereby deforming the walls of the first slider 212 to bend the bore 214 from its normally straight shape. Due to the close fit between the first slider 212 and the first rod 164, bending of the bore 214 causes frictional contact between the first slider 212 and the first rod 164. Thus, compression on the third rod 210 arrests motion of the first slider 212 along the first rod 164.

The second slider member 194 has a second slider 220 and a third slider 222, which are oriented orthogonally to each other and to the first slider 212. The second slider 220 has a bore 224 with a generally rectangular shape, with one unbounded side. Similarly, the third slider 222 has a bore 226 with a generally rectangular shape, with one unbounded side. The bores 224 and 226 of the second and third sliders 220, 222 are generally sized and shaped to slide along the corresponding second and third rods 184, 210, respectively.

Thus, the first, second, and third rods 164, 184, 210 cooperate with the first, second, and third sliders 212, 220, 222 to provide three linear joints that enable relative motion between the first and second arms 140, 142 along three orthogonal axes. In alternative embodiments, motion along only one or two axes may be desired. In other alternative embodiments, one or more joints with non-translational motion, such as rotary joints, may be used in place of any of the linear joints of the frame 110. However, use of the linear joints is advantageous because the guide posts 124 can be kept in a substantially fixed orientation relative to each other when the joints are adjusted. Thus, the frame 110 accounts for three-dimensional variation in the relative positions of the saddle points 42 of the first vertebra 24, while still maintaining the desired coordination between operations that are to be keyed to the guide posts 124.

Returning to the embodiment of FIG. 4, the compression member 196 may have a plate 230 with a generally rectangular shape. A central plateau 232 protrudes from the center of one side of the plate 230, toward the handle 202. The central plateau 232 has an alcove 234 with a generally circular cross section. The compression member 196 may be pressed toward the second slider 220 to cause locking of all three linear joints in a manner that will be described subsequently.

The second retention member 198 has a trough 236 within which the compression member 196 may be generally positioned. The second retention member 198 also has two holes 238 through which the screws 200 may pass to anchor in the holes 208 of the receiving posts 206 of the first retention member 190. Additionally, the second retention member 198 has a central plateau 240 in which an aperture 242 is formed. The aperture 242 may be threaded. The second retention member 198 also has an attachment projection that protrudes and has a bore (not shown) sized to receive the attachment post 132 of the external anchor 116.

The handle 202 has a threaded stud 246 sized to threadably engage the aperture 242 of the central plateau 240 of the second retention member 198. Furthermore, the handle 202 has wings 248 that facilitate gripping and rotation of the handle 202 by hand. The handle 202 may be used to move the locking mechanism 144 between a locked configuration, in which the three linear joints are relatively freely movable to enable tri-axial relative translation between the anchors 112, 114, and an unlocked configuration in which the anchors 112, 114 are fixed with respect to each other.

The first retention member 190, first slider member 192, second slider member 194, compression member 196, second retention member 198, screws 200, and handle 202 may be relatively easily assembled to form the bridging structure 118. According to one method of assembly, the compression member 196 may first be positioned in the trough 236 of the second retention member 198. The second slider member 194 may be positioned to rest on the base plate 204 of the first retention member 190, between the receiving posts 206 of the first retention member 190.

The screws 200 may be inserted through the holes 238 of the second retention member 198 and rotated into threaded engagement with the holes 208 of the receiving posts 206. The screws 200 may be tightened such that the receiving posts 206 abut the second retention member 198. The threaded stud 246 of the handle 202 may be inserted through the aperture 242 of the central plateau 240 of the second retention member 198 and rotated into threaded engagement with the aperture until the end of the threaded stud 246 enters the alcove 234 of the central plateau 232 of the compression member 196.

With the handle 202 positioned so as to allow the compression member 196 to remain in a retracted position, the first rod 164 may be inserted into the first slider 212, the second rod 184 may be inserted into the second slider 220, and the third rod 210 may be inserted into the third slider 222. The first and second sliders 212, 220 may be translated to slide past the stop features 166 at the ends of the first and second rods 164, 184, respectively. Assembly of the locking mechanism 144 is then complete.

Next, the external anchor 116 may be attached to the locking mechanism 144. More precisely, the attachment post 132 of the external anchor 116 may be inserted into the attachment projection 244 of the second retention member 198 and retained via interference fitting, welding, or the like. The anchors 112, 114 may be attached to the second ends 156, 176 of the first and second arms 140, 142 via the screws 162 in the manner indicated previously to complete assembly of the bridging structure 118.

Figure 5:
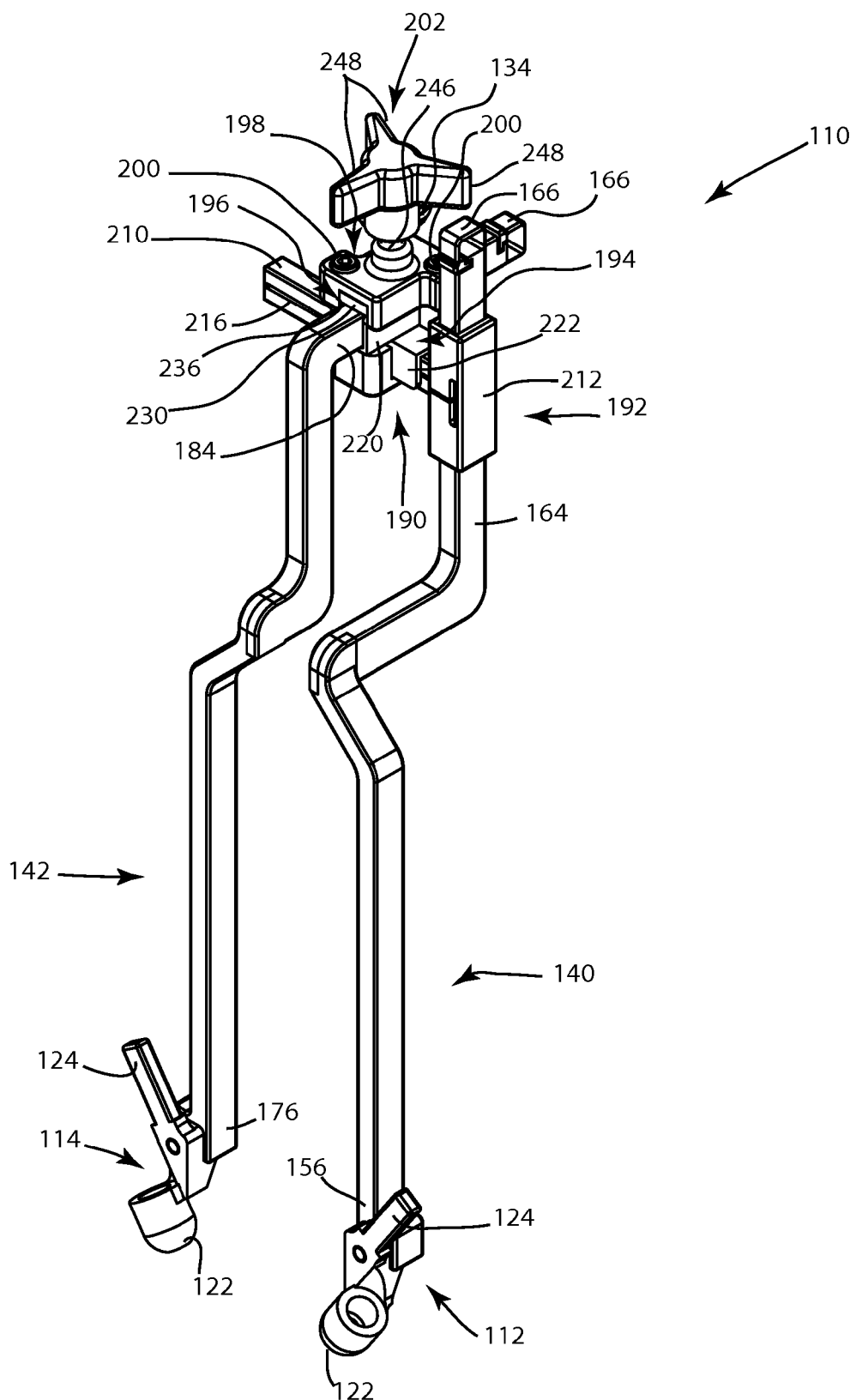
FIG. 5 is a perspective view of the frame of FIG. 4, in a fully assembled state.

Referring to FIG. 5, a perspective view illustrates the frame 110 in a fully assembled state. The anchoring features 122 of the anchors 112, 114 are ready to be attached to the saddle points 42 of the first vertebra 24. With the locking mechanism 144 in the unlocked configuration, the rods 164, 184, 210 are able to slide relatively freely through the sliders 212, 220, 222, respectively to permit tri-axial adjustment of the relative positions of the first and second anchors 112, 114. This permits the frame 110 to be easily adapted to a variety of spinal morphologies, including bone structures that are asymmetrical across the sagittal plane 22.

After the anchors 112, 114 have been relatively positioned as desired, the handle 202 may be rotated by hand to press the compression member 196 against the adjacent side of the second rod 184. As a result, the opposite side of the second rod 184 is pressed against the bore 224 of the second slider 220, thereby pressing the bore 226 of the third slider 222 against the third rod 210 to sandwich the third rod 210 between the third slider 222 and the base plate 204 of the first retention member 190. Consequently, the second and third sliders 220, 222 are unable to slide along the second and third rods 184, 210 due to transverse pressure acting transversely to compress the sliders 220, 222 against the rods 184, 210, respectively.

Compression of the third rod 210 also compresses the slot 216 of the first slider member 192, thereby compressing the sides of the first slider 212 against the first rod 164. Accordingly, the first slider 212 is also unable to slide along the first rod 164. Relative motion between the anchors 112, 114 is thus substantially prevented along all three joints, or all three orthogonal axes. This is accomplished by actuating only one user control, i.e., the handle 202. Separate controls need not be actuated to lock each of the joints of the bridging structure 118.

Figure 6:
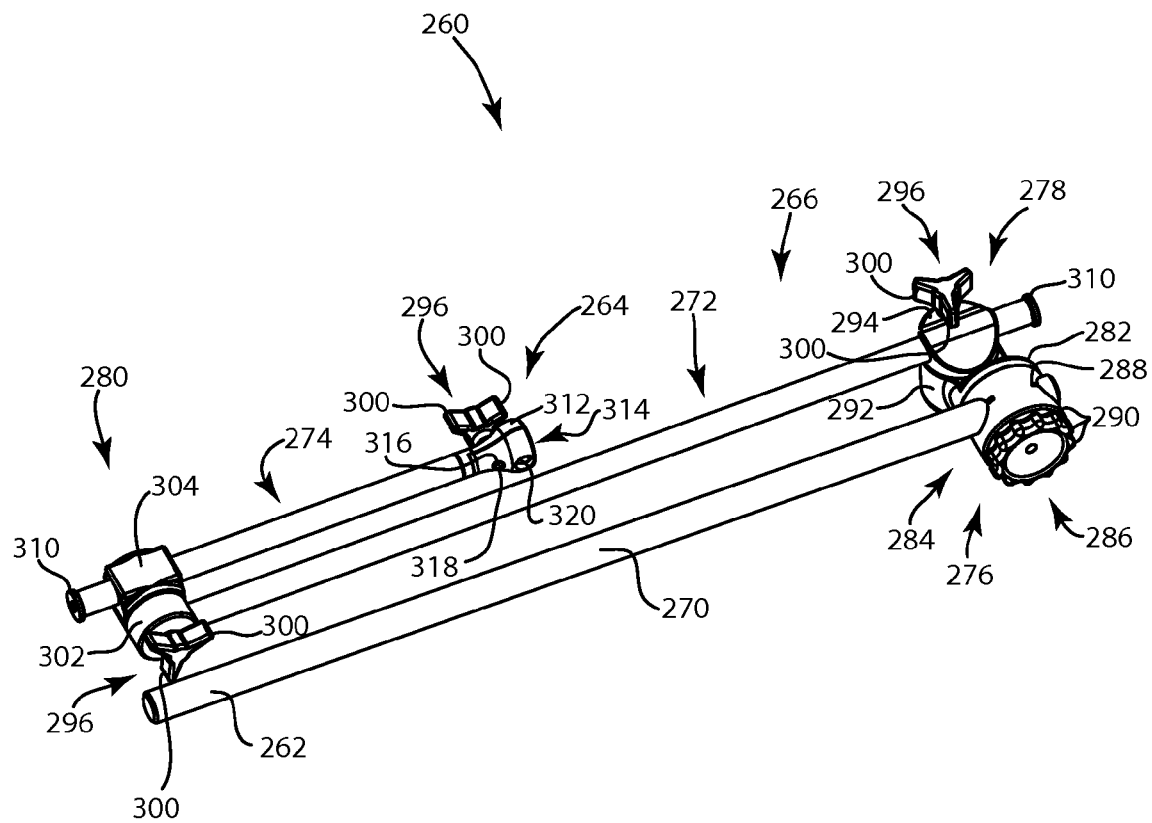
FIG. 6 is a perspective view of a stationary external support attachable to the frame of FIG. 4 to stabilize the frame.

Referring to FIG. 6, a perspective view illustrates a stationary external support 260 according to one embodiment of the invention. The stationary external support 260 may be coupled to a stationary object such as an operating table, wall, or the like, and to the external anchor 116 of the frame 110 to keep the frame 110 substantially stationary.

As shown in FIG. 6, the stationary external support 260 may have a fixed end 262 designed to be attached to the stationary object via a clamp (not shown), permanent welded attachment, or the like. The stationary external support 260 also has a grip 264 that can be used to grip the external anchor 116 of the frame 110 in a manner that will be described subsequently. The grip 264 and the first end 262 are movably coupled together via an adjustment structure 266.

The adjustment structure 266 may include a first rod 270, a second rod 272, and a third rod 274 that are coupled together via three joints, or more precisely, a first joint 276, a second joint 278, and a third joint 280. The rods 270, 272, 274 may be formed of a sturdy material such as steel, aluminum, or the like, and may be solid or hollow. Each of the joints 276, 278, 280 may provide at least rotary motion, and possibly linear motion, and may be securely lockable to enable the stationary external support 260 to provide stiff support to the frame 110.

The first joint 276 may have a main body 282 and a rod coupler 284 that is attached to the first rod 270 and is rotatably attached to the main body 282. Additionally, the first joint 276 has a handle 286 that can be rotated to control locking of the relative orientations of the main body 282 and the rod coupler 284. The rod coupler 284 has a slot 288 with a large portion through which the corresponding end of the first rod 270 passes.

The handle 286 has a plurality of ridges 290 that facilitate rotation of the handle 286 by hand, or through the use of a corresponding tool having an indentation that matches the shape of the handle 286. Clockwise rotation, or tightening, of the handle 286 substantially prevents further relative rotation between the rod coupler 284 and the main body 282 to keep the rod coupler 284 at a pre-established orientation with respect to the main body 282.

Additionally, if the first joint 276 also enables relative translation, tightening of the handle 286 may compress the rod coupler 284 to compress the slot 288 to grip the corresponding end of the first rod 270 to restrict relative translation between the rod coupler 284 and the first rod 270. Alternatively, the end of the first rod 270 may have a groove or other feature that cooperates with a corresponding feature within the rod coupler 284 to prevents relative translation. Gripping the end of the first rod 270 may also restrict rotation of the end of the first rod 270 within the rod coupler 284.

The second joint 278 may be configured somewhat similarly to the first joint 276, and may thus have a main body 292, a rod coupler 294, and a handle 296. The main body 292 is integrally formed with the main body 282 of the first joint 278. The rod coupler 294 is rotatably coupled to the main body 292 and retains the second rod 272 in a manner that may permit relative translation between the rod coupler 294 and the second rod 272. The handle 296 has wings 300 that facilitate gripping for manual rotation of the handle 296.

Tightening of the handle 286 of the first joint 276 substantially prevents relative rotation between the main body 292 and the rod coupler 294. Accordingly, the handle 286 is able to lock relative rotation between the first and second rods 270, 272 along three orthogonal axes. The handle 296 of the second joint 278 optionally also prevents relative translation and rotation between the rod coupler 294 and the second rod 272. Thus, the handle 296 of the second joint 278 may be capable of locking relative rotation and translation between the first and second rods 270, 272 along or about a single axis.

The third joint 280 is configured similarly to the first and second joints 276, 278. Thus, the third joint 280 has a main body 302, a rod coupler 304, and a handle 296. The main body 302 is rigidly attached to the end of the second rod 272. The main rod coupler 304 is rotatably coupled to the main body 302 and retains the third rod 274 in a manner that may permit relative translation between the rod coupler 304 and the third rod 274. The handle 296 has the same configuration as the handle 296 of the second joint 278. Tightening of the handle 296 substantially prevents relative rotation between the main body 302 and the rod coupler 304, and optionally also prevents relative translation between the rod coupler 304 and the third rod 274.

Furthermore, tightening the handle 296 prevents rotation of the end of the third rod 274 within the rod coupler 304. Thus, the handle 296 of the third joint 280 may be capable of locking relative rotation between the second and third rods 272, 274 about two orthogonal axes, and of locking relative translation between the second and third rods 272, 274 along one of the axes of rotation.

Each of the second and third rods 272, 274 has a stop 310 in the form of an outwardly-extending flange. The stops 310 prevent the second and third rods 272, 274 from being withdrawn from the rod couplers 294, 304 of the second and third joints 278, 280, respectively. Furthermore, each of the joints 276, 278, 280 may have a plurality of clocking features, such as internal ridges (not shown), which may restrict relative rotation of each of the joints 276, 278, 280 to a number of discrete positions, thereby enhancing the stability of the joints 276, 278, 280.

The grip 264 has a first gripping member 312, a second gripping member 314, and a handle 296. The first gripping member 312 may be integrally formed with the third rod 274, and the second gripping member 314 may be separate from the first gripping member 312 so as to permit relative motion between the first and second gripping members 312, 314. The handle 296 has the same configuration as the handles 296 of the second joint 278 and the third joint 280. The handle 296 has a threaded stud 316 that passes through a hole (not shown) of the first gripping member 312 and threadably engages a threaded hole 318 of the second gripping member 314.

Clockwise rotation, or tightening, of the handle 296 of the grip 264 may draw the first and second gripping members 312, 314 together. The first and second gripping members 312, 314 may cooperate to define a semispherical surface 320 with a concave configuration sized to receive the generally spherical surface 136 of the external anchor 116. The generally spherical surface 136 of the external anchor 116 may be inserted into the semispherical surface 320 of the grip 264 prior to tightening of the handle 296 so that the generally spherical surface 136 is unable to be drawn free of the semispherical surface 320 without loosening of the handle 296. The ridges 138 of the generally spherical surface 136 enhance locking and help to prevent relative rotation between the external anchor 116 and the grip 264.

Figure 7:
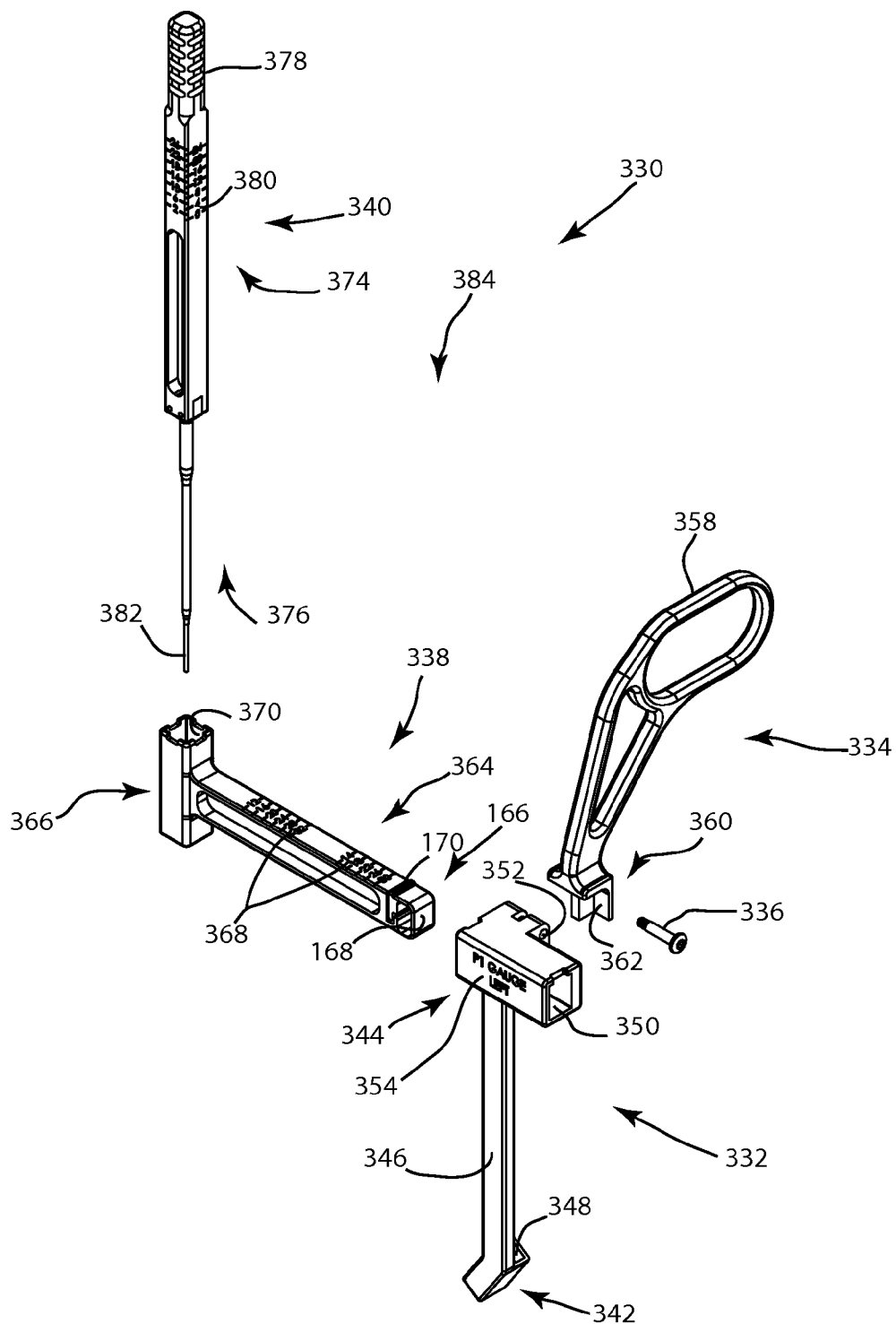
FIG. 7 is an exploded, perspective view of a facet measurement tool capable of registering on the frame of FIG. 4 to measure the position of a most medial and anterior surface of a superior facet of the spinal column.

Referring to FIG. 7, an exploded, perspective view illustrates a facet measurement tool 330 according to one embodiment of the invention. The facet measurement tool 330 may be designed to register on the frame 110 to measure a bony landmark such as the most medial and anterior surface of a superior facet, otherwise denoted "P1."

As shown, the facet measurement tool 330 may have a registration member 332, a handle member 334, a fastener such as a screw 336, a slider member 338, and a contact member 340. The registration member 332 has a registration interface 342, a first slider 344, and an arm 346 that couples the registration interface 342 and the first slider 344 together. The registration interface 342 has a bore 348 with a generally rectangular shape sized to receive the guide post 124 of the first anchor 112 of the frame 110. The first slider 344 also has a bore 350 with a generally rectangular cross sectional shape suitable for receiving a rod having a corresponding rectangular cross section.

Additionally, the first slider 344 has an aperture 352 that may be threaded to permit threaded engagement of the screw 336 with the aperture 352. The first slider 344 also has an indicator 354 that indicates the identity and proper use of the registration member 332 to help prevent improper assembly or use of the registration member 332. As shown in FIG. 7, the indicator 354 indicates that the registration member 332 is to be used for measurement of P1, or the most medial and anterior surface of a superior facet, on the left-hand side of a vertebra.

The handle member 334 has a handle 358 shaped to be grasped by a hand of a user, and an attachment end 360 attachable to the first slider 344 of the registration member 332. The attachment end 360 has an alcove 362 designed to conform to the shape of the first slider 344 to prevent relative rotation between the handle member 334 and the first slider 344. The alcove 362 has a hole (not shown) that permits passage of the screw 336 therethrough to attach the attachment end 360 to the first slider 344.

The slider member 338 has a first rod 364 slidable within the first slider 344 and a second slider 366 shaped to slidably receive the contact member 340. The first rod 364 is bounded by a generally rectangular cross sectional shape, and has markings 368 arranged in two separate groupings along its length. The second slider 366 has a bore 370 with a generally rectangular cross sectional shape similar to the bore 350 of the first slider 344. A stop feature 166 like those of the frame 110 is positioned on the opposite end of the first rod 364 from the second slider 366 to prevent unintended withdrawal the first rod 364 from the bore 350 of the first slider 344.

The contact member 340 has a second rod 374, a contact extension 376 extending from the second rod 374, and a grip 378 that extends from the opposite end of the second rod 374. The second rod 374 is bounded by a generally rectangular cross section and has a plurality of markings 380 distributed along one end, adjacent to the grip 378. The contact extension 376 has a contact feature 382 shaped to contact P1 to permit measurement of the position of P1 with the facet measurement tool 330.

According to one method of assembling the facet measurement tool 330, the attachment end 360 of the handle member 334 may first be attached to the first slider 344 by inserting the screw 336 through the hole (not shown) of the alcove 362 and then threadably anchoring the screw 336 in the aperture 352 of the first slider 344. Then, the first rod 364 may be inserted into the bore 350 of the first slider 344 until the first slider 344 has moved past the stop feature 166. The contact member 340 may then be inserted into the bore 370 of the second slider 366 so that the second rod 374 is positioned within the bore 370 to complete assembly of the facet measurement tool 330.

Figure 8:
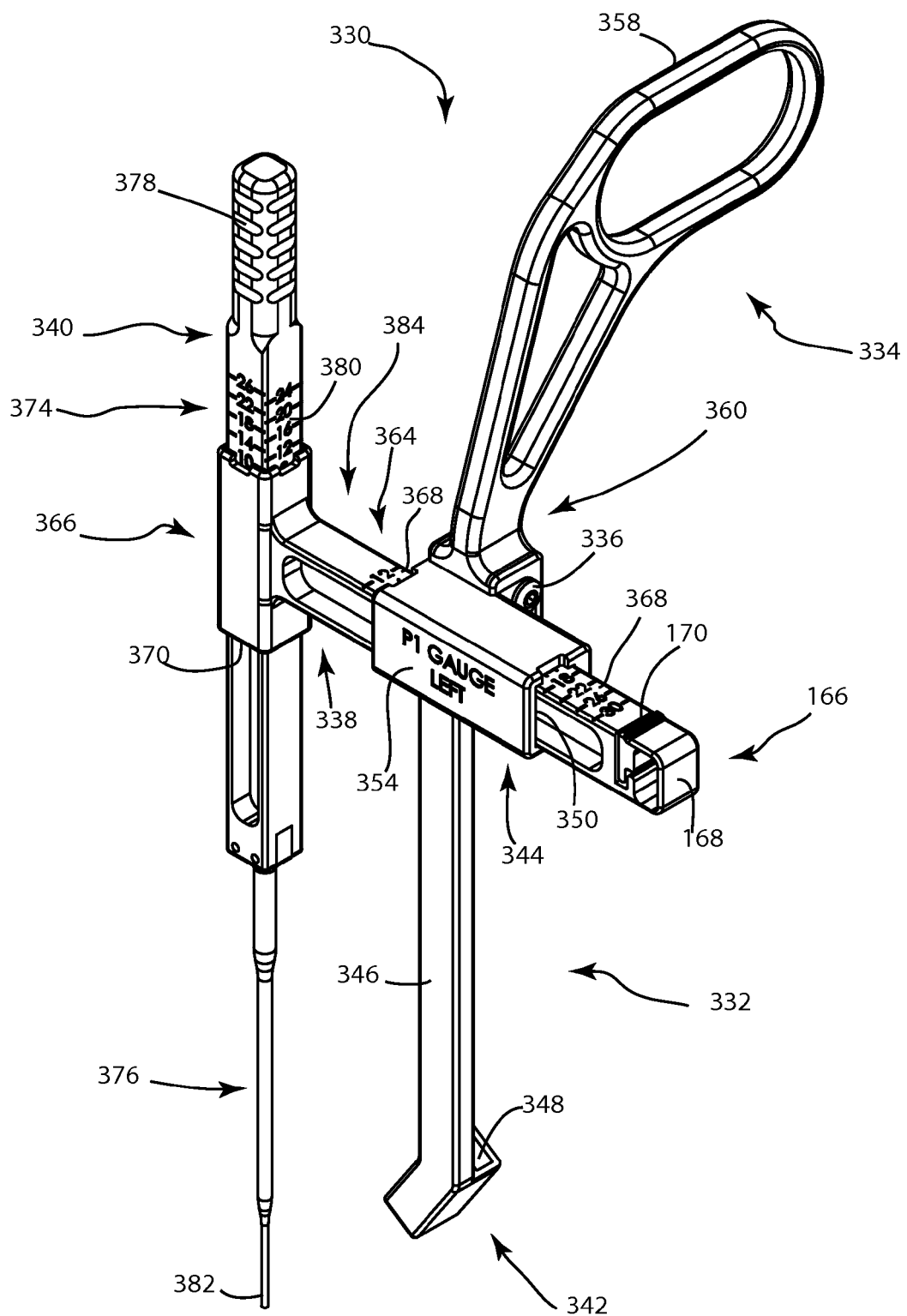
FIG. 8 is a perspective view of the facet measurement tool of FIG. 7, in a fully assembled state.

Referring to FIG. 8, a perspective view illustrates the facet measurement tool 330 in a fully assembled state. Once assembled, the registration member 332, slider member 338, and contact member 340 all combine to form a displacement structure 384 capable of permitting bi-axial variation in the relative positions of the registration interface 342 and the contact feature 382. More precisely, the first slider 344 and the first rod 364 cooperate to permit relative translation along one axis, and the second slider 366 and the second rod 374 cooperate to permit relative translation along an axis perpendicular to that of the first slider 344 and the first rod 364.

The registration member 332 is particular to the left-hand side, and a mirror image of the registration member 332 would be required for right-side measurement operations. However, the slider member 338 and the contact member 340 may be used for either left-hand side or right-hand side measurement, and simply be rotated 180° and assembled with a right-hand registration member, handle member, and screw (not shown) to provide a facet measurement tool for the right-hand side.

Figure 9:
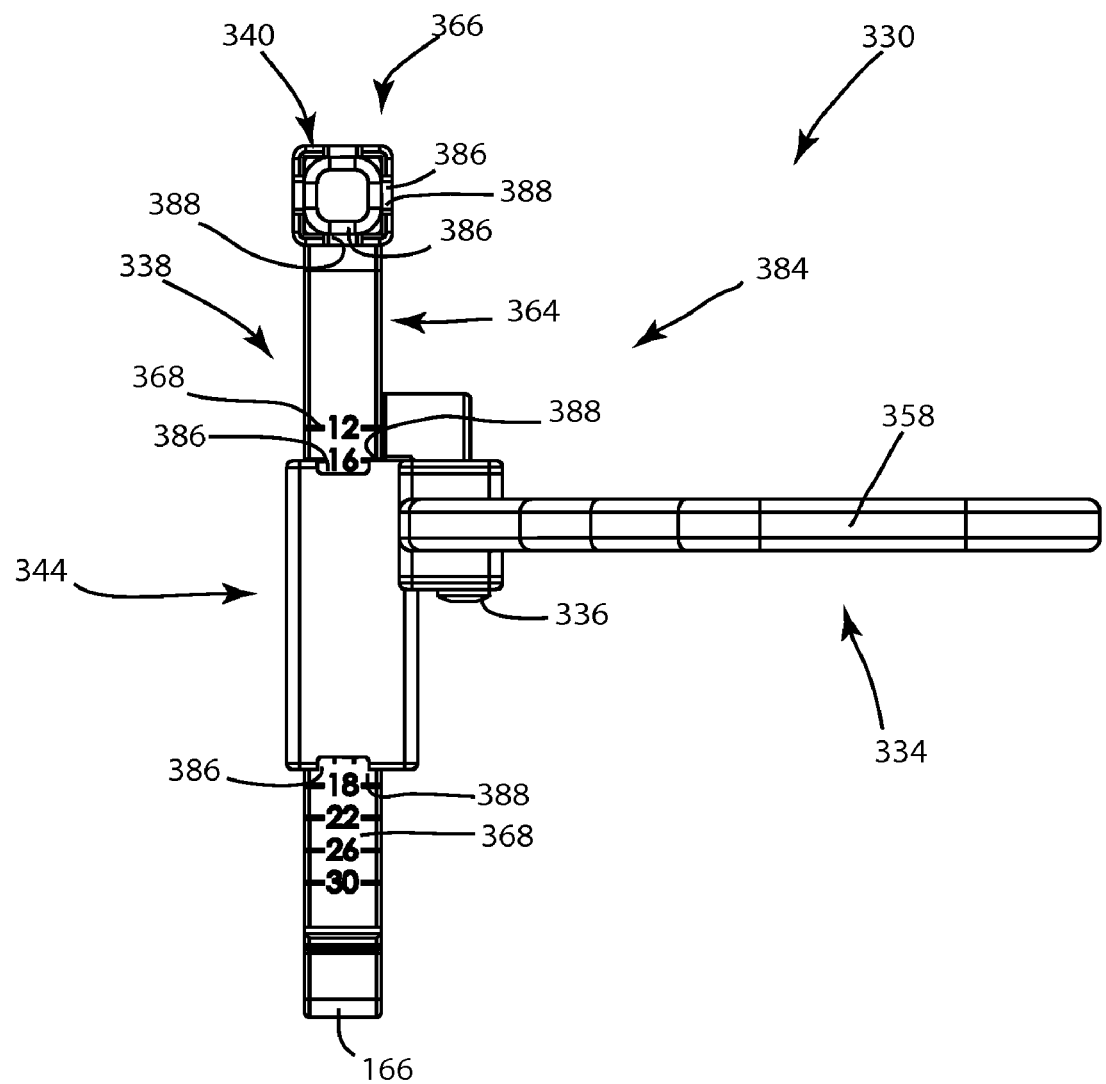
FIG. 9 is a plan view of the facet measurement tool of FIG. 7, in a fully assembled state.

Referring to FIG. 9, a plan view illustrates the facet measurement tool 330 in the fully assembled state. As shown, each of the first and second sliders 344, 366 has a plurality of recesses 386 positioned to facilitate reading of the markings 368, 380 of the first and second rods 364, 374, respectively. Each of the sliders 344, 366 also has measurement edges 388 that align with the tic marks adjacent to the numbers of the markings 368, 380 so that a clear and unambiguous measurement reading may be obtained.

As depicted in FIG. 9, the markings 368 are positioned on either side of the first slider 344. Additionally, the recesses 386 and measurement edges 388 are positioned on either end of the first slider 344 so that readings can be taken from either side. With respect to the orientation of FIG. 9, the markings 368 above the first slider 344 include numerals that fall in between the numerals of the markings 368 below the first slider 344. The appropriate measurement may be acquired from either set of the markings 368, depending on which set of the markings 368 has a tic mark closest to the corresponding measurement edge 388.

For example, in FIG. 9, the tic marks on either side of the number "16" are aligned with the measurement edges 388 on the adjacent end of the first slider 344. The markings 368 below the first slider 344 do not have a tic mark aligned with the corresponding measurement edges 388. Accordingly, "16" is the appropriate measurement. By permitting measurement readings to be taken on either side of the slider 344, the resolution of the facet measurement tool 330 along the axis of the first rod 364 can be effectively doubled.

The same principle is applied to the second slider 366. However, the markings 380 are not read from either side of the second slider 366. Rather, the markings 380 are offset on each pair of adjacent surfaces of the generally square cross section of the second rod 374, as shown in FIG. 9. Thus, the appropriate measurement for the second slider 366 and the second rod 374 is "10." In alternative embodiments, different offsets between all four sides may be used to further increase the resolution of the measurement provided by the second slider 366 and the second rod 374.

Figure 10:
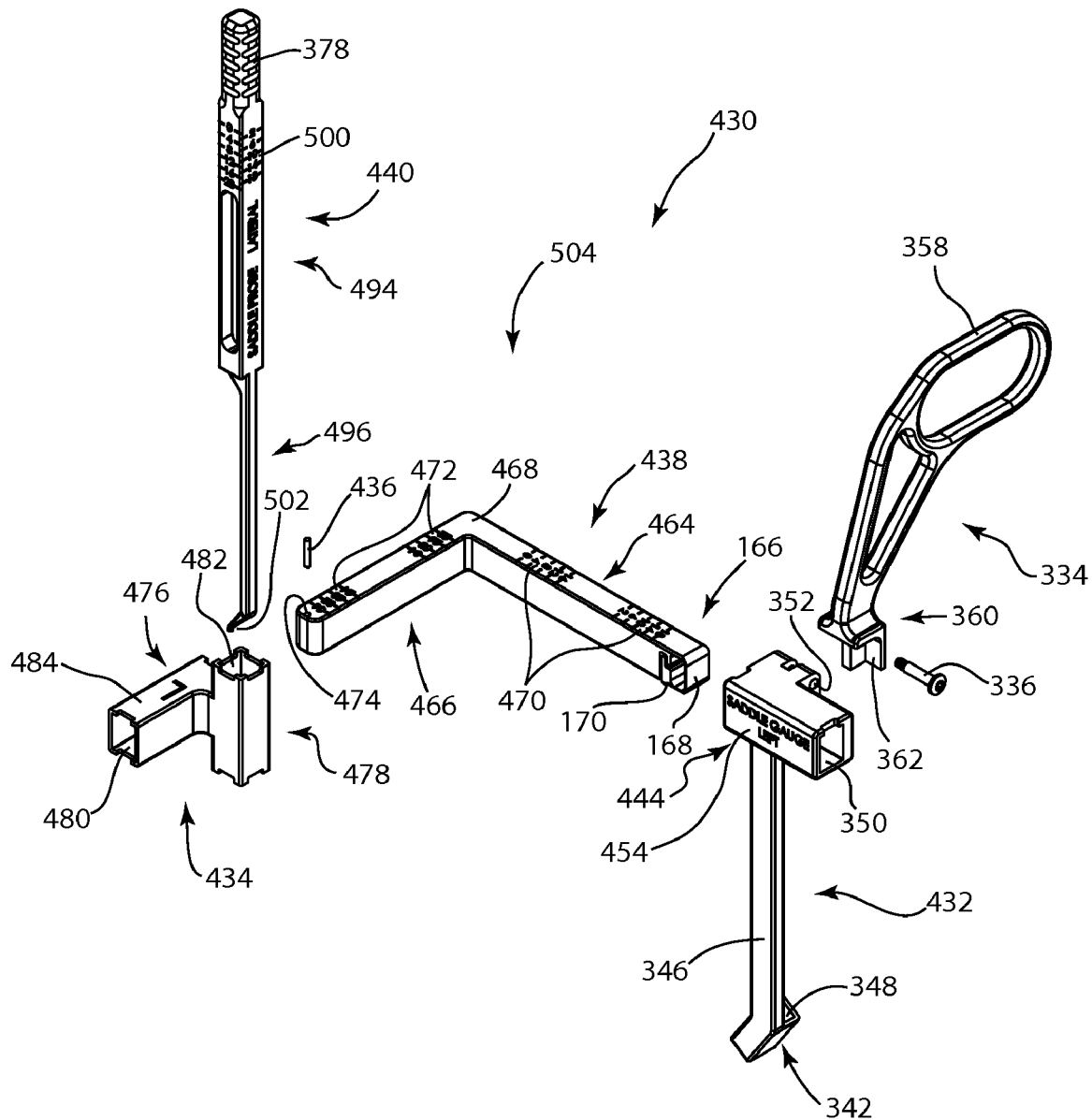
FIG. 10 is an exploded, perspective view of a pedicle measurement tool capable of registering on the frame of FIG. 4 to measure the position of a saddle point of a pedicle of the spinal column.

Referring to FIG. 10, an exploded, perspective view illustrates a pedicle measurement tool 430 according to one embodiment of the invention. The pedicle measurement tool 430 may be designed to register on the frame 110 to measure the three-dimensional position of a bony landmark such as one of the saddle points 62 of a pedicle 50 of the second vertebra 26.

As shown, the pedicle measurement tool 430 has a registration member 432, a handle member 334, a slider member 434, a screw 336, a pin 436, a rod member 438, and a contact member 440. The registration member 432 may be similar or even identical to the registration member 332 of the facet measurement tool 330, except that the registration member 432 has a first slider 444 with an indicator 454 that indicates that registration member 432 is for saddle point, or pedicle, measurement rather than facet measurement. The handle member 334 and the screw 336 may be identical to those of the previous embodiment.

The rod member 438 has a first rod 464 and a second rod 466 integrally formed with the first rod 464 and separated from the first rod 464 by a ninety-degree bend 468. The first rod 464 is designed to slide within the first slider 444, and the second rod 466 is designed to slide within a second slider. The first rod 464 has a plurality of markings 470 used to indicate measurements, and the second rod 466 has markings 472 that indicate measurements along an axis orthogonal to that of the first rod 464.

A stop feature 166 like those of the frame 110 is positioned at the end of the first rod 464 opposite to the bend 468 to prevent withdrawal of the first rod 464 from within the first slider 444. The second rod 466 has an aperture 474 positioned at the end of the second rod 466 opposite to the bend 468 to receive the pin 436. Once in place within the aperture 474, the pin 436 protrudes from the aperture 474 to act as a stop feature to prevent withdrawal of the second rod 466 from the second slider.

As shown, the slider member 434 has a second slider 476 and a third slider 478. The second slider 434 has a bore 480 with a generally rectangular cross section shaped to slidably receive the second rod 466. Similarly, the third slider 478 has a bore 482 with a generally rectangular cross section shaped to slidably receive the contact member 440. The second slider 476 has an indicator 484 that indicates the identity and intended use of the slider member 434, i.e., use on the pedicle measurement tool 430 for the left-hand side of the spine.

The contact member 440 has a third rod 494, a contact extension 496 extending from one end of the third rod 494, and a grip 378 extending from the opposite end of the third rod 494. The third rod 494 has a series of markings 500 distributed along its length. The third rod 494 is also bounded by a generally rectangular cross section so that the third rod 494 is slidably receivable within the bore 482 of the third slider 478. The contact extension 496 has a contact feature 502 shaped to contact the saddle point 62 of the left-hand side of the second vertebra 26 for accurate positional measurement.

The registration member 432, handle member 334, slider member 434, screw 336, pin 436, rod member 438, and contact member 440 may all be assembled in a variety of ways to provide the pedicle measurement tool 430. According to one method, the attachment end 360 of the handle member 334 is first attached to the first slider 444 via the screw 336 by inserting the screw 336 through the hole (not shown) of the alcove 362 and threadably anchoring the screw 336 in the aperture 352 of the first slider 444.

The first rod 464 is then inserted through the bore 350 of the first slider 444 until the first slider 444 has passed beyond the stop feature 166 at the end of the first rod 464. The second rod 466 is then inserted through the bore 480 of the second slider 476 until the second slider 476 has passed beyond the aperture 474 at the end of the second rod 466. Then, the pin 436 is inserted into the aperture 474 to prevent passage of the second slider 476 back over the aperture 474. The contact member 440 is then inserted through the bore 482 of the third slider 478 until the third rod 494 is positioned within the bore 482 to complete assembly of the pedicle measurement tool 430.

Figure 11:
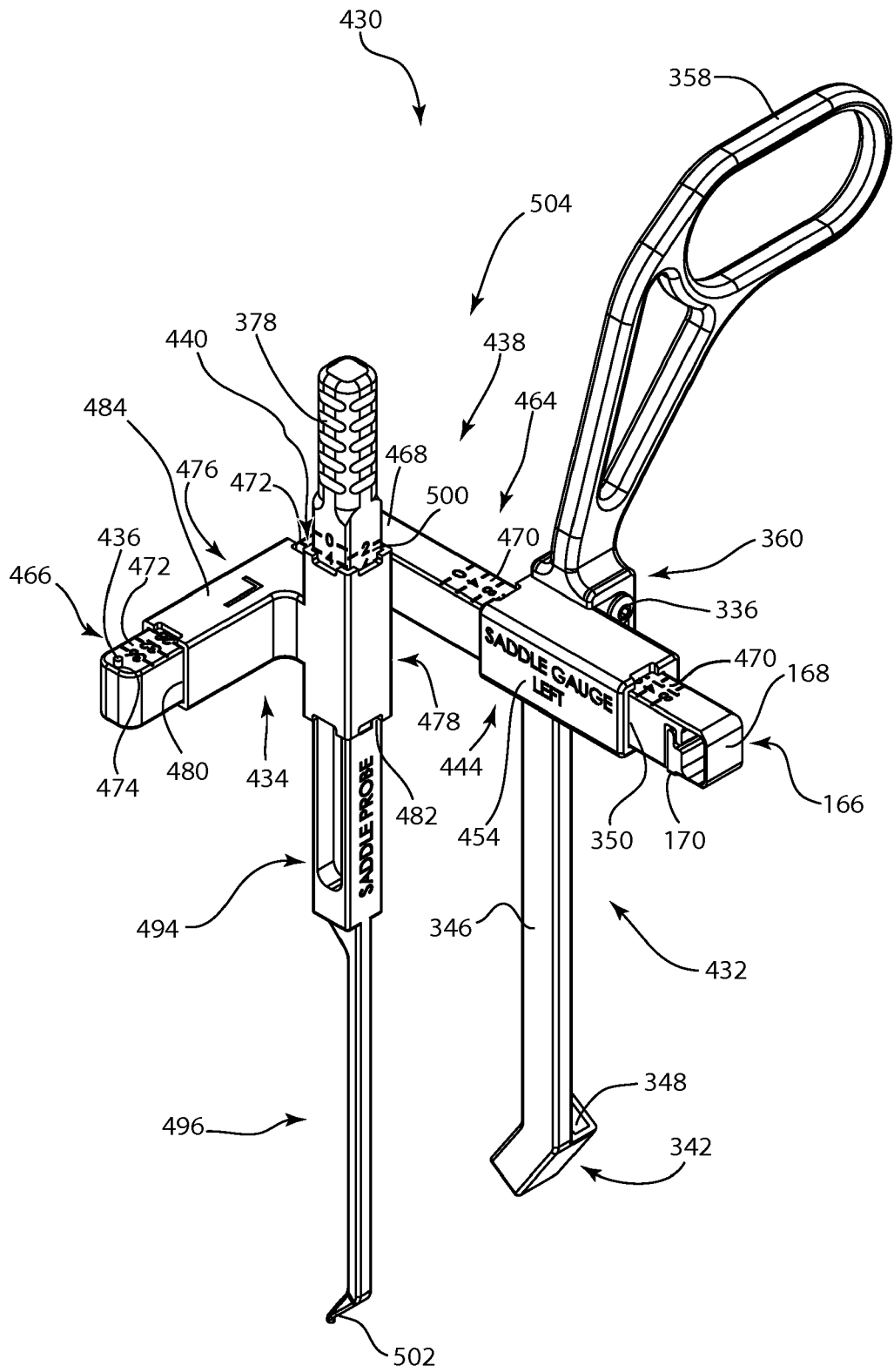
FIG. 11 is a perspective view of the pedicle measurement tool of FIG. 10, in a fully assembled state.

Referring to FIG. 11, a perspective view illustrates the pedicle measurement tool 430 in a fully assembled state. Once assembled, the registration member 432, slider member 434, rod member 438, and contact member 440 all combine to form a displacement structure 504 capable of permitting tri-axial variation in the relative positions of the registration interface 342 and the contact feature 502. More precisely, the first slider 444 and the first rod 464 cooperate to permit relative translation along one axis. The second slider 476 and the second rod 466 cooperate to permit relative translation along an axis perpendicular to that of the first slider 444 and the first rod 464. The third slider 478 and the third rod 494 cooperate to permit relative translation along an axis perpendicular to those of the first slider 444 and the first rod 464, and the second slider 476 and the second rod 466.

The registration member 432 is particular to the left-hand side, and a mirror image of the registration member 432 would be required for right-side measurement operations. However, the slider member 434, pin 436, rod member 438, and contact member 440 may be used for either left-hand side or right-hand side measurement. The slider member 434, pin 436, and rod member 438 may simply be rotated 180°, and the contact member 440 may be rotated 180° about a different axis, and then the slider member 434, pin 436, rod member 438, and contact member 440 may be reassembled to each other and to a right-hand registration member, handle member, and screw (not shown) to provide a pedicle measurement tool for the right-hand side.

Figure 12:
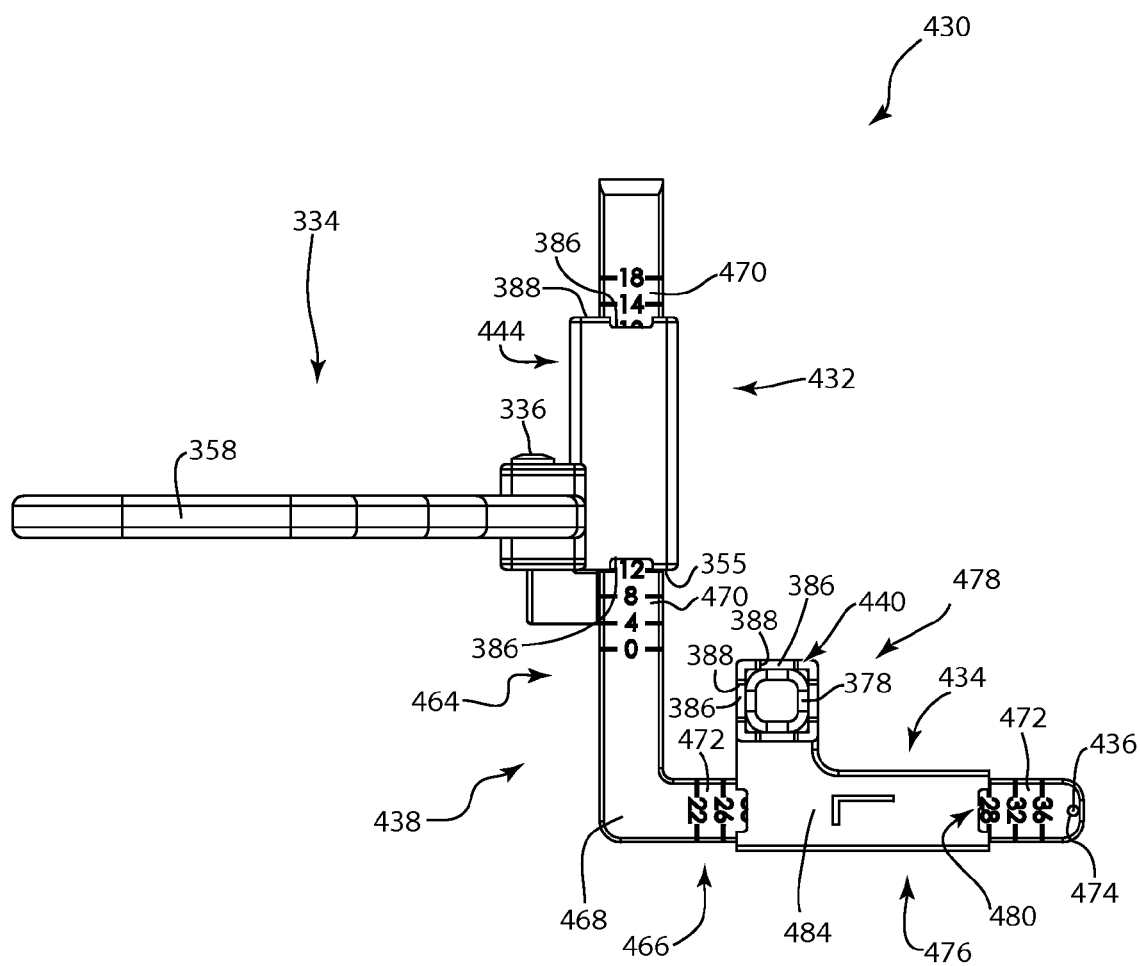
FIG. 12 is a plan view of the pedicle measurement tool of FIG. 10, in a fully assembled state.

Referring to FIG. 12, a plan view illustrates the pedicle measurement tool 430 in a fully assembled state. As shown, each of the first, second, and third sliders 444, 476, 478 has a plurality of recesses 386 positioned to facilitate reading of the markings 470, 472, 500 of the first, second, and third rods 464, 466, 494, respectively. Each of the sliders 444, 476, 478 also has measurement edges 388 that align with the tic marks adjacent to the numbers of the markings 470, 472, 500 so that a clear and unambiguous measurement reading may be obtained.

The recesses 386 and measurement edges 388 operate in the manner described previously, in connection with FIG. 9, to facilitate measurement. Furthermore, like the markings 368 of FIG. 9, each set of markings 470, 472 of the first and second rods 464, 466 of FIG. 12 is separated into two groupings to double the resolution of measurement along their respective axes by permitting measurements to be read from either end of the first and second sliders 444, 476. As more clearly illustrated in FIG. 11, the markings 500 of the third rod 494 may also be staggered between adjacent, perpendicular facets of the third rod 494 to provide a similar increase in resolution, as on the second rod 374 the facet measurement tool 330 of FIG. 8.

Figure 13:
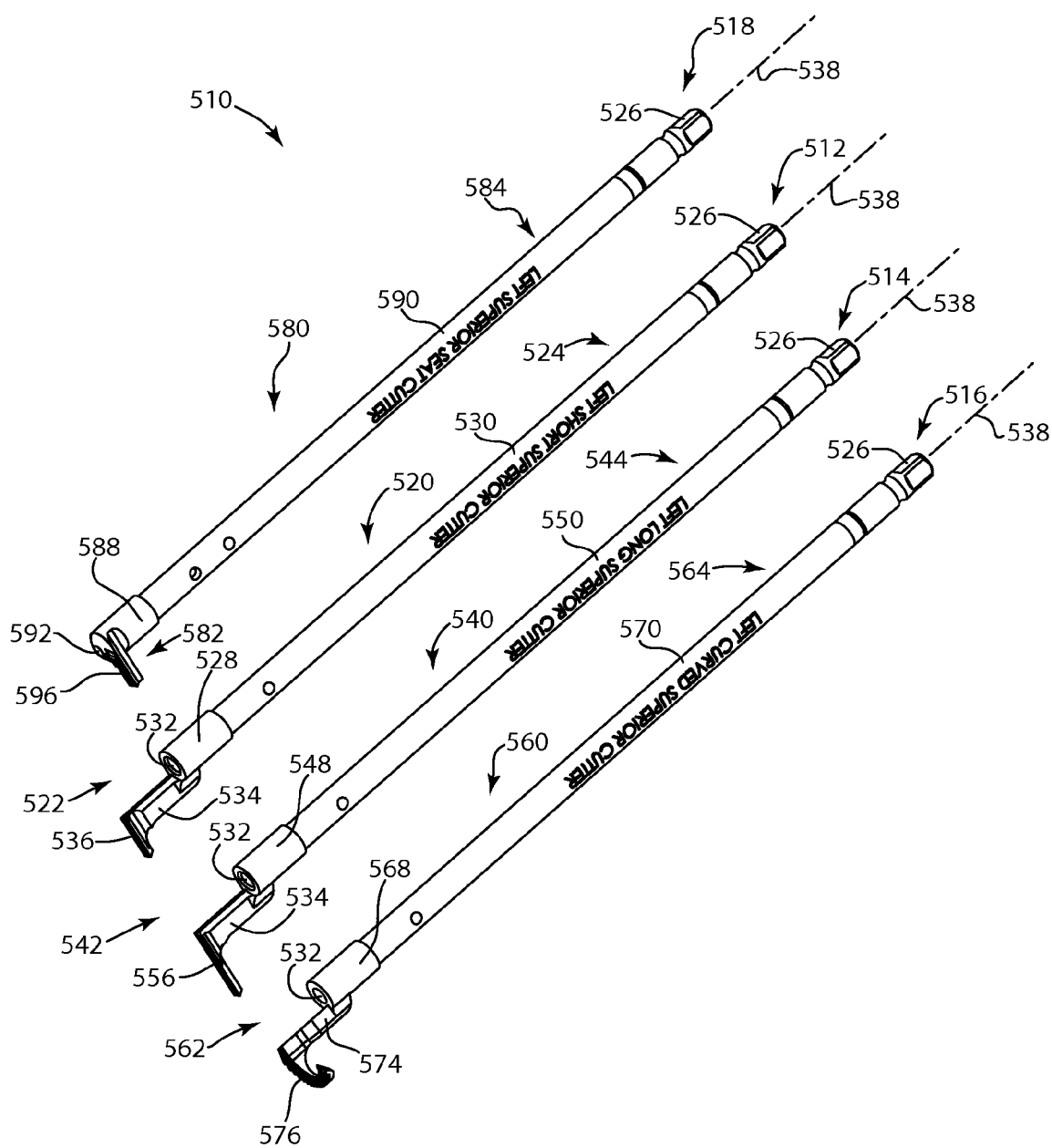
FIG. 13 is a perspective view of a short cutting tool, a long cutting tool, a curved cutting tool, and a seat cutting tool, all of which are designed to resect a superior facet of the spinal column.

Referring to FIG. 13, a perspective view illustrates a kit 510 of cutting tools designed to resect the superior facets 38 of the first vertebra 24. The kit 510 includes a short cutting tool 512, a long cutting tool 514, a curved cutting tool 516, and a seat cutting tool 518. Each of the cutting tools 512, 514, 516, 518 is registrable to the spine 10 via a post or guide wire (not shown in FIG. 13) to guide rotation of the cutting tools 512, 514, 516, 518 to a fixed axis. The short cutting tool 512, the long cutting tool 514, and the curved cutting tool 516 cooperate to resect bone tissue from the superior facet 38 of the left-hand side of the first vertebra 24 to provide a substantially continuous, planar surface. The seat cutting tool 518 is usable to provide a planar surface relatively nearer the saddle point 42 of the pedicle 30 of the left-hand side of the first vertebra 24. The manner in which the kit 510 is used will be shown and described in greater detail subsequently.

As illustrated in FIG. 13, the short cutting tool 512 has a shaft 520 and a resection feature 522 protruding asymmetrically from the shaft 520. The shaft 520 receives oscillating torque, which is then transmitted to the resection feature 522 to remove bone tissue as the resection feature 522 oscillates against the bone tissue. The shaft 520 has a central portion 524, a torque receiver 526, and a distal cap 528. In alternative embodiments, a shaft 520 of a superior cutting tool (not shown) need not have a circular cross section, and need not be used for rotation. Rather, such a shaft may be used to drive linear motion to provide resection of a bony landmark. Such translational superior cutting tools are envisioned by the present invention.

The central portion 524 has an indicator 530 that indicates the identity and intended use of the short cutting tool 512, i.e., resection of the superior facet 38 of the left-hand side of the first vertebra 24. The torque receiver 526 is shaped to receive a torque transmitting implement such as a manually grippable handle or a coupling driven by a motor. The torque receiver 526 may have a hexagonal cross section or the like to permit transmission of torque when inserted into a corresponding hexagonal cavity of a driver (not shown in FIG. 13). Manual rotation of the cutting tools 512, 514, 516, 518 may provide greater control for purposes of superior facet resection. The shaft 520 further has a registration feature 532 that facilitates rotation about the desired stationary axis. The registration feature 532 will be shown and described in greater detail subsequently.

As illustrated in FIG. 13, the resection feature 522 is integrally formed with the distal cap 528 of the shaft 520. The resection feature 522 includes an arm 534 generally parallel to the shaft 520 and a cutting surface 536 that extends substantially perpendicular to the arm 534. The cutting surface 536 is shaped to form a substantially planar resection surface in response to oscillatory rotation about an axis of rotation 538 of the shaft 520. As shown, the resection feature 522 protrudes non-collinear to the axis of rotation 538. Thus, the resection feature 522 is not symmetrical about the axis of rotation 538. The resection feature 522 and the registration feature 532 will be shown and described in greater detail subsequently.

The long cutting tool 514 similarly has a shaft 540 and a resection feature 542 protruding from the shaft 540. The shaft 540 has a central portion 544, a torque receiver 526, and a distal cap 548. The central portion 544 has an indicator 550 that indicates the identity and intended use of the long cutting tool 514. The shaft 540 has a registration interface 532 that facilitates rotation about the desired stationary axis, i.e., the axis of rotation 538 of the shaft 540. The resection feature 542 is integrally formed with the distal cap 548 and has an arm 534 and a cutting surface 556 that extends substantially perpendicular to the arm 534. The cutting surface 556 is shaped to cooperate with the cutting surface 536 of the short cutting tool 512 to form the substantially planar resection surface.

The curved cutting tool 516 similarly has a shaft 560 and a resection feature 562 protruding from the shaft 560. The shaft 560 has a central portion 564, a torque receiver 526, and a distal cap 568. The central portion 564 has an indicator 570 that indicates the identity and intended use of the curved cutting tool 516. The shaft 560 has a registration interface 532 that facilitates rotation about the desired stationary axis, i.e., the axis of rotation 538 of the shaft 560. The resection feature 562 is integrally formed with the distal cap 568 and has an arm 534 and a cutting surface 576 that extends substantially perpendicular to the arm 534.

The cutting surface 576 is shaped to cooperate with the cutting surfaces 536, 556 of the short cutting tool 512 and the long cutting tool 514 to form the substantially planar resection surface. However, unlike the cutting surfaces 536, 556, the cutting surface 576 is generally arcuate in shape. The configuration of the cutting surface 576 will be shown and described in greater detail subsequently.

The seat cutting tool 518 also has a shaft 580 and a resection feature 582 protruding from the shaft 580. The shaft 580 has a central portion 584, a torque receiver 526, and a distal cap 588. The central portion 584 has an indicator 590 that indicates the identity and intended use of the seat cutting tool 518. The shaft 580 has a registration interface 592 that facilitates rotation about the desired stationary axis, i.e., the axis of rotation 538 of the shaft 580. The resection feature 582 is integrally formed with the distal cap 588 and has a cutting surface 596 that extends substantially perpendicular to the shaft 580. The seat cutting tool 518 may be registered differently from the cutting tools 512, 514, 516; therefore, the resection feature 582 does not require an arm 534 to displace the cutting surface 596 from the distal cap 588.

Figure 14:
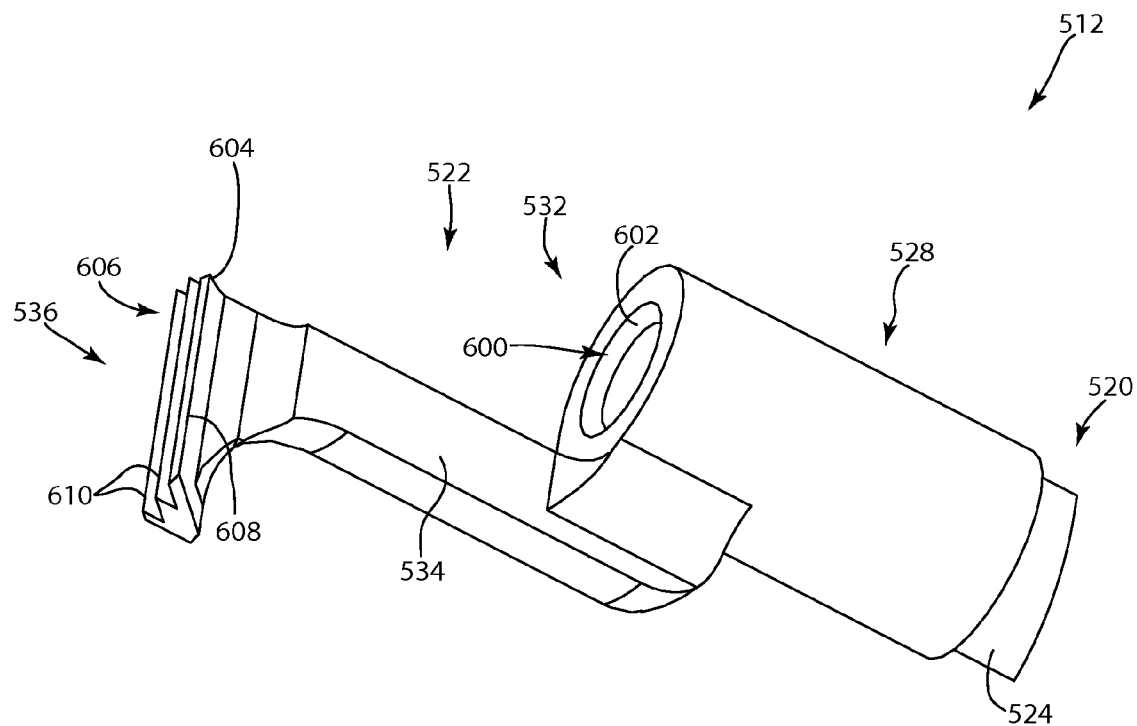
FIG. 14 is an enlarged, perspective view of one end of the resection feature of the short cutting tool of FIG. 13.

Referring to FIG. 14, an enlarged, perspective view illustrates the resection feature 522 and the corresponding end of the shaft 520 of the short cutting tool 512 in greater detail. As shown, the registration interface 532 has a bore 600 that passes through the distal cap 528 and into the remainder of the shaft 520 via an aperture 602 formed in the distal cap 528. Accordingly, the registration interface 532 is able to receive a stationary registration feature such as a cylindrical member to constrain rotation of the short cutting tool 512 to the axis of rotation 538 of the shaft 520.

As illustrated in FIG. 14, the cutting surface 536 has a leading edge 604 and a rasp portion 606 that trails behind the leading edge 604 when the cutting surface 536 moves clockwise about the axis of rotation 538, as viewed from the torque receiver 526. The leading edge 604 has a wedge 608 with an acute angle that enables the wedge 608 to split off and pry up bits of bone tissue. The rasp portion 606 has a plurality of abrasive features in the form of teeth 610 that abrade the bone surface to further remove bone tissue. The teeth 610 may also have sharpened edges that scrape against the bone as the rasp portion 606 follows the leading edge 604. If desired, the teeth 610 may vary slightly in length so that each tooth, removes progressively more bone.

The teeth 610 advantageously are oriented to cut substantially along only one direction of rotation of the short cutting tool 512, i.e., the direction moving away from the foramenal space of the first vertebra 24. Thus, the sensitive nerve roots that extend through the foramenal space are protected from abrasion by the relatively blunt, trailing edges of the teeth 610. In alternative embodiments, a rasp portion of a superior facet cutting tool may have teeth with various shapes to provide straight teeth, angled teeth, diamond-shaped teeth, or any other desirable tooth configuration.

The leading edge 604 and the rasp portion 606 provide two different types of cutting action that cooperate to enhance the efficiency of resection, as well as provide a relatively smooth resection surface. The short cutting tool 512 may be rotated by hand in an oscillatory manner about the axis of rotation 538 to form a portion of a resection surface that is generally bounded by a sector of a circle.

Figure 15:
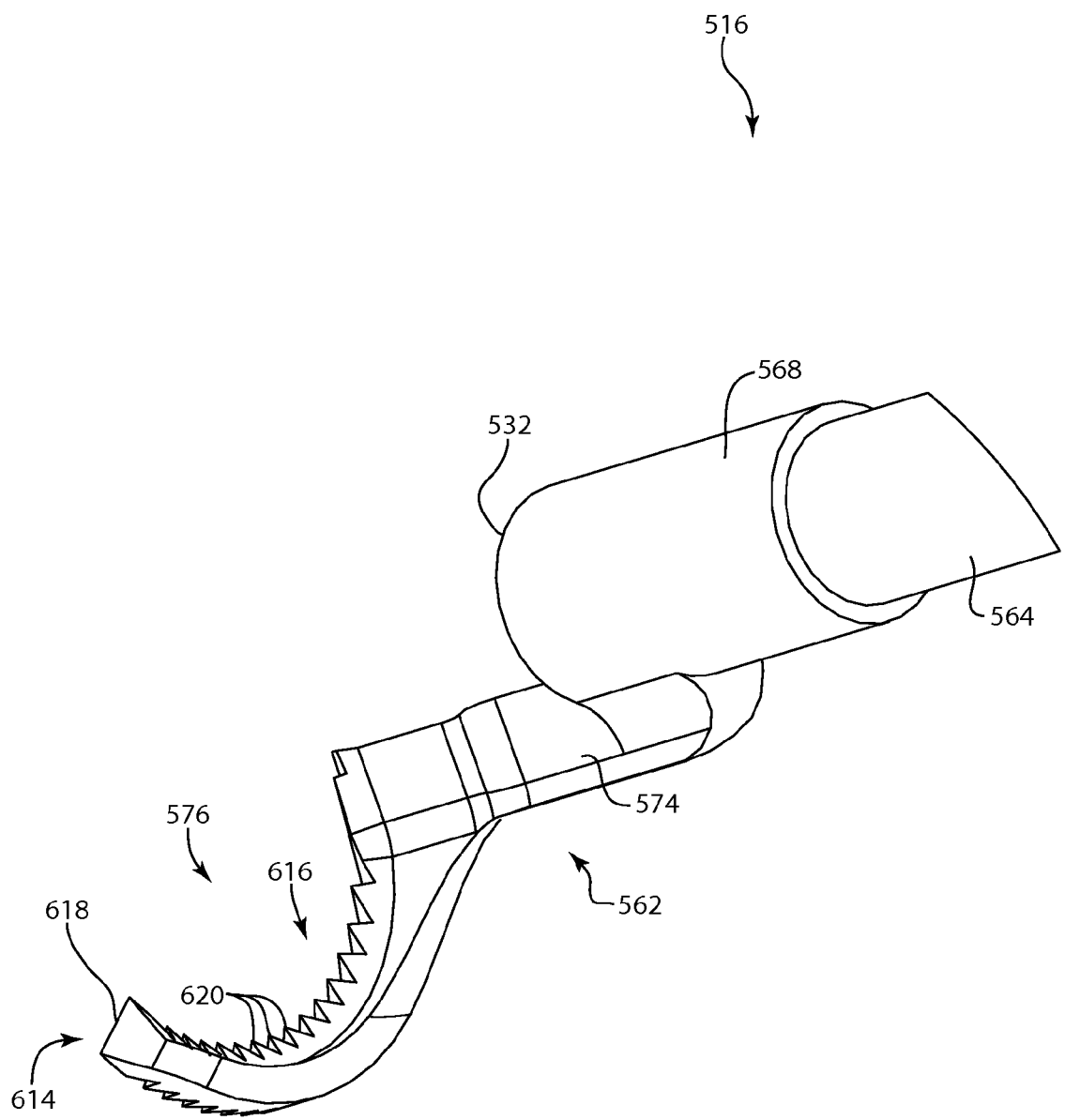
FIG. 15 is a perspective view of one end of the resection feature of the curved cutting tool of FIG. 13.

Referring to FIG. 15, an enlarged, perspective view illustrates the resection feature 562 and the corresponding end of the shaft 560 of the curved cutting tool 516 in greater detail. The registration interface 532 of the curved cutting tool 516 is not shown in detail in FIG. 15, but is substantially the same as that of the short cutting tool 512, as described in connection with FIG. 14. The curved, or generally arcuate, shape of the cutting surface 576 is more clearly illustrated in FIG. 15.

As in the short cutting tool 512, the cutting surface 576 of the curved cutting tool 516 has a leading edge 614 and a rasp portion 616 that trails behind the leading edge 614 when the cutting surface 576 moves clockwise about the axis of rotation 538, as viewed from the torque receiver 526. The leading edge 614 has a wedge 618 with an acute angle that enables the wedge 618 to split off and pry up bits of bone tissue. The rasp portion 616 has a plurality of abrasive features in the form of teeth 620 that abrade the bone surface to further remove bone tissue.

As in the cutting surface 536, the leading edge 614 and the rasp portion 616 of the cutting surface 576 provide two different types of cutting action that cooperate to enhance the efficiency of resection, as well as provide a relatively smooth resection surface. The curved cutting tool 516 may be rotated by hand in an oscillatory manner about the axis of rotation 538 to form a portion of a resection surface that is generally bounded by a skewed sector of a circle. The long cutting tool 514 and the curved cutting tool 516 may form progressively larger resections than the short cutting tool 512, and may thus be used in progressive combination to split the superior facet resection procedure into a plurality of relatively simple steps.

Figure 16:
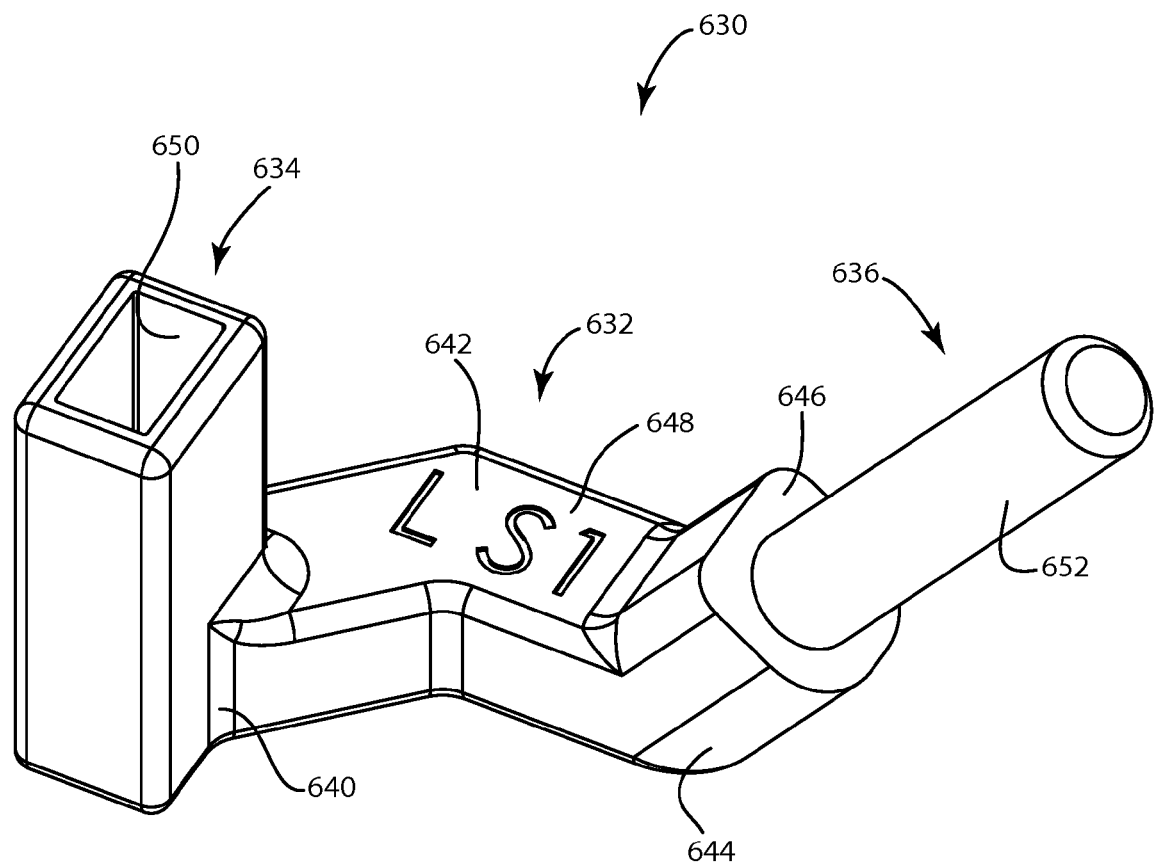
FIG. 16 is a perspective view of a cutting guide usable to couple the cutting tools of FIG. 13 to the frame of FIG. 4.

Referring to FIG. 16, a perspective view illustrates one embodiment of a cutting guide 630 usable to couple the short cutting tool 512, the long cutting tool 514, and the curved cutting tool 516 of FIG. 13 to the frame 110 of FIG. 4. As shown, the cutting guide 630 has a main body 632, a registration interface 634 designed to be registered on the frame 110, and a registration feature 636 designed to guide motion of the cutting tools 512, 514, 516.

The main body 632 may have a plurality of bends, including a first bend 640, a second bend 642, and a third bend 644 that provide the appropriate orientation of the registration feature 636 relative to the registration interface 634. The main body 632 also has a shoulder 646 adjoining the registration feature 636 to support the cutting tools 512, 514, 516, thereby controlling the depth of resection.

Further, the main body 632 has an indicator 648 that indicates the identity and intended use of the cutting guide 630, i.e., resection of the superior facet 38 on the left-hand side of the first vertebra 24. The indicator 648 further indicates that the cutting guide 630 corresponds to a specific implant, i.e., superior implant #1, which may be selected from a kit of several superior prostheses based on measurements made with the facet measurement tool 330 and/or the pedicle measurement tool 430. Generally, each prosthesis is selected based on which prosthesis of the kit most nearly resembles the natural facet to be replaced.

The registration interface 634 has a bore 650 with a generally rectangular shape selected to slide onto the guide post 124 of the first anchor 112 of the frame 110. The rectangular shape of the bore 650 and the guide post 124 then prevents relative rotation between the frame 110 and the cutting guide 630. The registration feature 636 has a post 652 with a generally circular cross section sized to slide into the bore 600 of any of the cutting tools 512, 514, 516. The post 652 may slide into the corresponding bore 600 until the corresponding distal cap 528, 548, 568 abuts the shoulder 646 of the main body 632. The shoulder 646 thus controls the depth of resection by determining the plane within which resection occurs.

Figure 17:
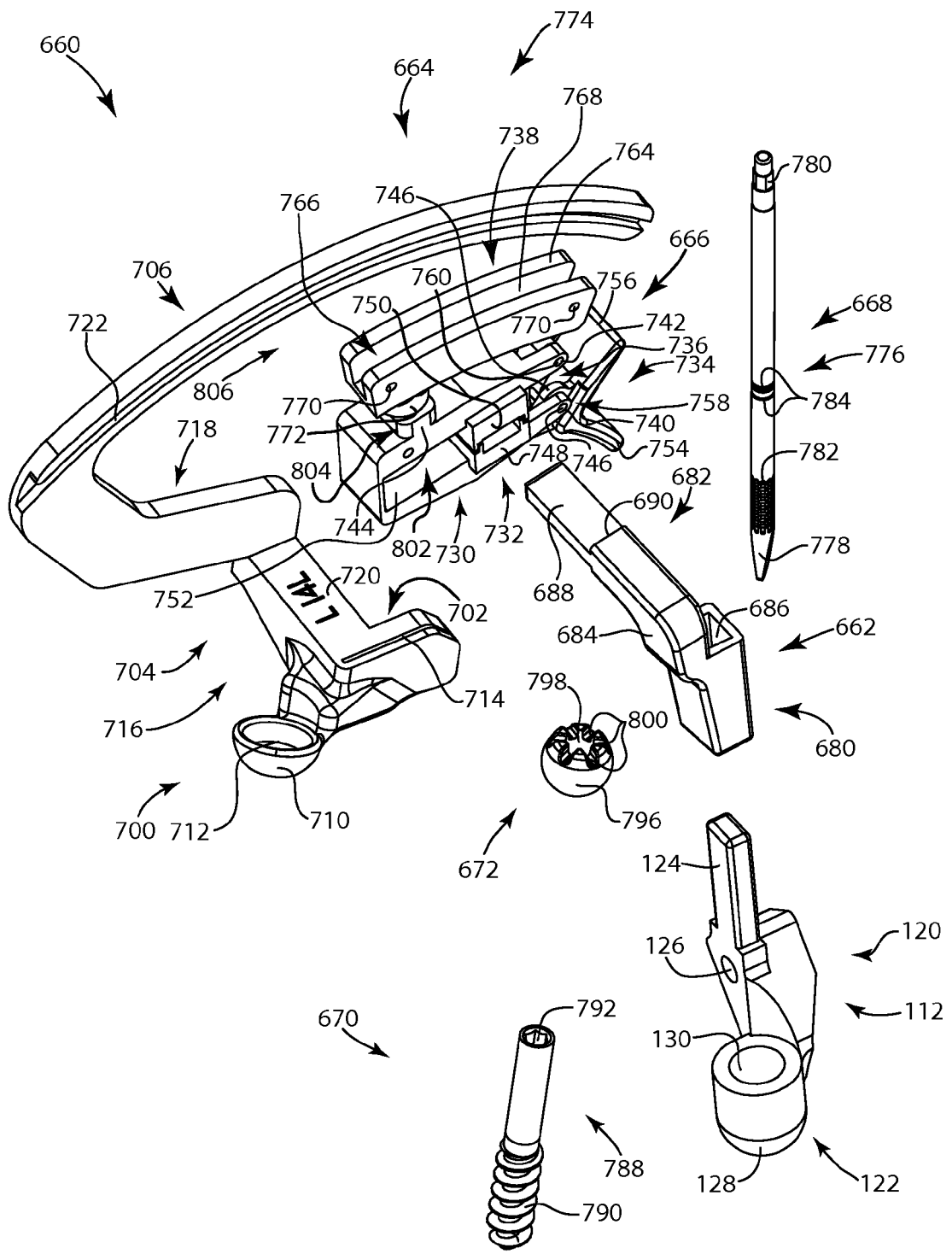
FIG. 17 is an exploded, perspective view of an inferior resection tool designed to guide resection of an inferior facet of the spinal column, as well as a guide wire, pedicle screw, and castle nut.

Referring to FIG. 17, an exploded, perspective view illustrates an inferior resection tool 660 according to one embodiment of the invention. The inferior resection tool 660 may be used to resect the inferior facet 60 of the left-hand side of the second vertebra 26. As will be described in greater detail subsequently, the inferior resection tool 660 remotely simulates the tangential contact between members of a ball-and-trough joint such as the facet joints 64 of the spine 10, or a replacement facet joint designed to mimic the articulation of the facet joints 64.

As shown, the inferior resection tool 660 has a registration member 662, an anchoring member 664, and a pivot member 666. A guide wire 668, a pedicle screw 670, and a castle nut 672 may be used in conjunction with the registration member 662 and the anchoring member 664, and are therefore depicted in FIG. 17, in addition to the first anchor 112 illustrated previously in FIGS. 4 and 5.

The registration member 662 has a registration interface 680 designed to register the inferior resection tool 660 on the frame 110 of FIG. 4. Additionally, the registration member 662 has a first arm 682 coupled to the registration interface 680 at a bend 684. The registration interface 680 has a bore 686 with a generally rectangular cross section shaped to receive the guide post 124 of the first anchor 112 of the frame 110 in such a manner that the registration member 662 is unable to rotate with respect to the frame 110. The bend 684 positions the first arm 682 at a desired orientation with respect to the registration interface 680. The first arm 682 has an extension 688 with a relatively narrower cross section and a shoulder 690 that controls the depth of insertion of the extension 688 into the pivot member 666.

As shown, the anchoring member 664 has an anchoring feature 700, a guide feature 702, a second arm 704, and an arcuate extension 706. The anchoring feature 700 is shaped to abut the left-side saddle point 62 of the second vertebra 26 in such a manner that the anchoring member 664 is able to rotate against the second vertebra 26 until locked in place via the castle nut 672. The anchoring feature 700 has a semispherical surface that permits relative rotation between the anchoring member 664 and the second vertebra 26 along three orthogonal axes. The anchoring feature also has a bore 712 through which the pedicle 670 may extend. The semispherical surface 700 corresponds to a semispherical surface of an inferior prosthesis so that motion of the anchoring feature 700 against the bone mimics positioning of the corresponding inferior prosthesis.

The guide feature 702 has a slot 714 positioned to guide a cutting tool, such as a blade of an oscillating saw designed for cutting bone. The second arm 704 has a first portion 716 and a second portion 718 extending from the first portion 716 at an angle. The second arm 704 also has an indicator 720 that indicates the identity and intended use of the second arm 704, i.e., resection of the left-side facet 60 of the second vertebra 24.

The indicator 720 further indicates that the anchoring member 664 corresponds to a specific implant, i.e., inferior implant #4 "long," which may be selected from a kit of several inferior implants based on measurements made with the facet measurement tool 330 and/or the pedicle measurement tool 430. The registration member 662 may similarly correspond to a specific superior implant, and may have an indicator (not shown) that indicates which implant of a kit of multiple implants the registration member 662 corresponds to.

The arcuate extension 706 has a generally arcuate shape designed to cooperate with the pivot member 666 to provide a rotary joint. The arcuate extension 706 has a groove 722 that extends along its length to interface with the pivot member 666.

The pivot member 666 has a main body 730, a retention interface 732, a lever 734, a plate 736, and an engagement interface 738. The main body 730 has a generally U-shaped configuration with a first pair of apertures 740 and a second pair of apertures 742. The first pair of apertures 742 pivotably engages the lever 734. The second pair of apertures 742 pivotably engages the plate 736. The main body 730 also has a plateau 744 that pivotably engages the engagement interface 738.

The plate 736 has a pair of pins 746 that extend into the second pair of apertures 742 of the main body 730 such that the plate 736 is rotatable relative to the main body 730 about an axis passing through the pins 746. The retention interface 732 has a first bracket 748 with a generally U-shaped configuration and a second bracket 750 that also has a generally U-shaped configuration and is positioned in opposition to the first bracket 748 so that the extension 688 of the first arm 682 can be retained between the brackets 748, 750. The first and second brackets 748, 750 are positioned within a slot 752 defined by the shape of the main body 730. The retention interface 732 is able to slide along the slot 752 until the lever 734 is actuated to lock the extension 688 and the retention interface 732 in place.

The lever 734 has a grip plate 754 and a detent plate 756 that are positioned at near-ninety degree angles to each other. The grip plate 754 is positioned to be grasped and manually moved by a user to move the lever 734 between locked and unlocked positions. The detent plate 756 is positioned to abut the main body 730 to limit rotation of the lever 734. A pivot extension 758 extends from the detent plate 756 and includes a pair of flanges 760, only one of which is visible in FIG. 17. The flanges 760 are pivotably attached to the first pair of apertures 740 such that the lever 734 rotates about an axis passing through the first pair of apertures 740. The flanges 760 are also pivotably coupled to the plate 736 at a point-of-attachment that is not visible in FIG. 17, but is proximate the juncture of the grip plate 754 to the detent plate 756.

In FIG. 17, the lever 734 is in an unlocked position, in which the main body 730 is not compressed and therefore, the first and second brackets 748, 750 of the retention interface 732 are movable along the slot 752 and may be separated sufficiently to permit insertion of the extension 688 of the first arm 682 into the space between the first and second brackets 748, 750. When the lever 734 is pivoted such that the detent plate 756 abuts the end of the main body 730, the plate 736 is drawn by the flanges 760 such that the second pair of apertures 742 of the main body 730 is drawn toward the first pair of apertures 740. As a result, the slot 752 is compressed and the brackets 748, 750 of the retention interface 732 are pressed against each other. The brackets 748, 750 are then unable to slide along the slot 752 and the extension 688 of the first arm 682 is unable to slide within the compressed space between the brackets 748, 750.

The location of the pivotable coupling of the plate 736 to the flanges 760 provides an over-center geometry that makes the lever 734 "bi-stable." This over-center geometry is present because the point-of-attachment of the plate 736 to the flanges 760 passes through a plane extending through the first and second pairs of apertures 740, 742 in the course of motion of the lever 734 between the locked and unlocked positions. Thus, the lever 734 is able to rest in either of the locked and unlocked positions until actuated by a user. The lever 734 therefore provides a quick-release and quick-locking mechanism by which the first arm 682 can be locked in engagement with the pivot member 666.

The engagement interface 738 has a first plate 764 and a second plate 766, each of which has a generally arcuate shape with a radius substantially the same as that of the arcuate extension 706 of the anchoring member 664. The plates 764, 766 are positioned substantially parallel to each other such that a trough 768 is defined between them. The trough 768 is sized such that the arcuate extension 706 is able to slide along the trough 768 with clearance.

The second plate 766 has a pair of pins 770 that extend into the trough 768 to protrude into the groove 722 of the arcuate extension 706 to restrict motion of the engagement interface 738 perpendicular to the arcuate extension 706. Thus, the engagement interface 738 is constrained to follow the arcuate pathway of the arcuate extension 706. The engagement interface 738 also has a collar 772 that is rotatably coupled to the plateau 744 of the main body 730 to permit rotation of the engagement interface 738 with respect to the main body 730.

The registration member 662, the anchoring member 664, and the pivot member 666 may be coupled together to define a linking structure 774 that couples the registration interface 680 of the registration member 662 with the anchoring feature 700 of the anchoring member 664. The linking structure 774 facilitates proper positioning of the slot 714 of the guide feature 702 of the anchoring member 664 in a manner that will be described subsequently.

As also shown in FIG. 17, the guide wire 668 has a central portion 776, a leading end 778, and a trailing interface 780. The leading end 778 is sharpened to facilitate bone penetration, and the trailing interface 780 may have a hexagonal or other cross sectional shape selected to permit connection of the trailing interface 780 with a driver (not shown in FIG. 17). The central portion 776 has a roughened portion 782 proximate the leading end 778, and a pair of markings 784 positioned near the center of the central portion 776.

The roughened portion 782, when exposed, may indicate that the guide wire 668 has not been driven sufficiently far into the pedicle (for example, one of the pedicles 30 of the first vertebra 24 or one of the pedicles 50 of the second vertebra 26). The markings 784 indicate proper implantation of the guide wire 668 into a pedicle when only one of the markings 784 is visible, and the other is beneath the surface of the bone.

As depicted in FIG. 17, the pedicle screw 670 has a shank 788, which may have machine threads (not shown) designed to receive the castle nut 672, and a threaded end 790 with threads shaped to retain the pedicle screw 670 firmly in bone. The pedicle screw 670 also has a torque receiver 792 designed to receive torque from a manual or motorized driver. The torque receiver 792 has a cavity with a generally hexagonal cross sectional shape selected to receive the end of a driver with a corresponding hexagonal shape.

The castle nut 672 has a semispherical surface 796 designed to rest against the concave semispherical surface within the anchoring feature 700. The castle nut 672 also has a bore 798 through which the shank 788 of the pedicle screw 670 may pass, and a plurality of radial grooves 800 that facilitate transmission of torque to the castle nut 672 from a manual or motorized driver. The semispherical surface 796 permits rotation of the anchoring feature 700 against the bone until the castle nut 672 is tightened to sandwich the anchoring feature 700 between the bone and the castle nut 672.

As mentioned previously, the inferior resection tool 660, or more precisely, the linking structure 774, remotely mimics the tangential contact between articulating surfaces of a natural facet joint, and the articulation of a corresponding prosthetic facet joint, by providing ball-in-trough motion. More precisely, the linking structure 774 provides a first joint 802, a second joint 804, and a third joint 806. The first joint 802 is a linear joint, and the second and third joints 804, 806 are rotary joints. The configuration and operation of the joints 802, 804, 806 will be described in greater detail in connection with FIG. 18.

The registration feature 662, the anchoring member 664, and the pivot member 666 may easily be assembled to provide the inferior resection tool 660. According to one method of assembly, the anchoring member 664 and the pivot member 666 may first be coupled together by inserting the arcuate extension 706 through the trough 768 of the engagement interface 738 such that the pins 770 extend into the groove 722. Then, with the lever 734 in the unlocked position, as shown in FIG. 17, the extension 688 of the first arm 682 may be inserted into the space between the first and second brackets 748, 750 of the retention interface 732 until the shoulder 690 of the first arm 682 abuts the brackets 748, 750.

As mentioned previously, moving the lever 734 to the locked position locks the extension 688 in place between the first and second brackets 748, 750 and also prevents further translation of the retention interface 732 along the slot 752 of the main body 730. Motion of the retention interface 732 along the slot 752 may be required in order to couple the registration member 662 and the anchoring member 664 to the first vertebra 24 and the second vertebra 26, respectively, at their proper relative orientations. Accordingly, the lever 734 may be left in the unlocked position until attachment of the inferior resection tool 660 to the spine 10, or may be moved to the locked position during assembly and then moved back to the unlocked position prior to attachment to the spine 10.

Figure 18:
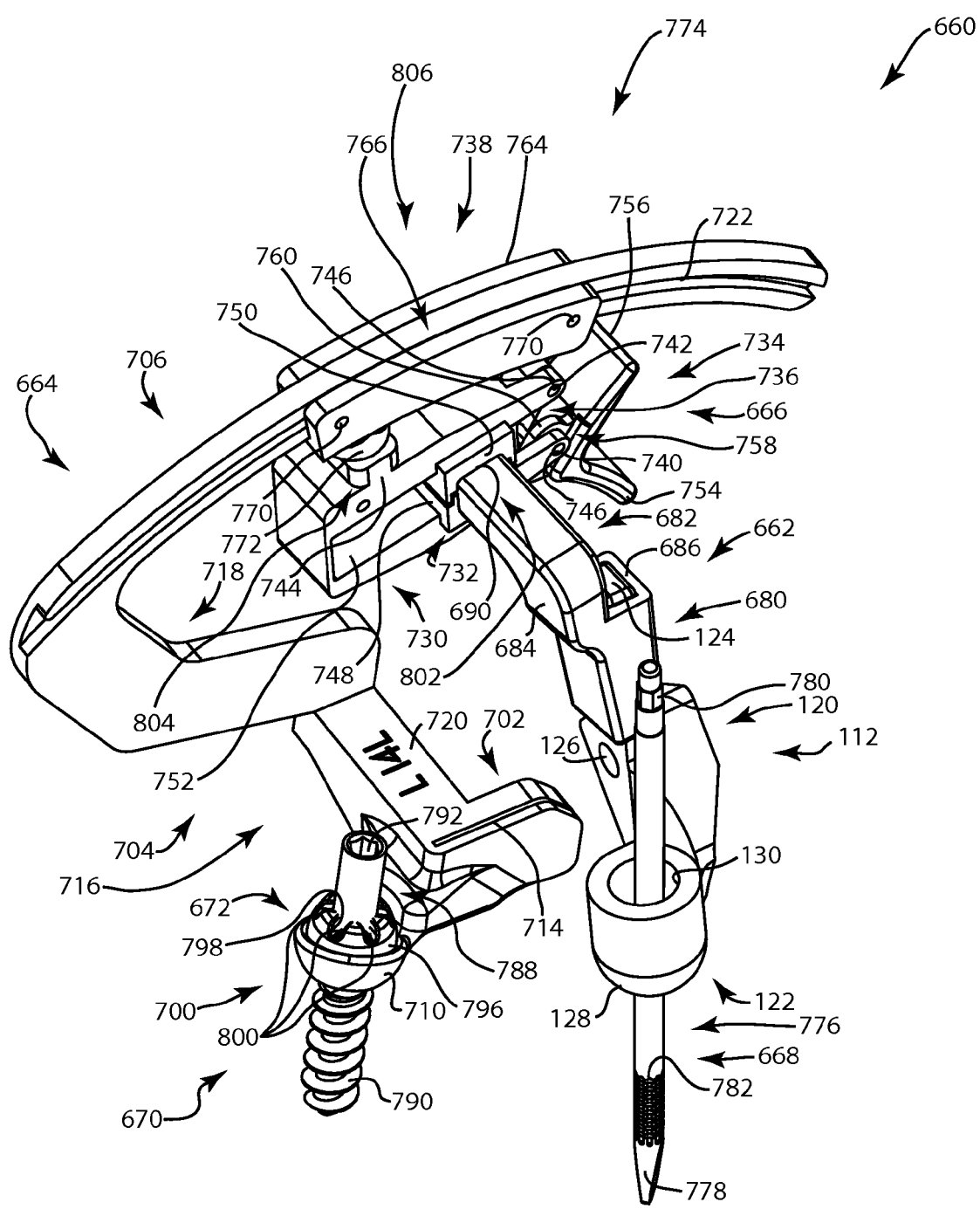
FIG. 18 is a perspective view of the inferior resection tool of FIG. 17, in a fully assembled state.

Referring to FIG. 18, a perspective view illustrates the inferior cutting tool 660 in a fully assembled configuration. The first anchor 112, the guide wire 668, the pedicle screw 670, and the castle nut 672 are also shown in their proper positions to couple the inferior cutting tool 660 to the spine 10 (not shown in FIG. 18).

More precisely, the guide wire 668 is positioned as though implanted in the left-side pedicle 30 of the first vertebra 24, and the first anchor 112 is positioned such that the guide wire 668 passes through the bore 130 of the anchoring feature 122 of the first anchor 112 to keep the first anchor 112 properly positioned with respect to the pedicle 30. The guide post 124 of the first anchor 112 is inserted through the bore 686 of the registration interface 680 such that the registration interface 680 is registered on the first anchor 112. The pedicle screw 670 is positioned as though implanted in the left-side pedicle 50 of the second vertebra 26, and the anchoring feature 700 is placed such that the shank 788 of the pedicle screw 670 passes through the bore 712 of the anchoring feature 700. The castle nut 672 is threaded into engagement with the threaded end 690 of the pedicle screw 670 to keep the anchoring feature 700 in place against the pedicle 50.

The first, second, and third joints 802, 804, 806 of the inferior resection tool 660 enable adjustment of the relative positions and orientations of the anchoring feature 700 and the registration interface 680. As the relative orientations are adjusted, the anchoring member 664 will pivot about the center of the semispherical surface 710 of the anchoring feature 700 to the proper orientation to position the slot 714 at the desired orientation for proper resection of the inferior facet 60 of the left-hand side of the second vertebra 26.

The first joint 802 includes the main body 730 and the retention interface 732 of the pivot member 666. The first joint 802 simulates sliding of a ball within a trough by enabling linear motion of the registration interface 680 with respect to the anchoring feature 700 via translation of the retention interface 732 within the slot 752 of the main body 730. The first joint 802 permits adjustment to account for variations in the spacing between the pedicles 30, 50 of the first and second vertebrae 24, 26, respectively, generally along the cephalad and caudal directions 12, 14.

The second joint 804 includes the main body 730 and the engagement interface 738 of the pivot member 666. Rotation of the engagement interface 738 with respect to the main body 730 simulates rolling of a ball across a trough by enabling rotation of the registration interface 680 with respect to the anchoring feature 700. The second joint 804 permits adjustment to account for variations in the spacing between the pedicles 30, 50 of the first and second vertebrae 24, 26, respectively, generally along the medial/lateral axis 20.

The third joint 806 includes the engagement interface 738 of the pivot member 666 and the arcuate extension 706 of the anchoring member 664. The third joint 806 simulates rolling of a ball along a trough by enabling rotation of the registration interface 680 with respect to the anchoring feature 700 via rotation of the engagement interface 738 as it moves along the arcuate path of the arcuate extension 706. The third joint 806 permits adjustment to account for variations in the spacing between the pedicles 30, 50 of the first and second vertebrae 24, 26, respectively, generally along the anterior and posterior directions 16, 18.

As stated above, motion of the first, second, and third joints 802, 804, 806 accounts for positional variation generally along the cephalad and caudal directions 12, 14, the medial/lateral axis 20, and the anterior and posterior directions 16, 18, respectively. However, the joints 802, 804, 806 do not correspond directly to the various directions and axes 12, 14, 16, 18, 20 because the inferior resection tool 660 is positioned with respect to a coordinate system aligned with the axis of the pedicle 50 of the left-hand side of the second vertebra 26, and not necessarily with the sagittal plane 22. In any case, the joints 802, 804, 806 cooperate to adjust for a wide range of relative prosthesis positions and anatomical variations.

The first joint 802 remotely replicates the tangential contact between articulating surfaces of a facet joint because the retention interface 732 slides along an axis generally parallel to the trough defined by the superior facet 38 on the left-hand side of the first vertebra 24. The second and third joints 804, 806 remotely replicate the tangential contact between articulating surfaces of a facet joint because the second and third joints 804, 806 provide for relative rotation about axes that pass through the center of a semispherical surface (not shown in FIG. 17) of an inferior facet, such as the inferior facet 60 on the left-hand side of the second vertebra 26. Thus, the joints 802, 804, 806 cooperate to position the slot 714 of the guide feature 702 at the proper orientation to guide resection of the inferior facet 60 of the left-hand side of the second vertebra 26 so that the selected inferior prosthesis (not shown in FIG. 18) can be attached to the second vertebra 26 to replace the inferior facet 60.

In alternative embodiments, a fourth joint (not shown) may be added to the configuration of FIG. 18. More precisely, in place of the generally straight extension 688 of the first arm 682 more clearly illustrated in FIG. 16, a second arcuate extension (not shown) may be provided. Like the arcuate extension 706, the second arcuate extension may be centered about an axis passing through the center of curvature of the articulation surface of an inferior implant to be coupled to the saddle point 62 of the left-hand side of the second vertebra 26. The second arcuate extension may be insertable into the retention interface 732 such that the retention interface 732 is positionable at a plurality of locations along the length of the second arcuate extension to provide one more rotational degree of freedom. Moving the lever 734 to the locked position then locks the position of the retention interface 732 along the second arcuate extension.

Figure 19:
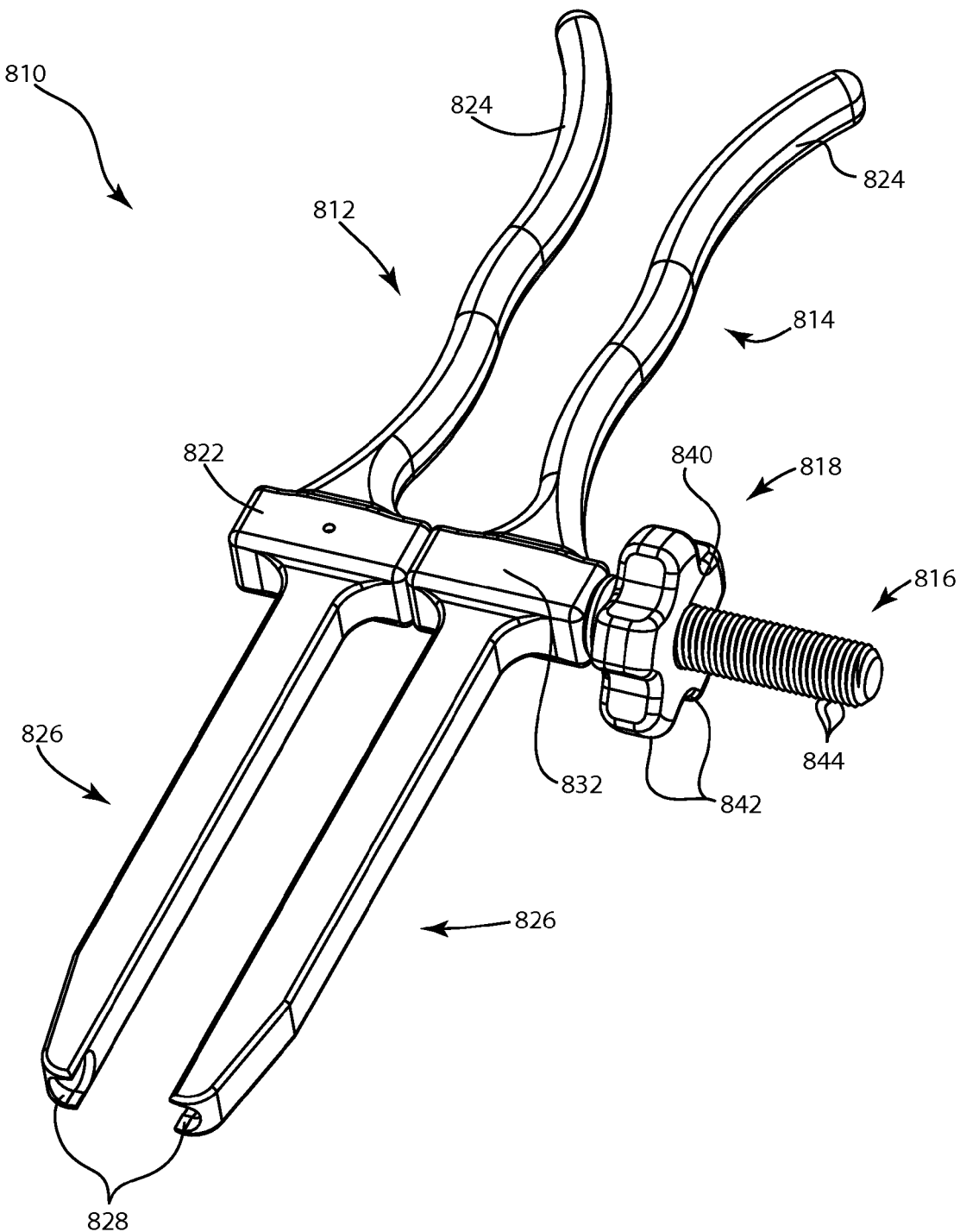
FIG. 19 is a perspective view of a clamping tool that facilitates attachment of inferior facet prostheses to the spinal column.

Referring to FIG. 19, a perspective view illustrates a clamping tool 810 according to one embodiment of the invention. The clamping tool 810 is used to hold the prostheses that replace the inferior facets 60 of the second vertebra 26 in place as they are securely attached. The manner in which the clamping tool 810 accomplishes this function will be described in greater detail subsequently.

As shown, the clamping tool 810 has a first clamping member 812, a second clamping member 814, a threaded post 816, and a knob 818. The first clamping member 812 has a main body 822, a handle portion 824 extending from one end of the main body 822, and a grip portion 826 extending from the other end of the main body 822. The grip portion 826 has a recess 828 proximate a free end of the grip portion 826 to receive and exert clamping force on a projection extending from an inferior facet prosthesis (not shown).

The second clamping member 814 is shaped to be a substantial mirror image of the first clamping member 812. Accordingly, the second clamping member 814 has a main body 832, a handle portion 824 extending from one end of the main body 832, and a grip portion 826 extending from the other end of the main body 832. Like the grip portion 826 of the first clamping member 812, the grip portion 826 of the second clamping member 814 has a recess 828 proximate a free end thereof to receive and exert clamping force on projection extending from an inferior facet prosthesis.

The threaded post 816 is integrally formed with or securely attached to the main body 822 of the first clamping member 812, and extends through the main body 832 of the second clamping member 814. The threaded post 816 further passes through and engages a threaded hole 840 of the knob 818. The knob 818 has a plurality of ridges 842 that facilitate gripping and rotation of the knob 818 by hand. The threaded post 816 has threads 844 that engage the threaded hole 840 and enable the knob 818 to advance along the threaded post 816 to press the first and second clamping members 812, 814 together in response to rotation of the knob 818. The operation of the clamping tool 810 will be shown and described in greater detail subsequently.

The various implements described in connection with FIGS. 1-19 may be used to facilitate measurement and resection of spinal bony landmarks and replacement of facets such as the superior facets 38 of the first vertebra 24 and the inferior facets 60 of the second vertebra 26. FIGS. 20-48 set forth one exemplary method for carrying out facet joint replacement according to the invention. However, a wide variety of methods may be used, and the structures of the present invention are not limited to use in any one method. Similarly, methods according to the invention may be carried out using structures different from those of FIGS. 1-19.

The method of FIGS. 20-48 will be set forth in connection with a bi-lateral facet joint replacement, or an operation in which both of the superior facets 38 of the first vertebra 24 and both of the inferior facets 60 of the second vertebra 26 are replaced. Those of skill in the art will recognize that the systems and methods of the present invention are also applicable to unilateral facet replacements, and operations in which only one facet of a facet joint is replaced such that the facet prosthesis articulates against a natural facet.

Some of the implements of FIGS. 1-19, including the reamers 70, 72, the frame 110, the stationary external support 260, and the clamping tool 810, may be usable to carry out operations on either side of the sagittal plane 22, i.e., on either of the left and right sides of the spine 10. However, some of the implements of FIGS. 1-19, including the facet measurement tool 330, the pedicle measurement tool 430, the kit 510 of superior cutting tools, the cutting guide 630, and the inferior resection tool 660, are specific to the left-hand side of the spine 10. The corresponding surgical instruments for the right-hand side may be substantial mirror images of the foregoing.

The method outlined below will generally describe procedures to be carried out with respect to the left-hand side of the spine 10, with the understanding that those of the right-hand side may be performed in a similar manner using the appropriate surgical instruments for the right-hand side. In some of FIGS. 20-48, the operations described in connection with the left-hand side have already been carried out on the right-hand side, so that the manner in which the operation is performed is shown in on the left-hand side, and the results of the operation are illustrated on the right-hand side.

The method may commence with performance of a CT scan of the patient to get the best possible mapping of the morphology of the spine 10. From the mapping, various dimensions may be obtained and used to preliminarily determine the appropriate prostheses to replace the superior facets 38 of the first vertebra 24 and the inferior facets 60 of the second vertebra 26. The prostheses may be selected from a kit of superior implant prostheses and a kit of inferior implant prostheses, each of which includes a plurality of prostheses varied in shape and size to provide compatibility with the vast majority of spinal morphologies.

Once the appropriate superior and inferior implant prostheses have been selected, blunt dissection and retraction of the tissues surrounding the first and second vertebrae 24, 26 may be carried out. The tissues are retracted to expose the vertebrae 24, 26, and also a portion of a third vertebra (not shown) adjacent to the second vertebra 26 and a portion of the sacrum (also not shown), which is adjacent to the first vertebra 24. The facet joints 64, pedicles 30, 50, and transverse processes 34, 54 of the first and second vertebrae 24, 26 are then identified. If needed, the facet joints 64 may be exposed by removing hypertrophic bone. The capsules that normally encase the facet joints 64 are then removed to expose the bony surfaces of the facet joints 64.

Figure 20:
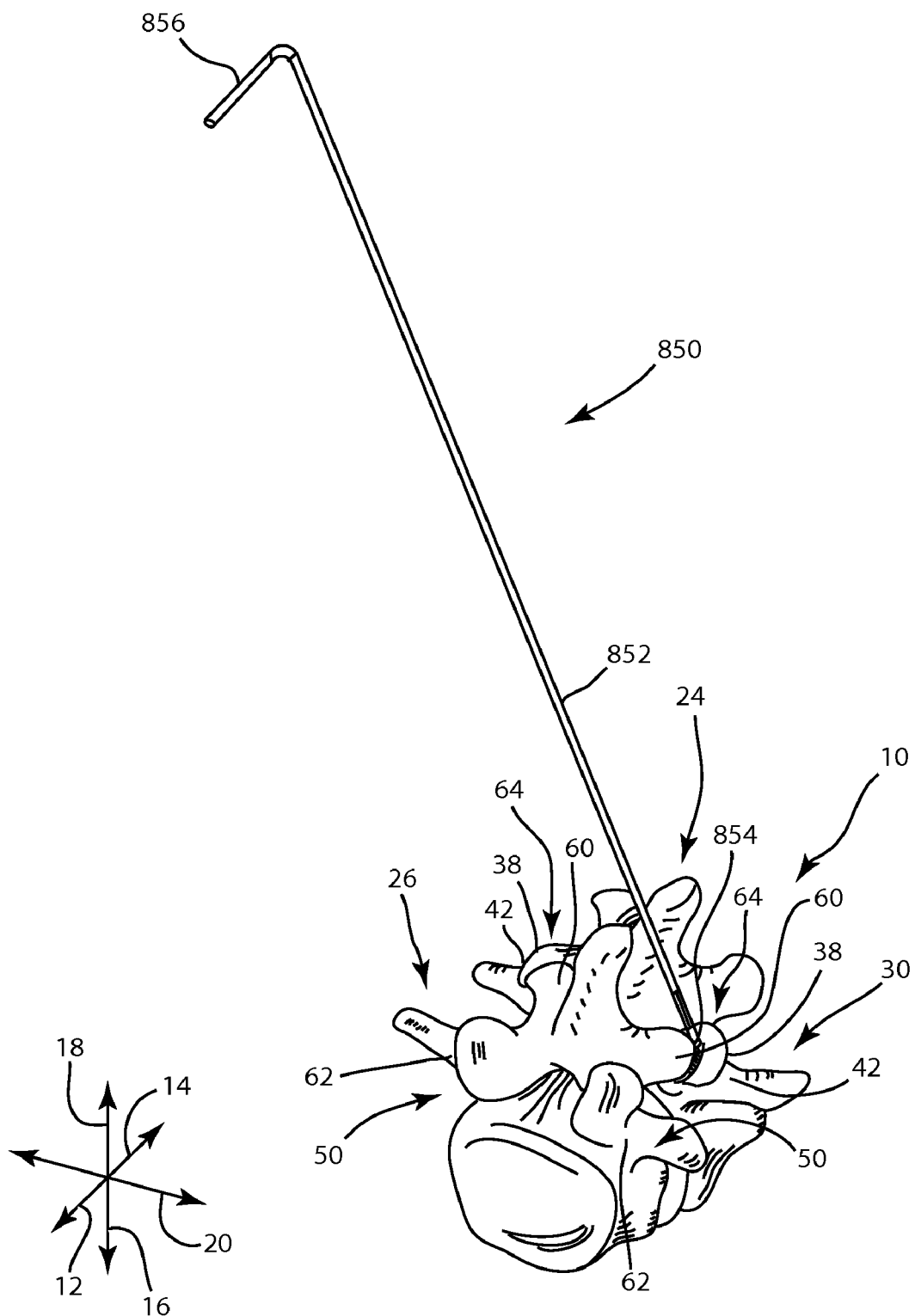
FIG. 20 is a perspective view of the L4 and L5 vertebrae of the spinal column of FIG. 1 with an insertion plate of a joint flag inserted between the facets of the facet joint.

Referring to FIG. 20, a perspective view illustrates the first and second vertebrae 24, 26 of the spine 10 with a joint flag 850 that serves as a reference for rotation of various instruments about the medial/lateral axis 20. The joint flag 850 has a shaft 852, an insertion plate 854, and a handle 856. The insertion plate 854 is generally flat and is coupled to the shaft 852 at a pre-established angle, which may be at or near a statistical average of the angle between the anterior surface of the facet joint 64 and the major axis of the associated pedicle 30. The handle 856 extends from the opposite end of the shaft 852 at a ninety degree angle, coplanar with the shaft 852 and the insertion plate 854.

After exposure of the facet joints 64, the insertion plate 854 is inserted into the "joint space," i.e., the space between the superior facet 38 of the left-hand side of the first vertebra 24 and the inferior facet 60 of the left-hand side of the second vertebra 26. The insertion plate 854 is inserted into the caudal edge of the joint space, and is then pressed generally along the cephalad direction 12 to provide thorough contact between the insertion plate 854 and the adjacent surfaces of the facets 38, 60. Since the handle 856 is coplanar with the shaft 852 and the insertion plate 854, the handle 856 provides visual confirmation that the insertion plate 854 is properly aligned.

Figure 21:
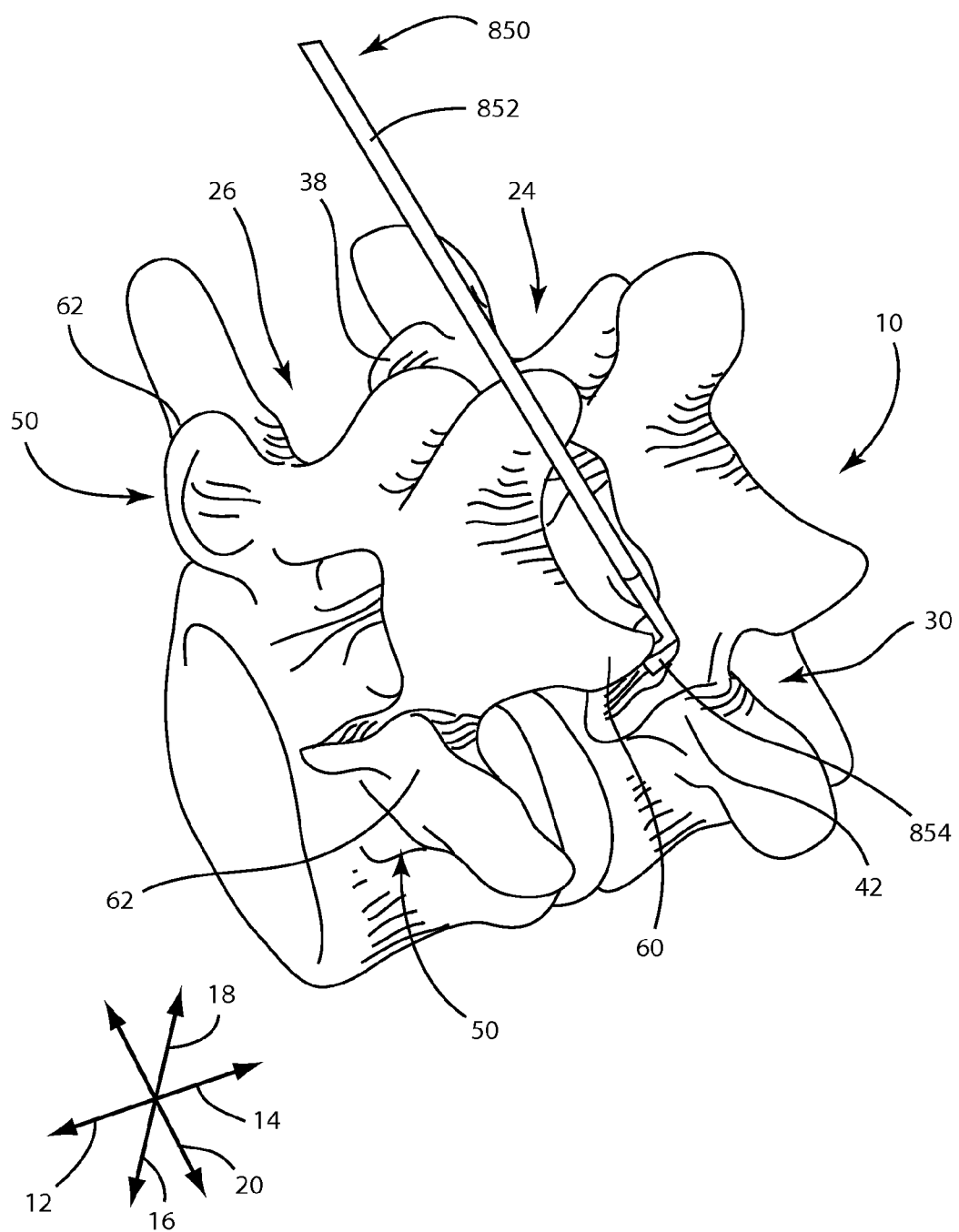
FIG. 21 is an enlarged, perspective view of the vertebrae of the spinal column of FIG. 1 with the joint flag in place.

Referring to FIG. 21, an enlarged, perspective view illustrates the first and second vertebrae 24, 26 with the joint flag 850 in place. After insertion of the insertion plate 854 into the joint space, the shaft 852 extends outward from the spine 10 at an angle that enables the shaft 852 to serve as a reference for other surgical instruments. Thus, surgical instruments may be coupled to the spine 10 based on the angle at which the facets 38, 60 contact each other.

When the joint flag 850 has been properly positioned, the saddle point 42 of the pedicle 30 of the left-hand side of the first vertebra 24 may be identified. A pin, chisel, or the like may be used to nick the saddle point 42 to indicate where the corresponding guide wire 668 should be implanted. The saddle point 42 is then prepared for implantation of the guide wire 668.

Figure 22:
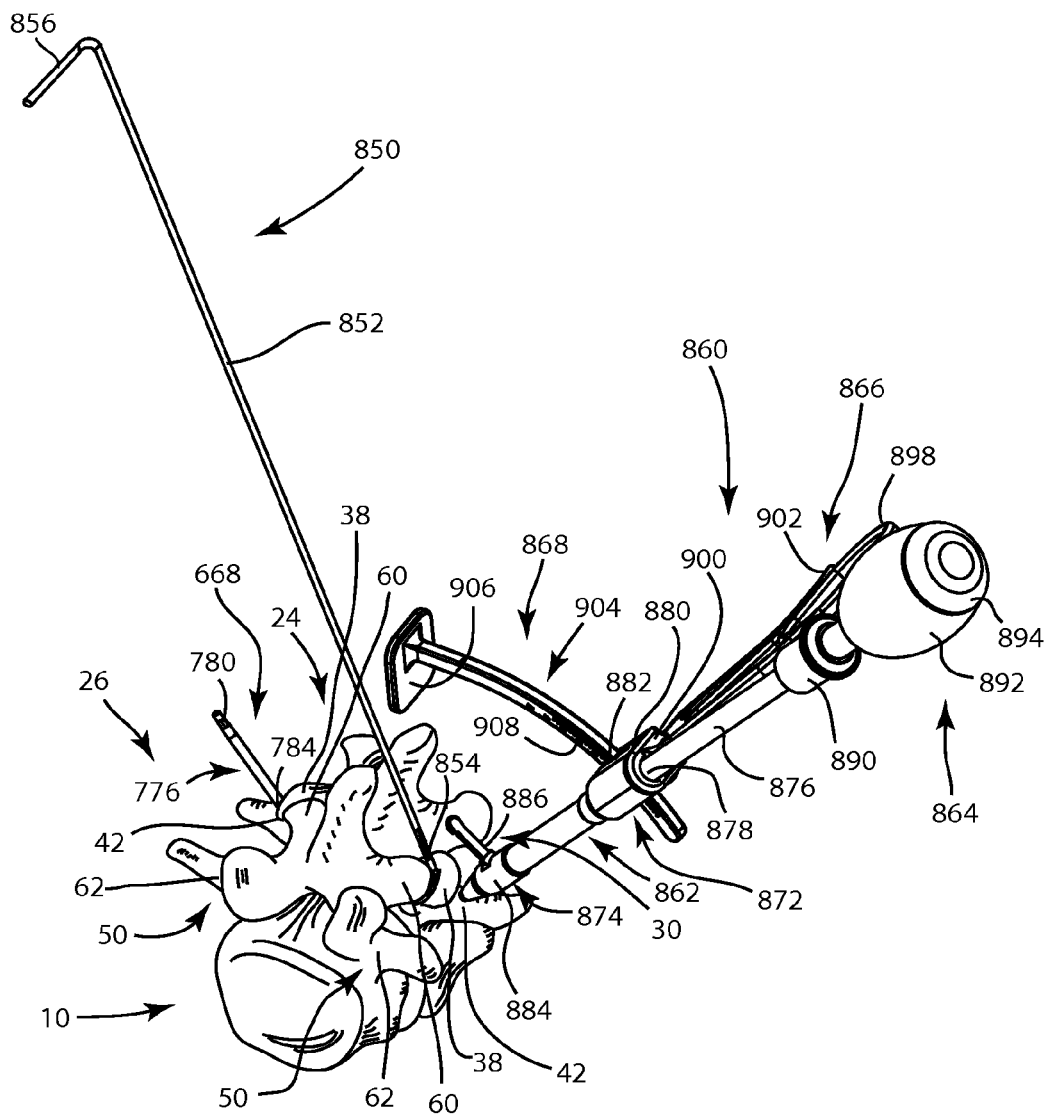
FIG. 22 is a perspective view of the L4 and L5 vertebrae with the joint flag in place, a guide wire inserted along the axis of one pedicle of the L5 vertebra, and a guide wire inserter aligned with the joint flag to facilitate insertion of a guide wire into the other pedicle of the L5 vertebra.
Figure 22:
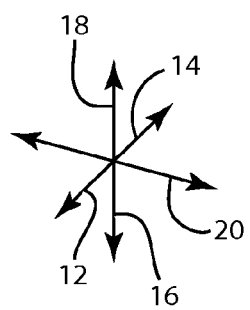

Referring to FIG. 22, a perspective view illustrates the first and second vertebrae 24, 26, with a guide wire inserter 860 positioned to implant the guide wire 668 into the saddle point 42 of the left-hand side of the first vertebra 24. As shown, the guide wire inserter 860 has a main body 862, a grip member 864, a handle member 866, and an angular reference member 868.

The main body 862 has a central portion 872 and an insertion portion 874. The central portion 872 has a generally cylindrical shape, and is coupled to the handle member 866 and the angular reference member 868. The central portion 872 receives a shaft 876 via a bore 878 passing through the central portion 872. The shaft 876 serves to couple the grip member 864 to the central portion 872. The central portion 872 also has a handle coupling 880 to which the handle member 866 is attached, and a slot 882 that receives the angular reference member 868.

The insertion portion 874 has a tapered end 884 that abuts the surface of the bone, i.e., the saddle point 42 of the pedicle 30 of the left-hand side of the first vertebra 24, to facilitate accurate implantation. The insertion portion 874 also has a guide extension 886 that protrudes from the tapered end 884. The guide extension 886 has two pairs of aligned notches that can be used to visually confirm that the saddle point 42 has been properly placed and that the anatomy of the spine 10 is within acceptable limits prior to implantation of the guide wire 668. The guide wire 668 may be positioned within the insertion portion 874 such that the leading end 778 of the guide wire 668 is able to exit the insertion portion 874 through the tapered end 884.

The grip member 864 has a coupling 890, a grip 892, and a strike plate 894. The grip member 864 may be a standardized, universal grip that is attachable to a wide variety of instruments to provide manual torque and/or linear force. Thus, the coupling 890 is removably attachable to the shaft 876, and to a variety of other surgical tools. The grip 892 is shaped to be comfortably grasped and rotated by hand. The strike plate 894 may be formed of a metal, and may be coupled to the coupling 890 via a metal support (not shown) extending through the interior of the grip 892 so that impact can be nondestructively transmitted from the strike plate 894 to the coupling 890.

The handle member 866 includes a handle 898, a body coupling 900, and a lever 902. The handle 898 is shaped to be easily grasped by a hand of a user. The body coupling 900 is shaped to facilitate attachment of the handle member 866 to the central portion 872 of the main body 862. The handle 898 and the body coupling 900 may be shaped similarly to the handle 358 and the attachment end 360 of the handle member 334 of the facet measurement tool 330 and the pedicle measurement tool 430. Accordingly, the body coupling 900 may be attached to the central portion 872 through the use of a screw (not shown) such as the screw 336 of the facet measurement tool 330 and the pedicle measurement tool 430.

The lever 902 of the handle member 866 may be pivotably coupled to the central portion 872. The lever 902 may be subject to resilient force provided by a spring (not shown) or the like such that, in the absence of actuation by a user, the lever 902 restricts motion of the angular reference member 868 through the slot 882 of the central portion 872. However, when the lever 902 is actuated toward the handle 898 by a user, the lever 902 permits motion of the angular reference member 868 through the slot 882. This permits rotational adjustment about the cephalad and caudal directions 12, 14 of the angle along which the guide wire 668 enters the saddle point 42.

As shown, the angular reference member 868 has an arcuate rod 904, a guide plate 906 attached to the arcuate rod 904, and a plurality of markings 908 arranged along the length of the arcuate rod 904. The guide plate 906 is generally square in shape, and is generally perpendicular to the end of the arcuate rod 904 to which it is attached. The markings 908 specify angles, and when the lever 902 is actuated to permit adjustment of the angular reference member 868, any of the markings 908 may be aligned with a marking (not shown) on the central portion 872 of the main body 862 to set the angle of rotation about the cephalad and caudal directions 12, 14 along which the guide wire 668 will be inserted.

The guide wire inserter 860 may be used in the following manner to implant the guide wire 668 into the saddle point 42 of the left-hand side of the first vertebra 24. A surgeon may first measure the angle at which the pedicle 30 of the left-hand side of the first vertebra 24 extends with respect to the sagittal plane 20. This may be accomplished by using the spinal morphology mapping from the CT scan performed previously. Then, the lever 902 may be actuated to release the angular reference member 868, and the arcuate rod 904 may be moved through the slot 862 until the markings 908 indicate that the angular reference member 868 is set at the proper angle. The lever 902 may then be released to keep the angular reference member 868 at the proper angle.

Then, the tapered end 884 of the insertion portion 874 of the main body 862 is placed on the saddle point 42. The guide wire inserter 860 is pivoted about the saddle point 42 until the guide plate 906 is parallel to the sagittal plane 22 and the shaft 876 is substantially coplanar with the shaft 852 of the joint flag 850. This form of alignment is more clearly illustrated in FIG. 23.

Figure 23:
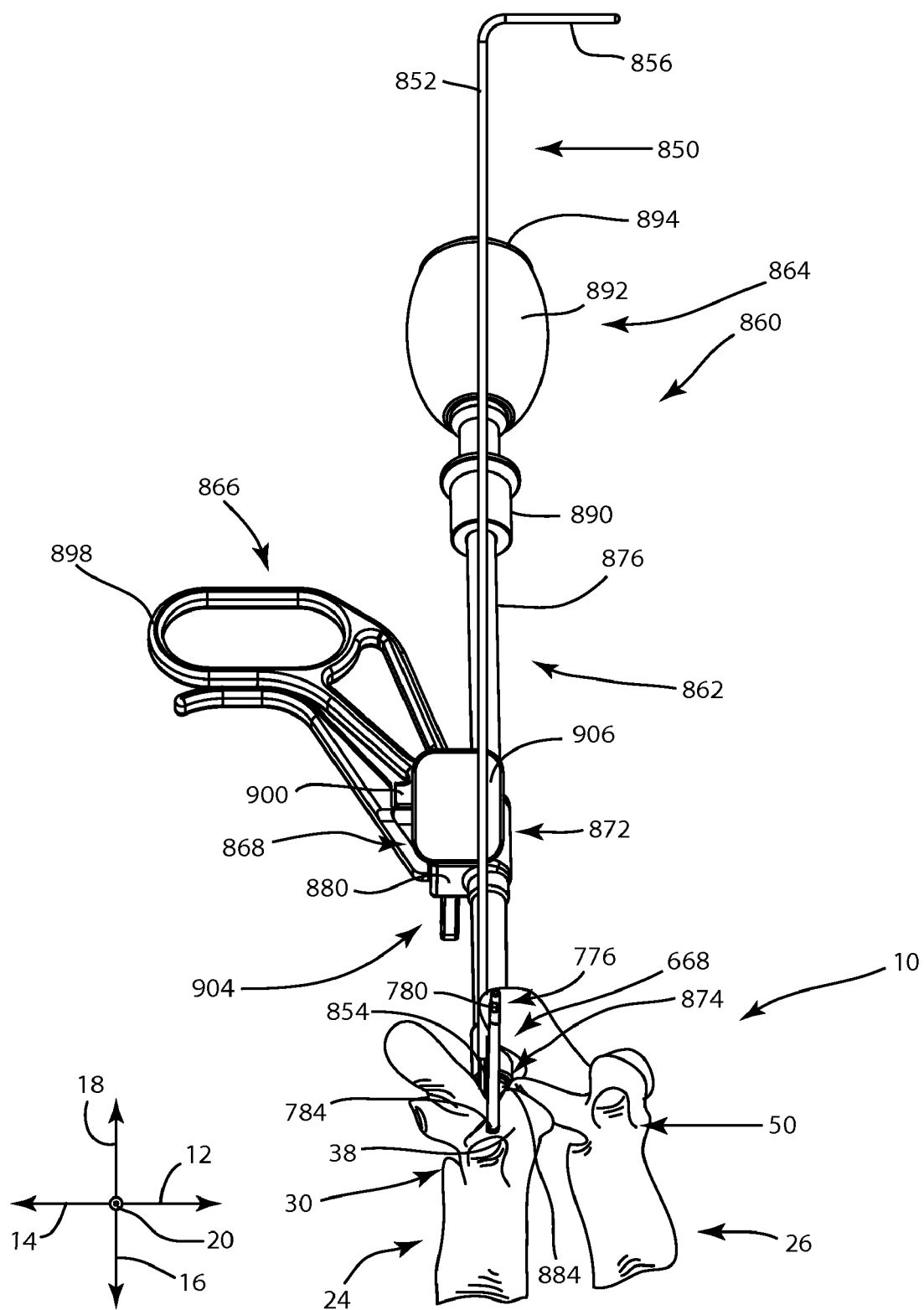
FIG. 23 is a lateral view of the L4 and L5 vertebrae with the joint flag and guide wire in place and the guide wire inserter aligned with the joint flag.

Referring to FIG. 23, a lateral view illustrates the first and second vertebrae 24, 26, with the joint flag 850 and the guide wire inserter 860 in position. As shown, the guide plate 906 of the angular reference member 868 is generally parallel to the sagittal plane 22 (shown in FIG. 1). Furthermore, the shaft 876 of the guide wire inserter 860 is oriented substantially coplanar with the shaft 852 of the joint flag 850. Thus, the guide wire inserter 860 has been rotated about the medial/lateral axis 20 to substantially the same angle as the joint flag 850.

As set forth above, alignment of the guide plate 906 with the sagittal plane 22 controls the medial/lateral angulation of the guide wire inserter 860, i.e., orientation via rotation about the cephalad and caudal directions 12, 14. Alignment of the shaft 876 with the shaft 852 of the joint flag 850 controls the cephalad/caudal angulation of the guide wire inserter 860, i.e., orientation via rotation about the medial/lateral axis 20. These two modes of alignment are used to ensure that the guide wire 668 permits the necessary range of multiaxial rotation of a semispherical bone apposition surface of a superior facet prosthesis (not shown in FIG. 23) against the saddle point 42 to permit proper alignment of the prosthesis. However, it has been found that a relatively wide range of implantation angles is acceptable for the guide wire 668. Accordingly, the above-described procedures for cephalad/caudal and medial/lateral alignment of the guide wire inserter 860 may be omitted in favor of expedited implantation of the guide wire 668.

After the guide wire inserter 860 has been oriented as desired, the surgeon may use the guide extension 866 to verify that the insertion portion 874 is properly positioned and that the anatomy of the spine 10 is within necessary boundaries. More precisely, when the surgeon looks down the length of the guide wire inserter 860, the joint space of the facet joint 64 should appear to cross the guide extension 866 between the pairs of notches. If this is not the case, the insertion portion 874 may be moved slightly to a location more suitable for implantation.

Then, a hammer or the like may be impacted against the strike plate 894 of the grip member 864. The impact is transferred through the coupling 890, through the shaft 876, and to the guide wire 668 within the insertion portion 874 of the guide wire inserter 860. The guide wire 668 is driven generally along the axis of the pedicle 30, or along the length of the pedicle 30. Once the guide wire 668 has been driven into the bone a sufficient distance, the guide wire inserter 860 may be removed. The guide wire inserter 860 may control the depth to which the guide wire 668 is implanted in the first vertebra 24. The guide wire 668 is driven into the bone until only one of the markings 784 of the central portion 776 of the guide wire 668 is showing above the surface of the bone.

After the guide wires 668 have been implanted in both pedicles 42 of the first vertebra 24, the superior facets 38 of the first vertebra 24 may be preliminarily resected. The preliminary resection may not need to be accurately guided or measured. Rather, a minimal amount of bone tissue, i.e., only the superior articular process, is removed from the superior facets 38 to enhance access to the joint space of the facet joints 64 and to further expose the inferior facets 60 of the second vertebra 26 for resection. Further, more precise resection of the superior facets 38 of the first vertebra 24 will be performed subsequently to prepare the first vertebra 24 to receive superior facet prostheses.

Figure 24:
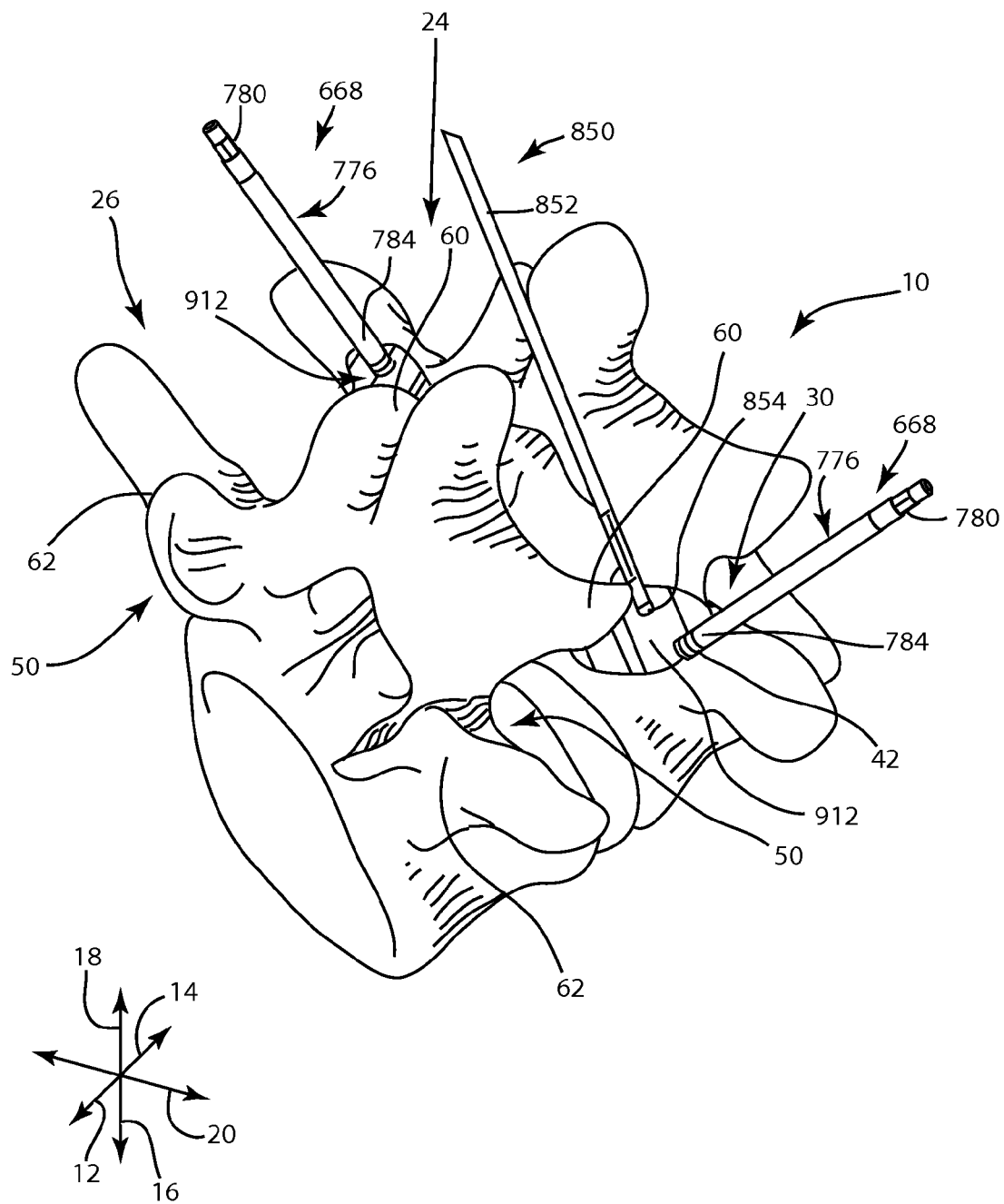
FIG. 24 is a perspective view of the L4 and L5 vertebrae with the joint flag in place, guide wires inserted along the axis of each pedicle of the L5 vertebra, and the superior facets of the L5 vertebrae preliminarily resected.

Referring to FIG. 24, a perspective view illustrates the first and second vertebrae 24, 26, with the joint flag 850 and the guide wires 668 in place. The superior facets 38 of the first vertebra 24 have been preliminarily resected to form preliminary resection surfaces 912 on the first vertebra 24. Such preliminary resection may be carried out with a reciprocating bone saw or the like. As mentioned previously, further resection of the superior facets 38 of the first vertebra 24 will be carried out subsequently. After preliminary resection has been carried out, the saddle points 42 of the first vertebra 24 may be reamed to enable attachment of the frame 110.

Figure 25:
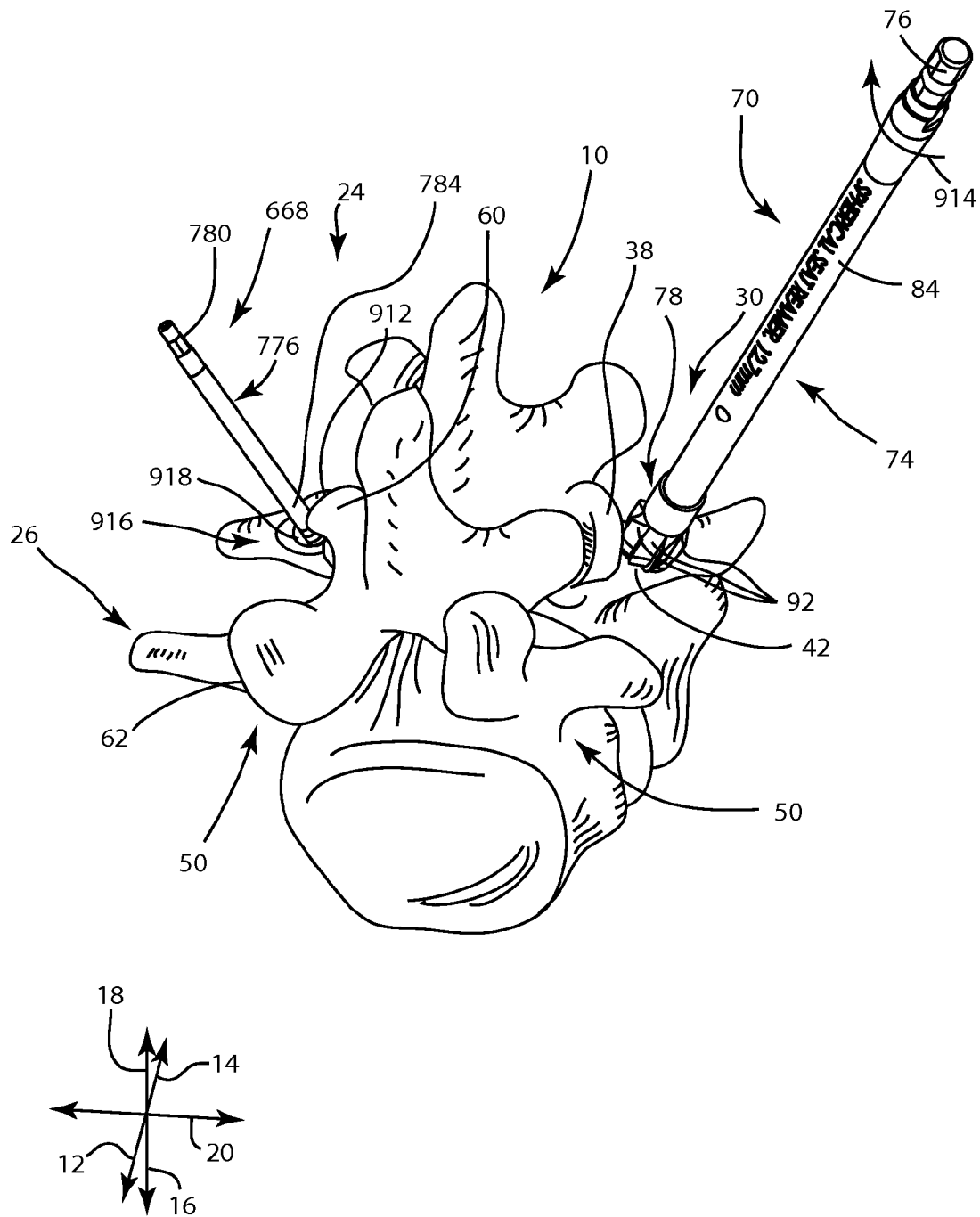
FIG. 25 is a perspective view of the L4 and L5 vertebrae with the guide wires in place, with one pedicle of the L5 vertebra partially reamed to provide a roughened semispherical surface, and the primary reamer positioned to ream the other pedicle of the L5 vertebra.

Referring to FIG. 25, a perspective view illustrates the first and second vertebrae 24, 26 with the right-hand saddle point 42 of the first vertebra 24 partially reamed, and with the primary reamer 70 positioned to ream the left-hand saddle point 42. As shown, the primary reamer 70 has been registered on the guide wire 668 of the left-hand saddle point 42. More precisely, the portion of the guide wire 668 exposed outside the bone of the first vertebra 24 is inserted into the bore 88 of the primary reamer 70 to register the primary reamer 70 with respect to the saddle point 42. Thus, motion of the primary reamer 70 is constrained to rotation about the axis of the guide wire 668 and motion along the guide wire 668.

The primary reamer 70 is coupled at the torque interface 76 to a handle, motor, or the like (not shown). The primary reamer 70 may operate most effectively when driven by a motor. The primary reamer 70 rotates along a direction 914 such that the cutting flanges 92 scrape away bone tissue from around the saddle point 42. The primary reamer 70 is advanced into the pedicle 30 until the flat surface 90 abuts the bone immediately surrounding the guide wire 668. The primary reamer 70 is then unable to advance further into the bone, and is withdrawn to leave a roughened semispherical surface 916, as shown on the right-hand side of the first vertebra 24. The roughened semispherical surface 916 has a plateau 918 immediately surrounding the guide wire 688, where the primary reamer 70 was unable to remove the bone tissue.

Figure 26:
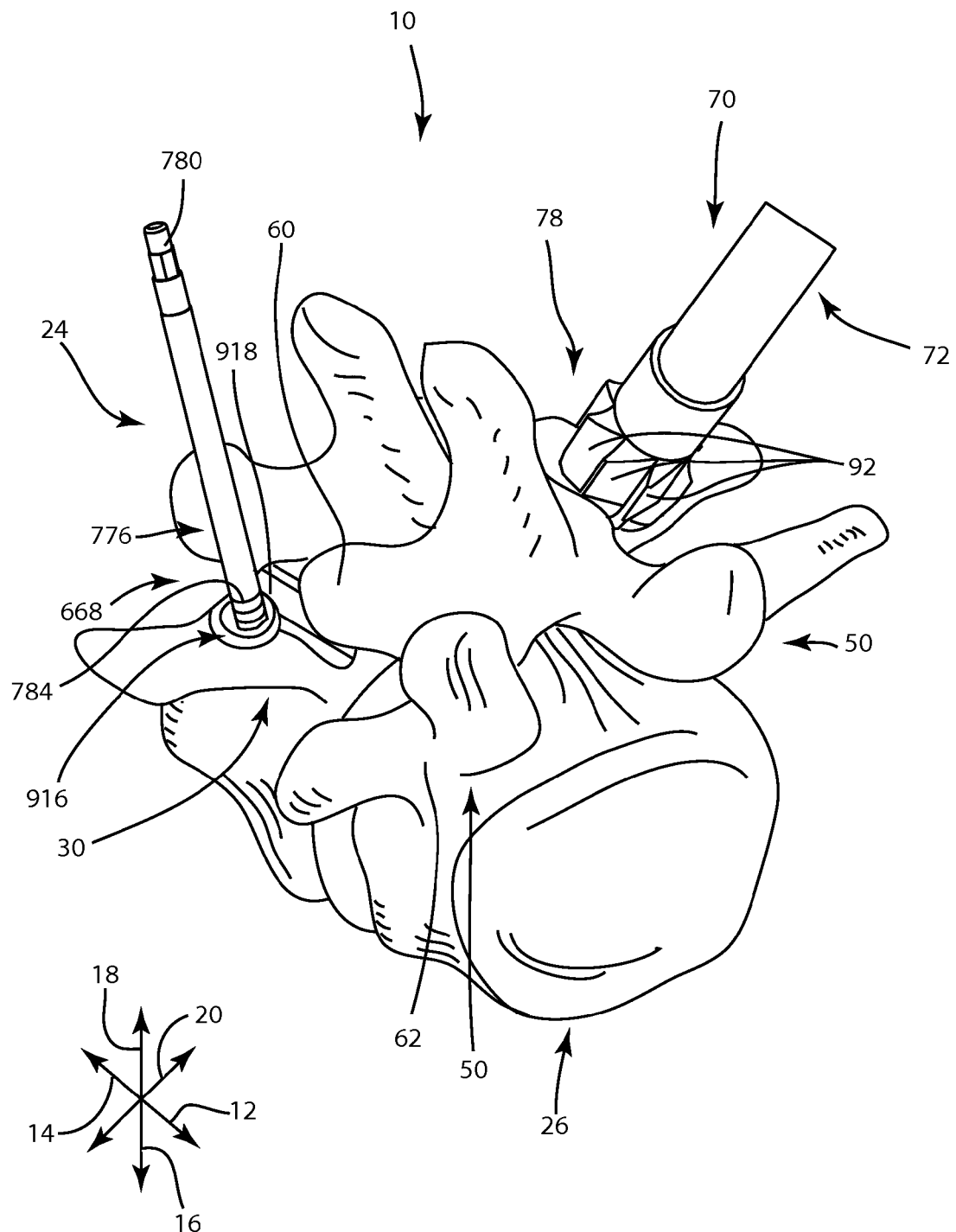
FIG. 26 is an enlarged, perspective view of the L4 and L5 vertebrae with the guide wires and the primary reamer in place.

Referring to FIG. 26, a perspective view illustrates the first and second vertebrae 24, 26 with the right-hand saddle point 42 of the first vertebra 24 partially reamed, and with the primary reamer 70 positioned to ream the left-hand saddle point 42, as in FIG. 25. The plateau 918 of the roughened semispherical surface 916 is more clearly shown. The plateau 918 will be removed via the secondary reamer 72.

Figure 27:
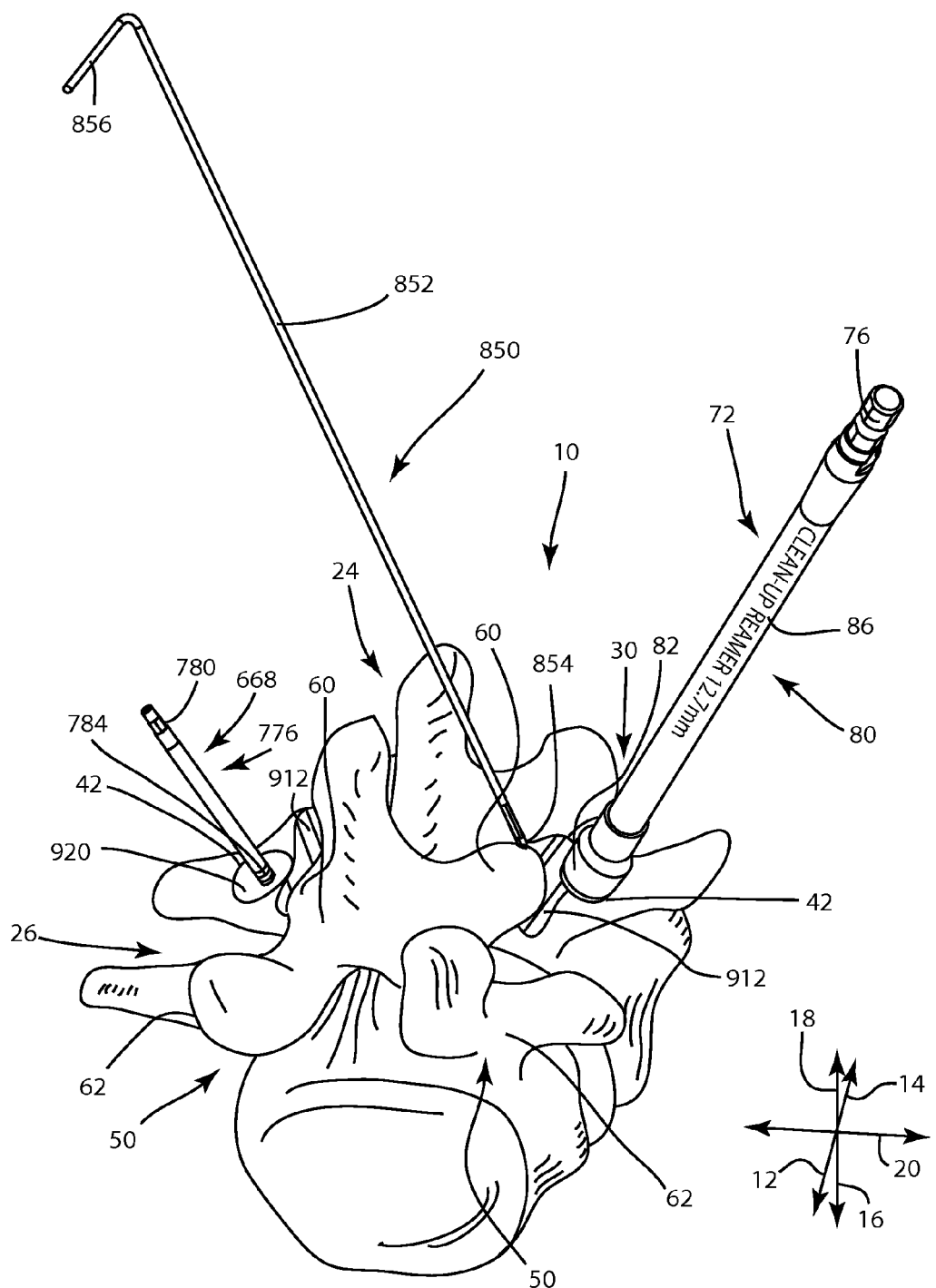
FIG. 27 is a perspective view of the L4 and L5 vertebrae with the guide wires and the joint flag in place, with one pedicle of the L5 vertebra fully reamed to provide a semispherical surface, and with the secondary reamer positioned to ream the other pedicle of the L5 vertebra in alignment with the joint flag.

Referring to FIG. 27, a perspective view illustrates the first and second vertebrae 24, 26 with the right-hand saddle point 42 of the first vertebra 24 fully reamed, and with the secondary reamer 72 positioned to complete reaming of the left-hand saddle point 42. As described previously, the dome 102 of the secondary reamer 72 is advanced into the roughened semispherical surface 916. However, the dome 102 does not remove bone tissue, and thus, the roughened semispherical surface 916 remains at its proper depth. The central teeth 100 remove the plateau 918 to leave a semispherical interface 920 at the saddle point 42.

Figure 28:
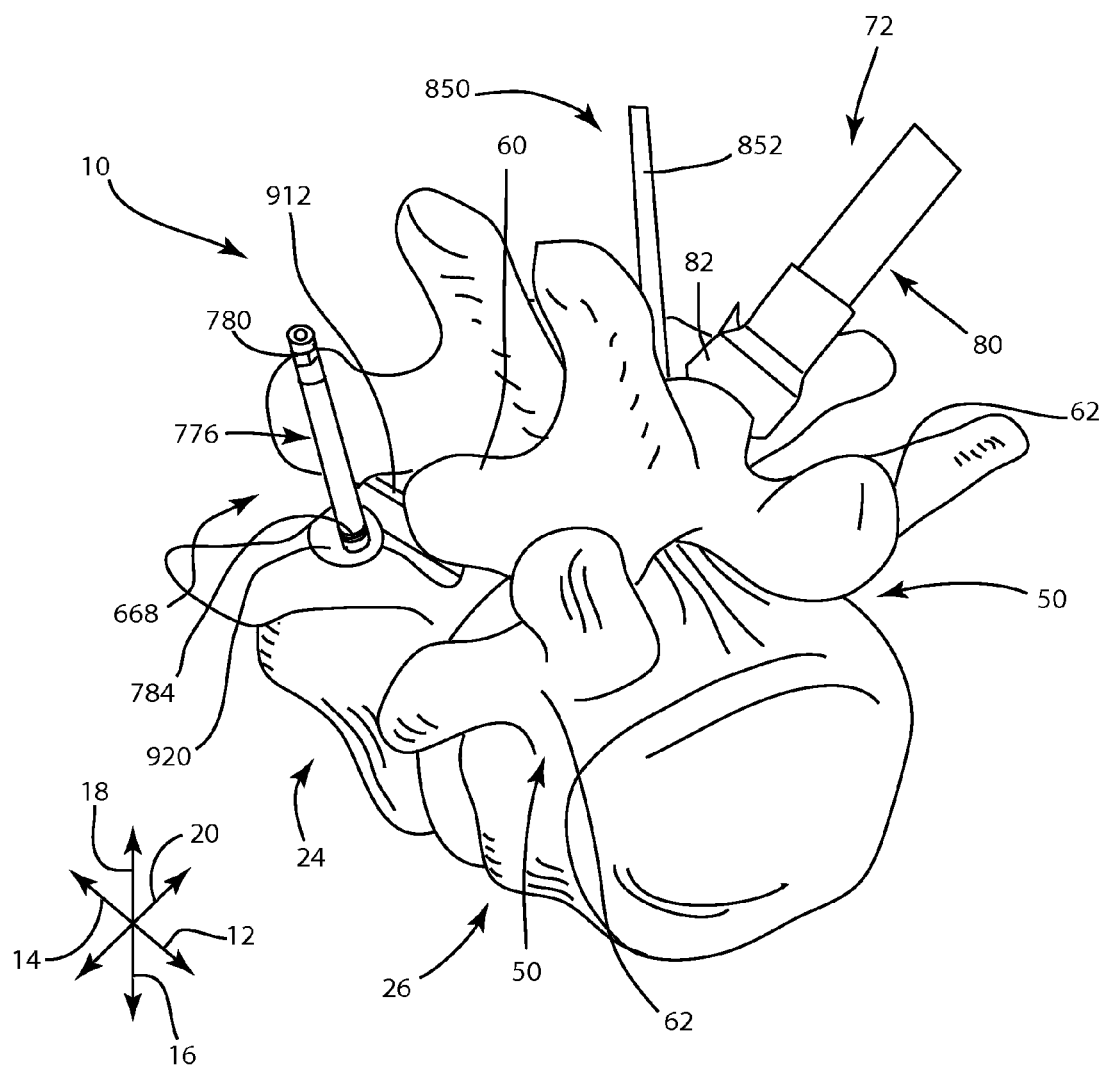
FIG. 28 is an enlarged, perspective view of the L4 and L5 vertebrae with the guide wires, joint flag, and secondary reamer in place.

Referring to FIG. 28, a perspective view illustrates the first and second vertebrae 24, 26 with the right-hand saddle point 42 of the first vertebra 24 fully reamed, and with the secondary reamer 72 positioned to complete reaming of the left-hand saddle point 42, as in FIG. 27. The semispherical interface 920 on the right-hand side of the first vertebra 24 is more clearly visible. The effect of the progressive use of the primary and secondary reamers 70, 72 is to accurately control the depth of the semispherical interface 920 so that, at its deepest, the semispherical interface 920 is, for example, two millimeters below the former bone surface of the saddle point 42.

If a deeper ream is desired, the procedure illustrated in FIGS. 25, 26, 27, and 28 may be repeated by using the primary reamer 70 to add limited depth to the ream, and then using the secondary reamer 72 to complete reaming to the additional depth. Thus, the depth of a reamed indentation may be increased by discrete quantities, such as two millimeters.

After the saddle points 42 of the first vertebra 24 have been reamed to provide the semispherical interfaces 920, the frame 11 may be anchored to the spine 10. In this application, "anchoring" refers to contacting one part with another to limit relative motion between the two parts. "Coupling" refers to contacting one part with another, either directly or through a third part, to limit relative motion between the first two parts.

The frame 110 may easily be anchored on the first vertebra 24. The locking mechanism 144 may first be moved to the unlocked configuration by rotating the handle 202 counterclockwise, as viewed from above, to permit the first, second, and third rods 164, 184, 210 to slide relatively freely within the first, second, and third sliders 212, 220, 222. The first and second anchors 112, 114 may thus be repositioned along three orthogonal axes to slide the bore 130 of the anchoring feature 122 of the first anchor 112 over the guide wire 668 of the left-hand side of the first vertebra 24, and to slide the bore 130 of the anchoring feature 122 of the second anchor 114 over the guide wire 668 of the right-hand side of the first vertebra 24.

Each of the semispherical surfaces 128 of the anchoring features 122 is then seated in the corresponding semispherical interface 920 of the first vertebra 24. With the semispherical surfaces 128 seated against the semispherical interfaces 920, the frame 110 is pivotable only about the medial/lateral axis 20, or about an axis angularly displaced slightly therefrom. Since the semispherical surfaces 128 permit pivotal motion with respect to the first vertebra 24, they are "pivot features" within the meaning of this application. The frame 110 is pivoted about the medial/lateral axis 20 until the frame 110 is oriented generally parallel to the shaft 852 of the joint flag 850.

The stationary external support 260 is then attached to the frame 110. More precisely, the fixed end 262 of the stationary external support 260 is attached to a stationary object such as an operating table, wall, or the like. The first, second, and third joints 276, 278, 280 of the stationary external support 260 are all unlocked by rotating the corresponding handles 286, 296 counterclockwise, thereby permitting relative rotation and/or translation of the first, second, and third rods 270, 272, 274. The handle 296 of the grip 264 is also actuated to permit the first and second gripping members 312, 314 to move apart from each other.

The first, second, and third joints 276, 278, 280 are moved to position the grip 264 proximate the external anchor 116 of the frame 110, and the generally spherical surface 136 of the external anchor 116 is then inserted into the space between the gripping members 312, 314. Then, the handles 286, 296 of the joints 276, 278, 280 are moved clockwise to lock the joints 276, 278, 280. The handle 296 of the grip 264 is also moved clockwise to draw the first and second gripping members 312, 314 closer together to grip the generally spherical surface 136 of the external anchor 116.

Attachment of the stationary external support 260 to the frame 110, in combination with coupling of the frame 110 to the first vertebra 24, makes the frame 110 a stable platform for surgical instrument registration. However, external attachment is optional, and in alternative embodiments, the stationary external support 260 need not be used. Furthermore, attachment to the first vertebra 24 is optional, as a frame (not shown) coupled only to the stationary external support 260 may still be stable enough to guide spinal measurement and resection operations. Indeed, if desired, surgical instruments could be made to register directly on the grip 264 of the stationary external support 260. The remainder of this disclosure assumes that both anchoring to the vertebra 24 and attachment to the stationary external support 260 are used.

Figure 29:
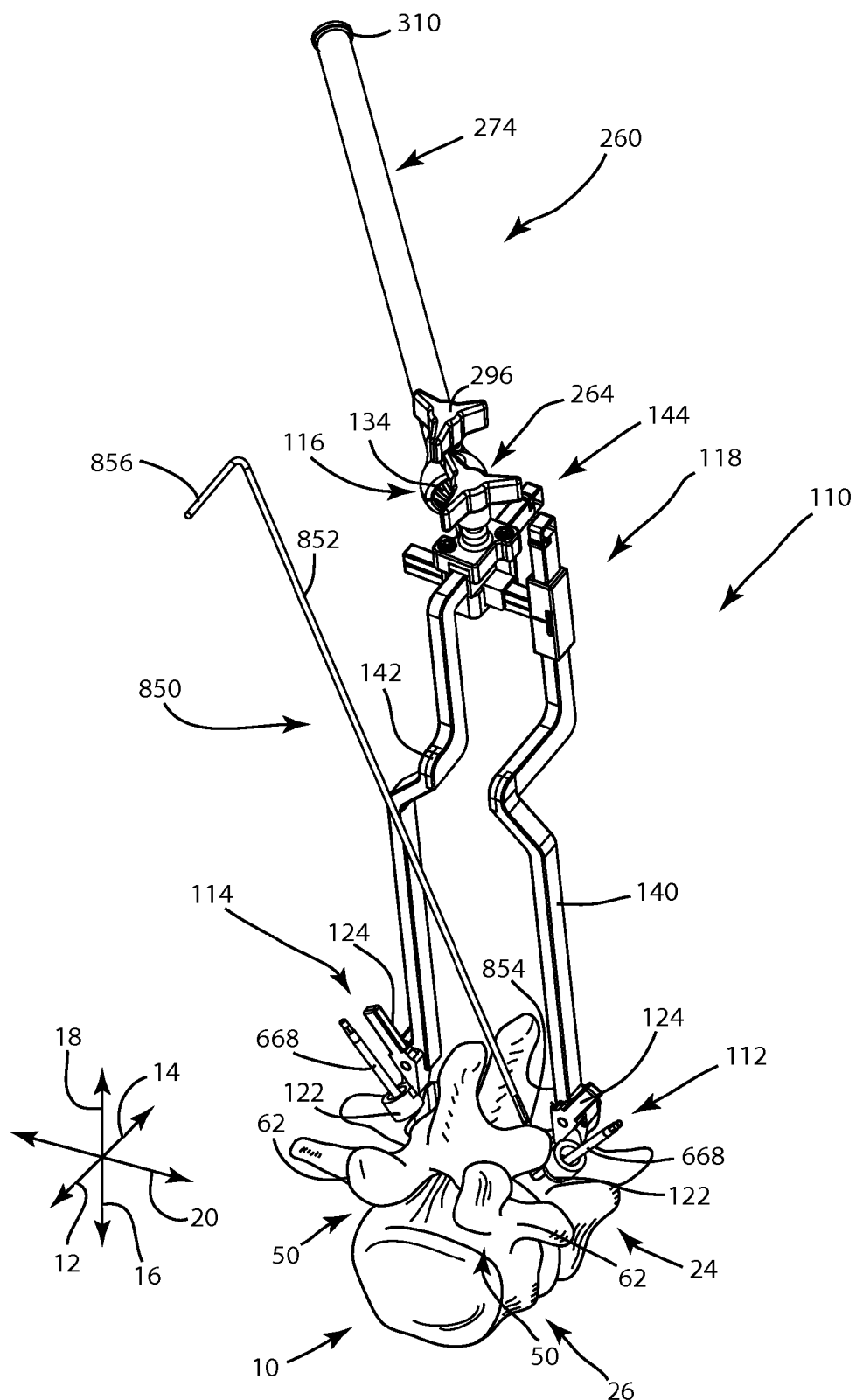
FIG. 29 is a perspective view of the L4 and L5 vertebrae with the guide wires and the joint flag in place and the frame attached to the stationary external support and to the reamed surfaces of the pedicles of the L5 vertebra, in alignment with the joint flag.

Referring to FIG. 29, a perspective view illustrates the first and second vertebrae 24, 26 with the guide wires 668 and joint flag 850 in place, and with the frame 110 anchored to the first vertebra 24 and coupled to the stationary external support 260. The stationary external support 260 is substantially rigid and securely grips the external anchor 116 to stabilize the frame 110, and especially, fix the orientation of the frame 110 about the medial/lateral axis 20 to be substantially parallel to the shaft 852 of the joint flag 850.

Figure 30:
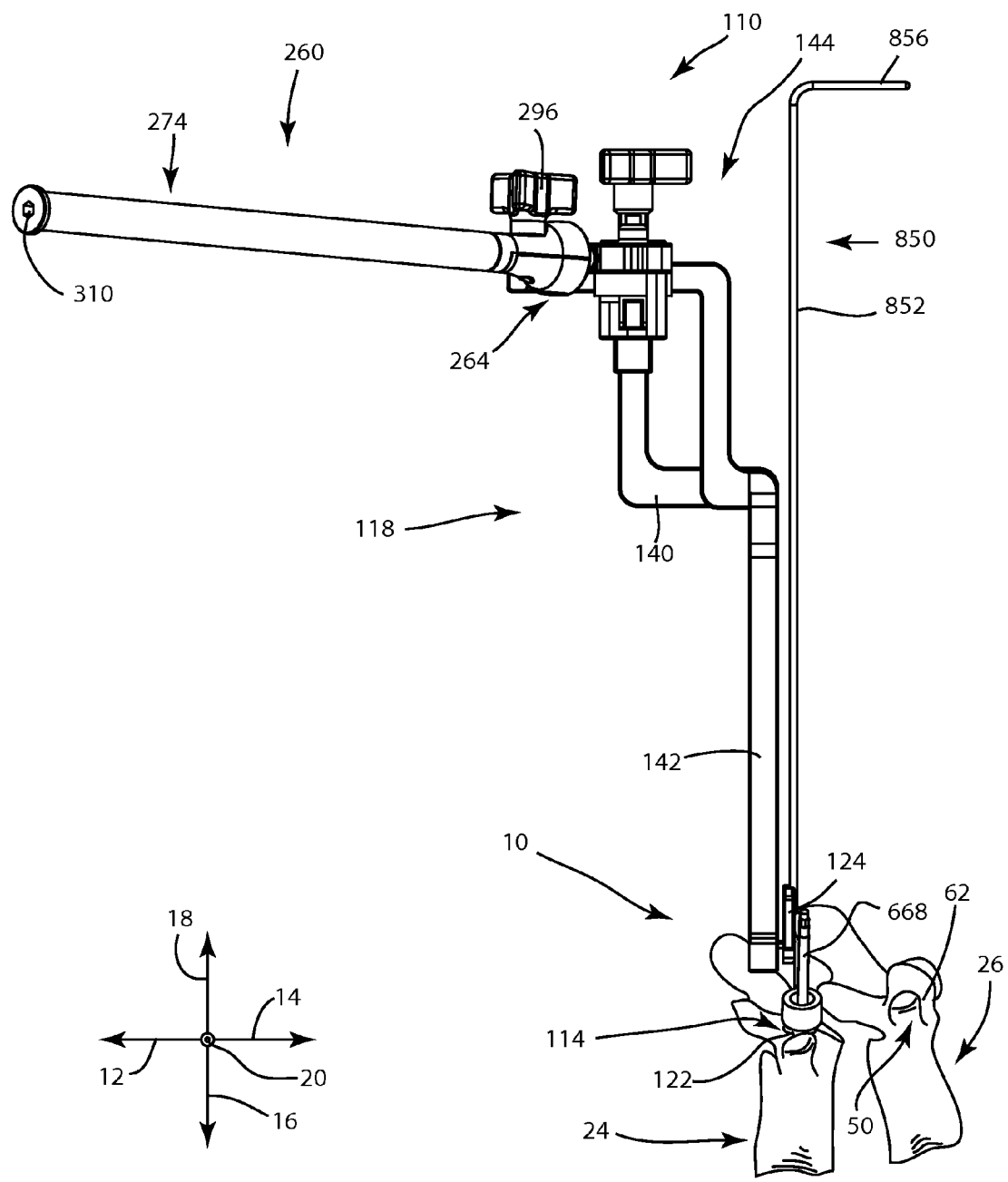
FIG. 30 is a lateral view of the L4 and L5 vertebrae with the guide wires, joint flag, frame, and stationary external support in place.

Referring to FIG. 30, a lateral view illustrates the first and second vertebrae 24, 26 with the guide wires 668 and joint flag 850 in place, and with the frame 110 anchored to the first vertebra 24 and coupled to the stationary external support 260. As shown, the frame 110 is oriented substantially parallel to the shaft 852 of the joint flag 850. The frame 110 is then ready to receive registration of surgical instruments to facilitate additional measurement and resection operations. The joint flag 850 may be removed and set aside. Holes (not shown in FIG. 30) may then be drilled or burred through the inferior facets 60 of the second vertebra 26 to expose P1, or the most medial and anterior surface, of each of the superior facets 38 of the first vertebra 24 in preparation for measurement of the location of P1.

The facet measurement tool 330 may then be used to measure the location of P1. More precisely, the registration interface 342 of the facet measurement tool 330 may be registered on the first anchor 112 by sliding the bore 348 of the registration interface 342 over the guide post 124 of the first anchor 112. The user then grasps the grip 378 of the contact member 340 and moves it to slide the first and second rods 364, 374 within the first and second sliders 344, 366 until the contact feature 382 is positioned to contact P1.

Figure 31:
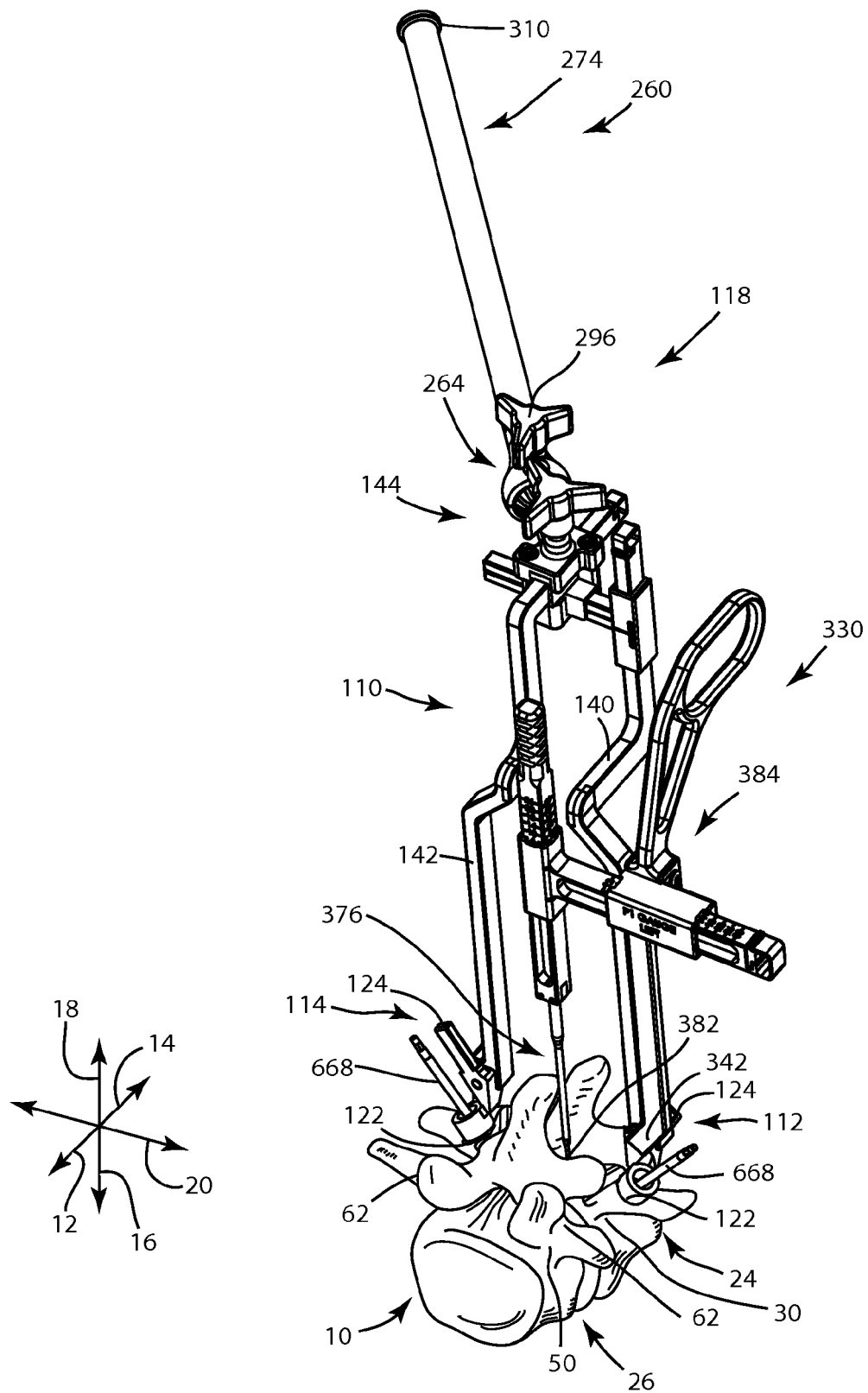
FIG. 31 is a perspective view of the L4 and L5 vertebrae with the guide wires, frame, and stationary external support in place, with the facet measurement tool registered to the frame to measure the position of the most medial and anterior surface of a superior facet of the L5 vertebra.

Referring to FIG. 31, a perspective view illustrates the first and second vertebrae 24, 26 with the guide wires 668, frame 110, and stationary external support 260 in place, and with the facet measurement tool 330 registered to the frame 110 to measure P1. Once the contact feature 382 is in contact with P1, measurements corresponding to the location of P1 may be acquired from the first and second rods 364, 374, with respect to the saddle point 38 of the left-hand side of the first vertebra 24. The measurements may be read as indicated previously, in connection with the description of FIG. 9.

Figure 32:
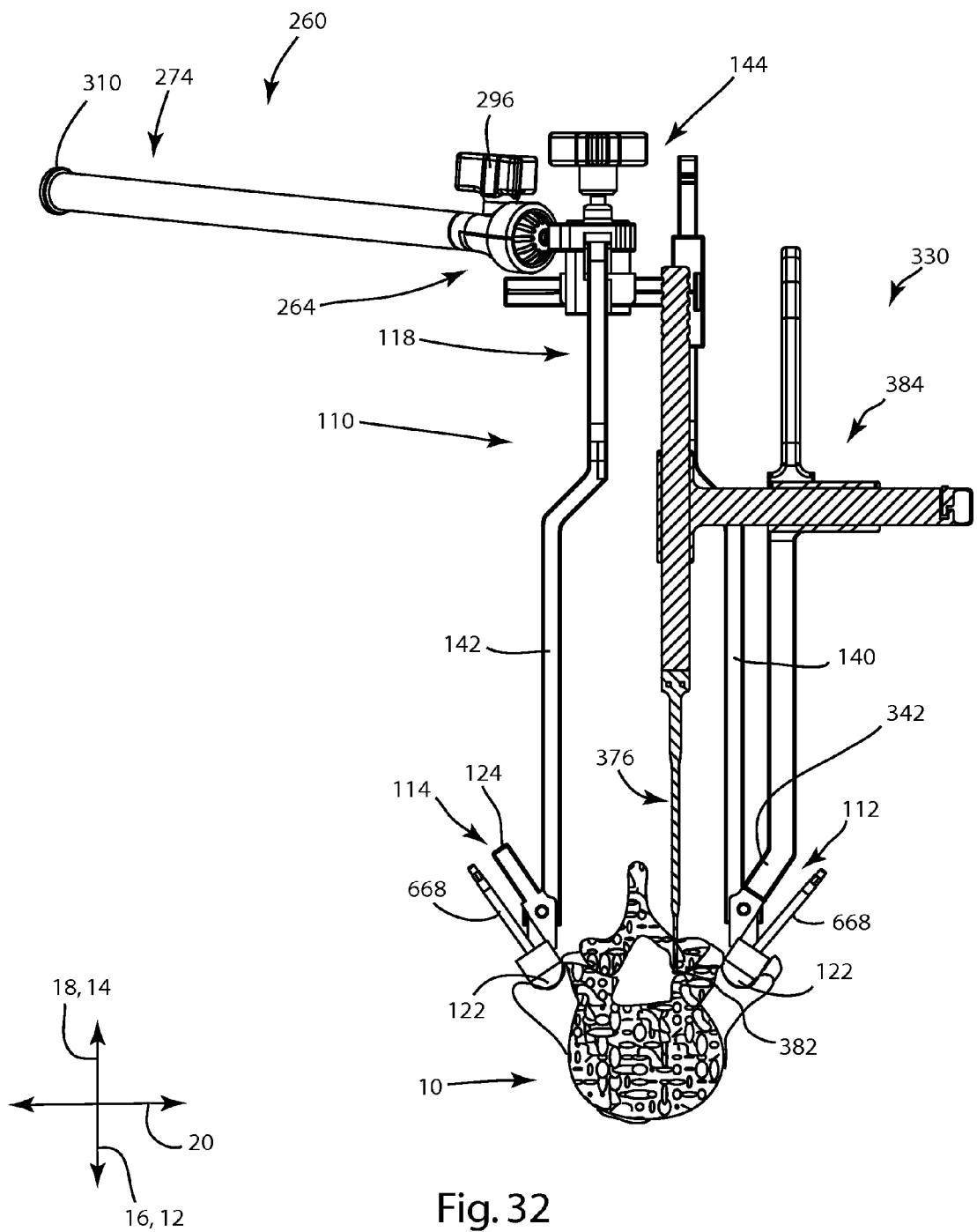
FIG. 32 is a cephalad section view of the L4 and L5 vertebrae with the guide wires, frame, stationary external support, and facet measurement tool in place.

Referring to FIG. 32, a cephalad section view illustrates the first and second vertebrae 24, 26 with the guide wires 668, frame 110, and stationary external support 260 in place, and with the facet measurement tool 330 registered to the frame 110 to measure P1. The section view more clearly illustrates the position of the contact feature 382 when measurement is conducted, and the manner in which the inferior facets 60 of the second vertebra 26 have been drilled or burred through to expose P1 for each of the superior facets 38 of the first vertebra 24. The contact extension 376 of the contact member 340 extends through the opening formed by drilling or burring to enable the contact the feature 38 to contact P1.

When the position of P1 has been measured, the facet measurement tool 330 may be removed. The pedicle measurement tool 430 may then be used to measure the position of the saddle point 62 of the left-hand side of the second vertebra 26, with respect to the saddle point 42 of the left-hand side of the first vertebra 24. More precisely, the registration interface 342 of the pedicle measurement tool 430 may be registered on the first anchor 112 by sliding the bore 348 of the registration interface 342 over the guide post 124 of the first anchor 112. The user then grasps the grip 378 of the contact member 440 and moves it to slide the first, second, and third rods 464, 466, 494 within the first, second, and third sliders 444, 476, 478 until the contact feature 502 is positioned to contact the saddle point 62 of the left-hand side of the second vertebra 26.

Figure 33:
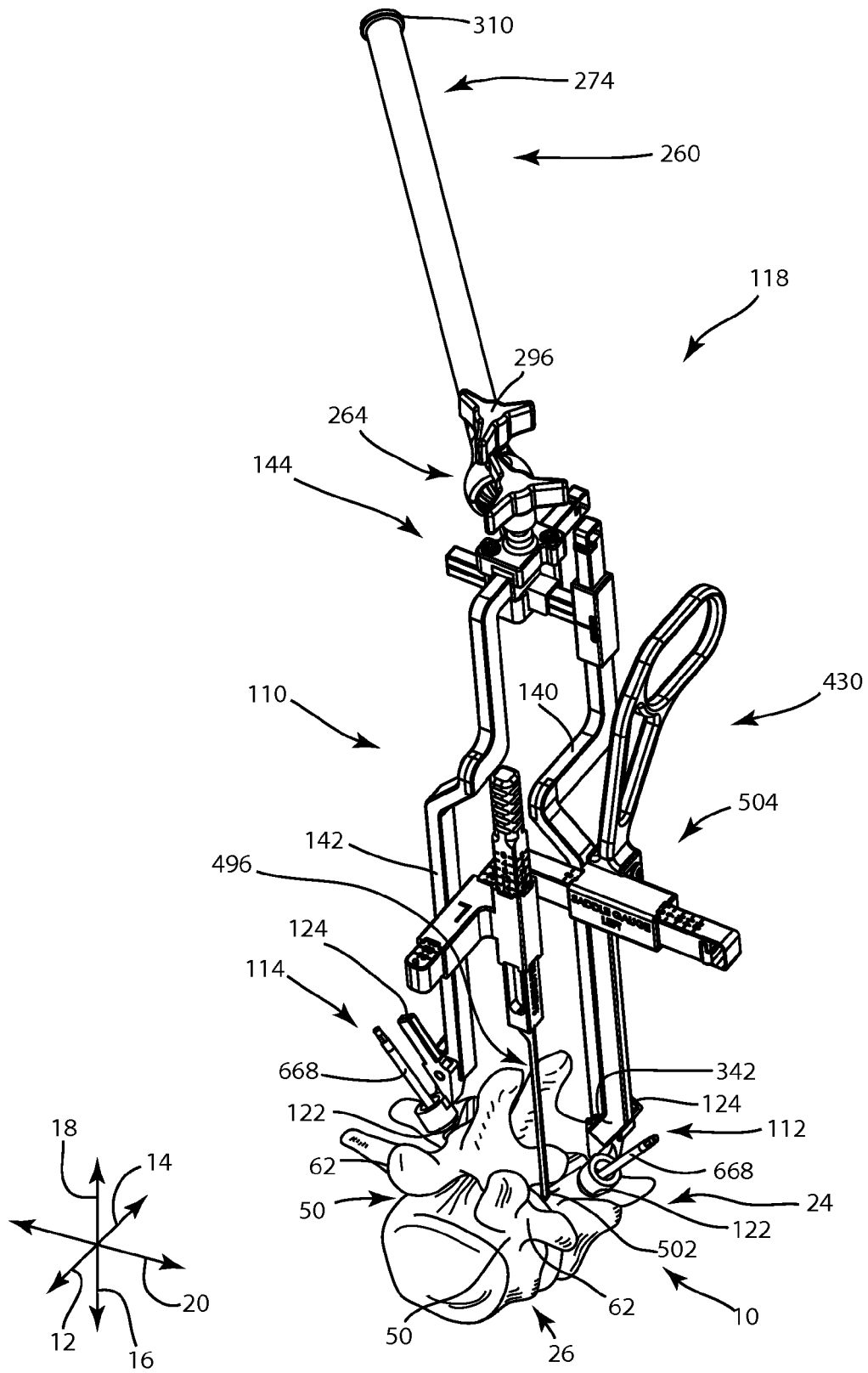
FIG. 33 is a perspective view of the L4 and L5 vertebrae with the guide wires, frame, and stationary external support in place, with the pedicle measurement tool registered to the frame to measure the position of the pedicle of the L4 vertebra.

Referring to FIG. 33, a perspective view illustrates the first and second vertebrae 24, 26 with the guide wires 668, frame 110, and stationary external support 260 in place, and with the pedicle measurement tool 430 registered to the frame 110 to measure the saddle point 62. Once the contact feature 502 is in contact with the saddle point 62, measurements corresponding to the location of the saddle point 62 may be acquired from the first, second, and third rods 464, 466, 494, with respect to the saddle point 38 of the left-hand side of the first vertebra 24. The measurements may be read as indicated previously, in connection with the description of FIG. 12.

Figure 34:
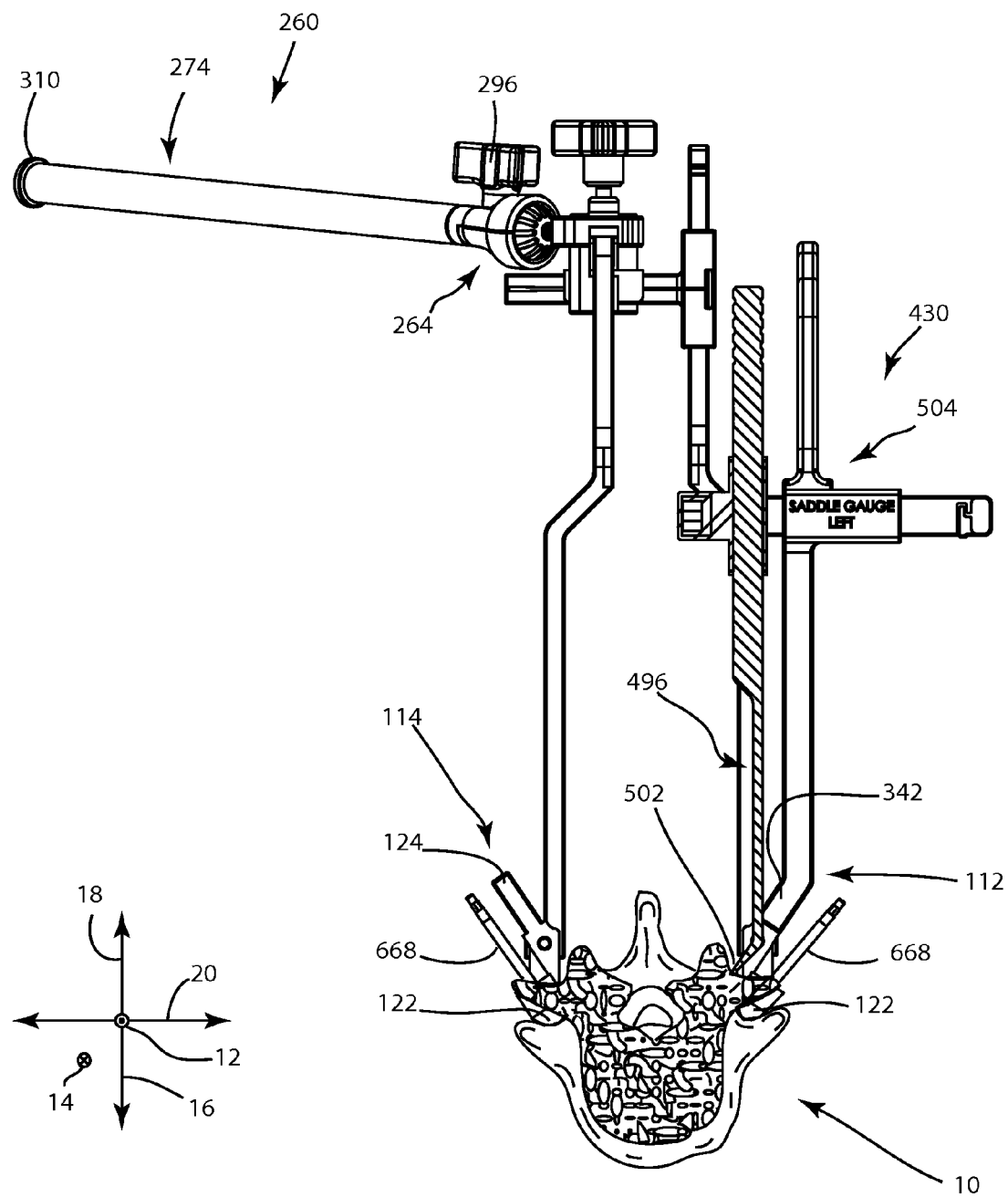
FIG. 34 is a cephalad section view of the L4 and L5 vertebrae with the guide wires, frame, stationary external support, and pedicle measurement tool in place.

Referring to FIG. 34, a cephalad section view illustrates the first and second vertebrae 24, 26 with the guide wires 668, frame 110, and stationary external support 260 in place, and with the pedicle measurement tool 430 registered to the frame 110 to measure the saddle point 62. The section view more clearly illustrates the position of the contact feature 502 when measurement is conducted. When the position of the saddle point 62 has been measured, the pedicle measurement tool 430 may be removed. The measurements obtained from the facet measurement tool 330 and the pedicle measurement tool 430 may be used to verify or change the selection of inferior and superior prostheses made previously to ensure that the selected prostheses match the shapes of the superior and inferior facets 38, 60 as closely as possible.

After measurement has been carried out with the measurement tools 330, 430, guide wires 668 may then be inserted into the saddle points 62 of the second vertebra 26. Guide wire implantation into the saddle points 62 of the second vertebra 26 may be carried out in a manner very similar to that of implantation into the saddle points 42 of the first vertebra 24.

Figure 35:
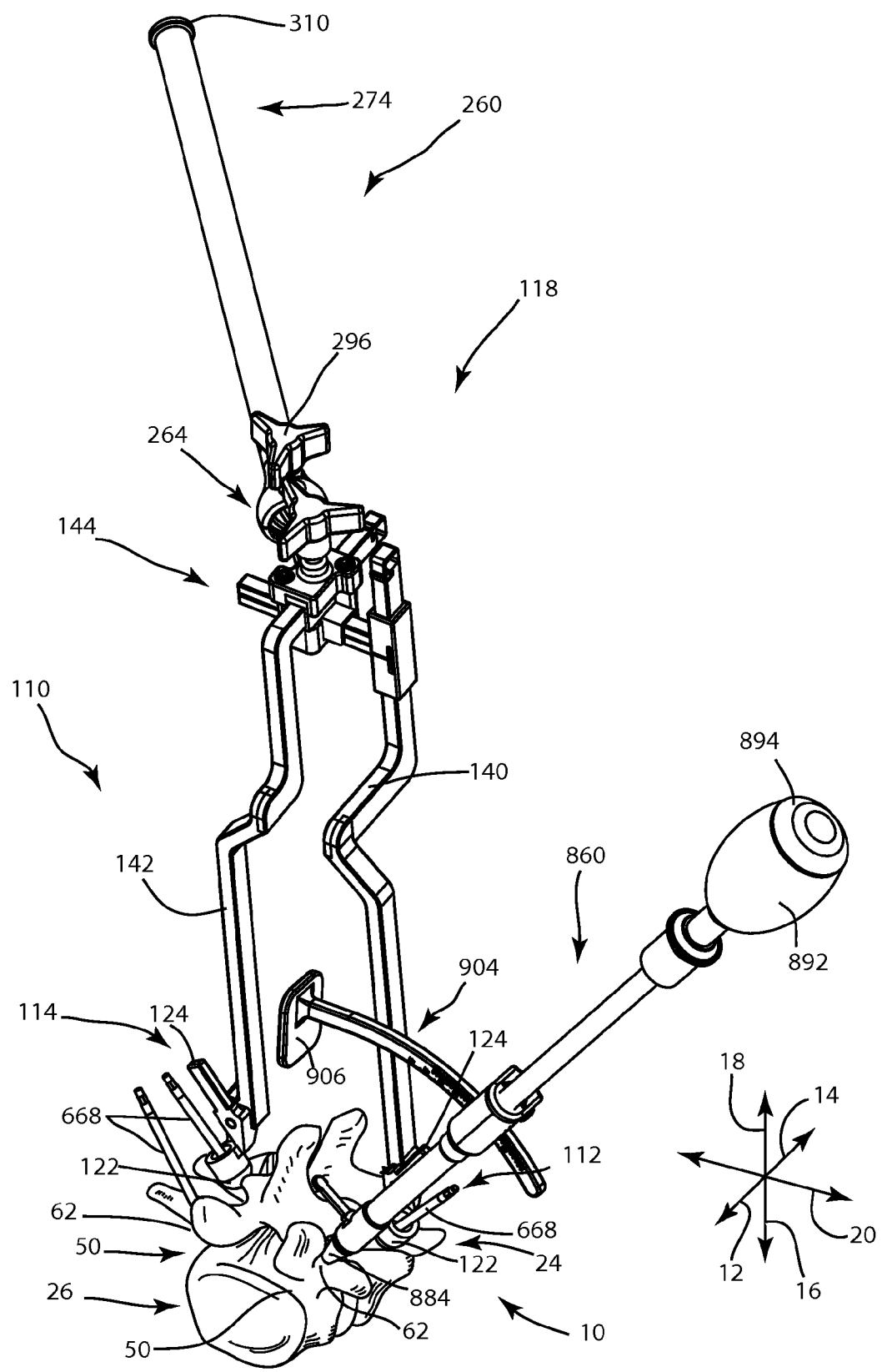
FIG. 35 is a perspective view of the L4 and L5 vertebrae with the L5 guide wires, frame, and stationary external support in place, with an additional guide wire inserted along the axis of one pedicle of the L4 vertebra, and the guide wire inserter positioned to facilitate insertion of another guide wire into the other pedicle of the L4 vertebra.

Referring to FIG. 35, a perspective view illustrates the first and second vertebrae 24, 26 with the guide wires 668, frame 110, and stationary external support 260 in place, and with the guide wire inserter 860 positioned to insert a guide wire (not visible in FIG. 35) into the saddle point 62 of the left-hand side of the second vertebra 26. The lever 902 may be actuated to enable the arcuate rod 904 of the angular reference member 868 to slide through the slot 882 of the central portion 872 of the main body 862. The arcuate rod 904 may then be moved to indicate the proper angle, and the lever 902 may be released to keep the angular reference member 868 at the angle.

The guide plate 906 is then aligned with the sagittal plane 22 (shown in FIG. 1), and the guide wire inserter 860 is rotated into alignment with the major axis of the corresponding pedicle 50 of the second vertebra 26, as viewed from a lateral viewpoint. The strike plate 894 may then be tapped to insert the guide wire 668 into the saddle point 62 of the left-hand side of the second vertebra 26. Accurate guidance of the implantation angle of the guide wire 668 into the saddle point 62 of the left-hand side of the second vertebra 26 may be somewhat less important than in the corresponding saddle point 42 of the first vertebra 24.

After the guide wires 668 have been implanted into the saddle points 62 of the second vertebra 26, the saddle points 62 may be reamed in a manner similar to that of the saddle points of the first vertebra 42. As with the saddle points 42, the primary and secondary reamers 70, may be used.

Figure 36:
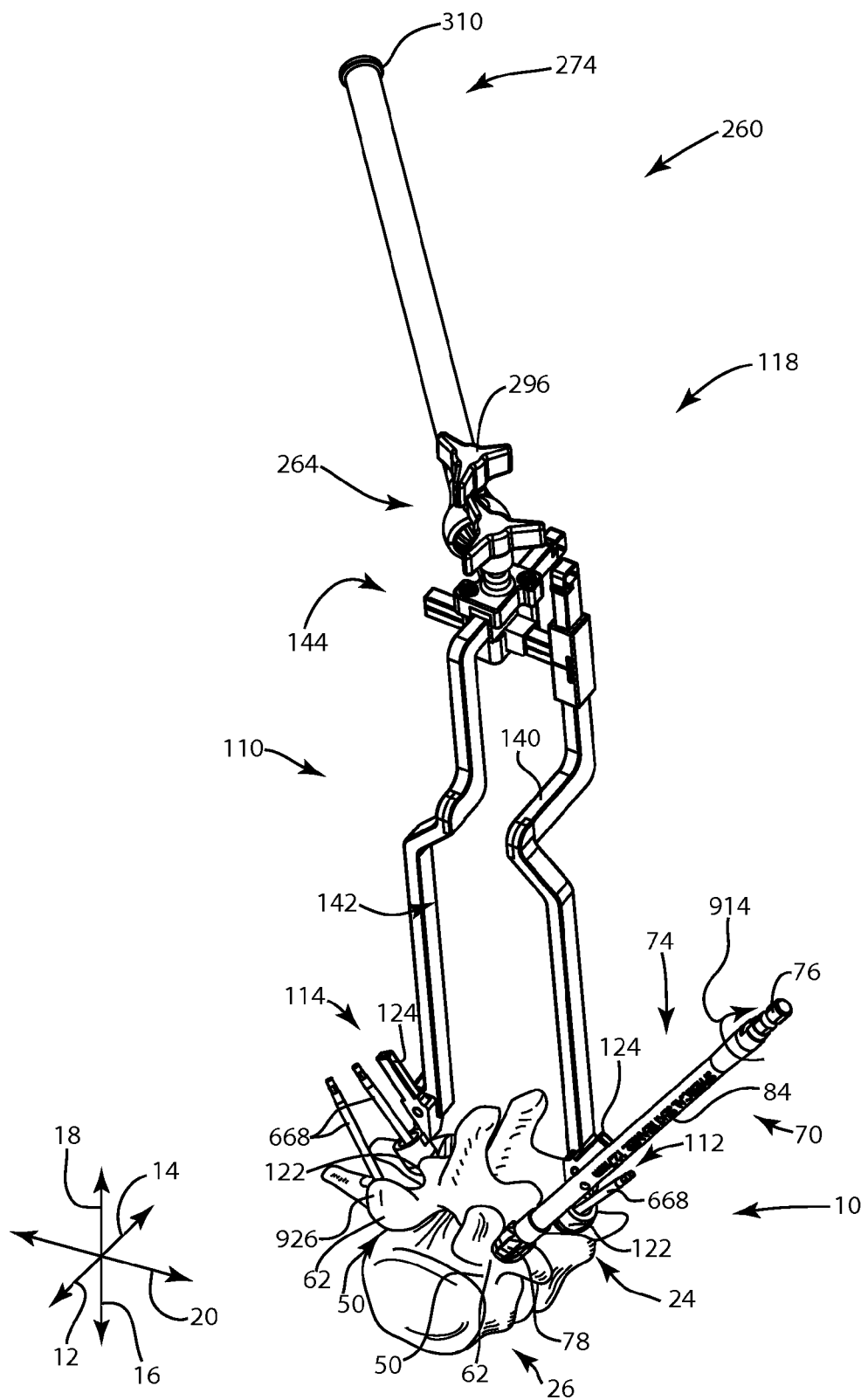
FIG. 36 is a perspective view of the L4 and L5 vertebrae with the L4 and L5 guide wires, frame, and stationary external support in place, with one pedicle of the L4 vertebra partially reamed to provide a roughened semispherical surface, and the primary reamer positioned to ream the other pedicle of the L4 vertebra.

Referring to FIG. 36, a perspective view illustrates the first and second vertebrae 24, 26 with the guide wires 668, frame 110, and stationary external support 260 in place, and with the primary reamer 70 positioned to ream the left-hand saddle point 62 of the second vertebra 26. As shown, the primary reamer 70 has been registered on the guide wire 668 of the left-hand saddle point 62 by inserting the guide wire 668 into the bore 88 of the primary reamer 70, thereby registering the primary reamer 70 with respect to the saddle point 62. Thus, motion of the primary reamer 70 is constrained to rotation about the axis of the guide wire 668 and motion along the guide wire 668.

The primary reamer 70 is coupled at the torque interface 76 to a handle, motor, or the like (not shown). The primary reamer 70 rotates along the direction 914 such that the cutting flanges 92 scrape away bone tissue from around the saddle point 62. The primary reamer 70 is advanced into the pedicle 50 until the flat surface 90 abuts the bone immediately surrounding the guide wire 668. The primary reamer 70 is then unable to advance further into the bone, and is withdrawn to leave a roughened semispherical surface 926, as shown on the right-hand side of the second vertebra 26. The roughened semispherical surface 926 has a plateau (not visible in FIG. 36) immediately surrounding the guide wire 668, where the primary reamer 70 was unable to remove the bone tissue.

Figure 37:
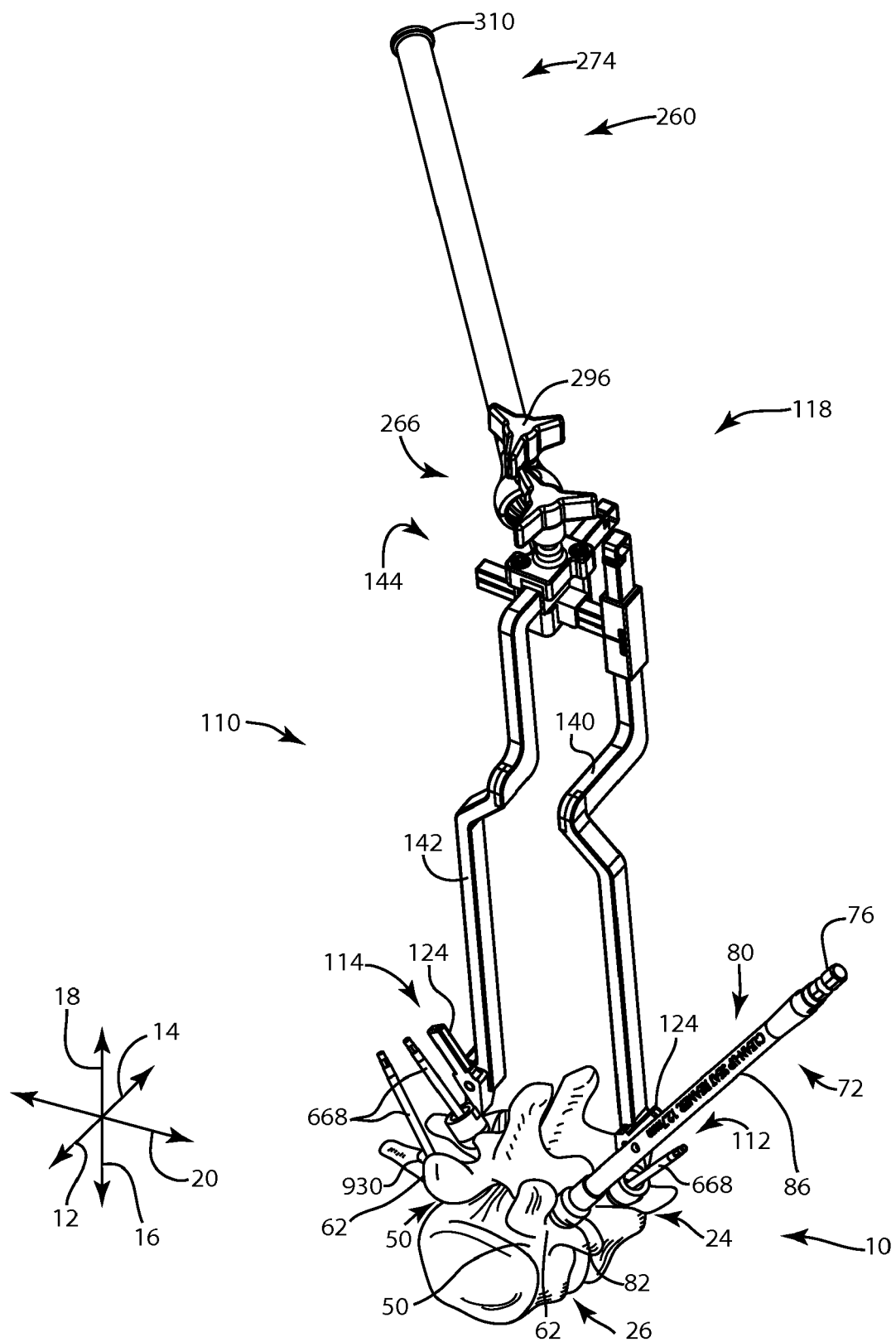
FIG. 37 is a perspective view of the L4 and L5 vertebrae with the L4 and L5 guide wires, frame, and stationary external support in place, with one pedicle of the L4 vertebra fully reamed to provide a semispherical surface, and the secondary reamer positioned to ream the other pedicle of the L4 vertebra.

Referring to FIG. 37, a perspective view illustrates the first and second vertebrae 24, 26 with the guide wires 668, frame 110, and stationary external support 260 in place, and with the secondary reamer 72 positioned to complete reaming of the left-hand saddle point 62. As described previously, the dome 102 of the secondary reamer 72 is advanced into the roughened semispherical surface 926. The dome 102 does not remove bone tissue, but the central teeth 100 remove the plateau (not visible) to leave a semispherical interface 930 at the saddle point 62.

After the semispherical interfaces 930 have been formed at the saddle points 62 of the second vertebra 26, The guide wires 668 implanted in the saddle points 62 are no longer needed and may be removed. The pedicles 50 of the second vertebra 26 may then be tapped and the pedicle screws 670 may be inserted into the resulting tapped holes.

Figure 38:
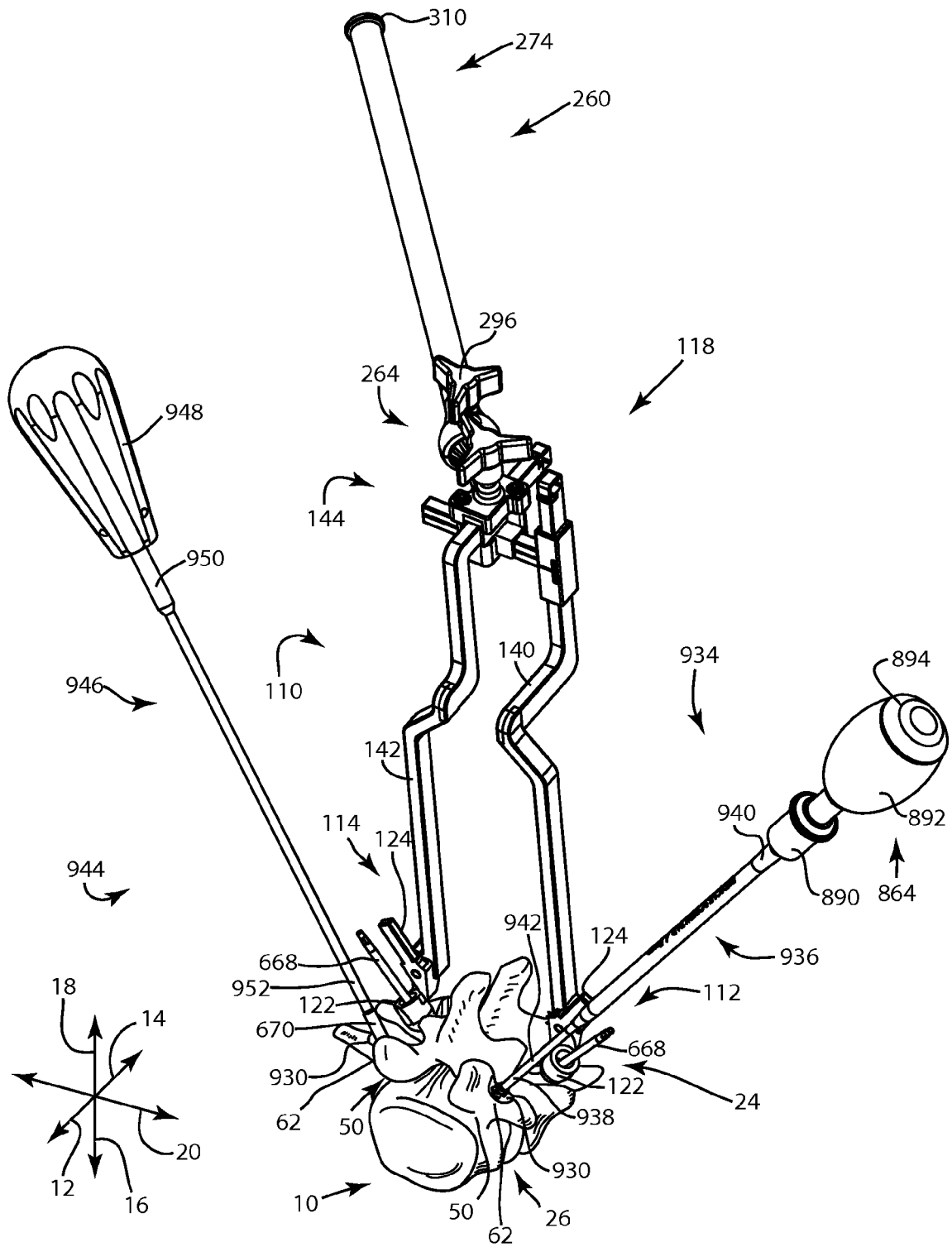
FIG. 38 is a perspective view of the L4 and L5 vertebrae with the L5 guide wires, frame, and stationary external support in place, with a pedicle tapping tool positioned to tap one pedicle of the L4 vertebra, and a screw insertion tool positioned to insert a pedicle screw in the other pedicle of the L4 vertebra.

Referring to FIG. 38, a perspective view illustrates the first and second vertebrae 24, 26 with the guide wires 668, frame 110, and stationary external support 260 in place, and with tools positioned to tap and drive a pedicle screw 670 into the pedicles 50 of the second vertebra 26. More precisely, a pedicle tapping tool 934 is positioned to tap the pedicle 50 of the left-hand side of the second vertebra 26.

The pedicle tapping tool 934 may have any of a variety of configurations, some of which may be known in the art of spinal fusion. According to one example, the pedicle tapping tool 934 has a shaft 936, a tapping head 938 at one end of the shaft 936, and a grip member 864 on the opposite end of the shaft 936. The grip member 864 may be substantially the same as the grip member 864 of the guide wire inserter 860 of FIGS. 22 and 35, and may thus be used to manually impart torque to the shaft 936. The tapping head 938 has a plurality of threads (not visible in FIG. 38). The shaft 936 has a coupling end 940 retained within the coupling 890 of the grip member 864, and a working end 942 either permanently or removably coupled to the tapping head 938.

The end (not shown) of the tapping head 938 is inserted into the canal left by removal of the guide wire 668. Then, the tapping head 938 is rotated clockwise to cause the threads of the tapping head 938 to cut a threaded path into the wall of the canal. The tapping head 938 may be rotated counterclockwise to withdraw the threads from the canal, thereby leaving a tapped hole in the pedicle 50 of the second vertebra 26. The tapped hole may also be sounded through the use of a sounder (not shown) having any of a variety of known configurations, if desired.

A screw insertion tool 944 is positioned to drive the pedicle screw 670 into the pedicle 50 of the right-hand side of the second vertebra 26. The right-hand side pedicle 50 has already been tapped and sounded, and is therefore ready to receive the pedicle screw 670. The screw insertion tool 944 has a shaft 946 and a grip 948 coupled to one end of the shaft 946. The shaft 946 has a grip attachment end 950 coupled to the grip 948 and a working end 952, which may have a hexagonal shape designed to be insertable into the torque receiver 792 of the pedicle screw 670.

The end (not shown) of the pedicle screw 670 is inserted into the tapped hole of the pedicle 50. Then, the grip 948 is rotated clockwise to cause the threaded end 790 of the pedicle screw 690 to engage the threads of the tapped hole. The working end 952 may then be drawn free of the torque receiver 792 of the pedicle screw 670. The pedicle screw 670 may remain implanted in the pedicle 50, with the shank 788 and a portion of the threaded end 790 exposed.

After the pedicle screws 670 have been implanted in the pedicles 50 of the second vertebra 26, the inferior resection tool 660 may be used to guide resection of the inferior facet 60 of the left-hand side of the second vertebra 26. The registration member 662 and the anchoring member 664 of the inferior resection tool 660 may be selected based on the selection of the superior and inferior prostheses. The inferior resection tool 660 may then be assembled and registered on the frame 110 by sliding the bore 686 of the registration interface 680 over the guide post 124 of the first anchor 112 of the frame 110.

Simultaneously, the first, second, and third joints 802, 804, 806 may be actuated to move the anchoring feature 700 with respect to the registration interface 680 such that the anchoring feature 700 is able to slide into engagement with the semispherical interface 930 and the pedicle screw 670 of the left-hand side of the second vertebra 26. The anchoring feature 700 may be attached to the semispherical interface 930 via the castle nuts 672 through the use of a nut tightening tool.

Figure 39:
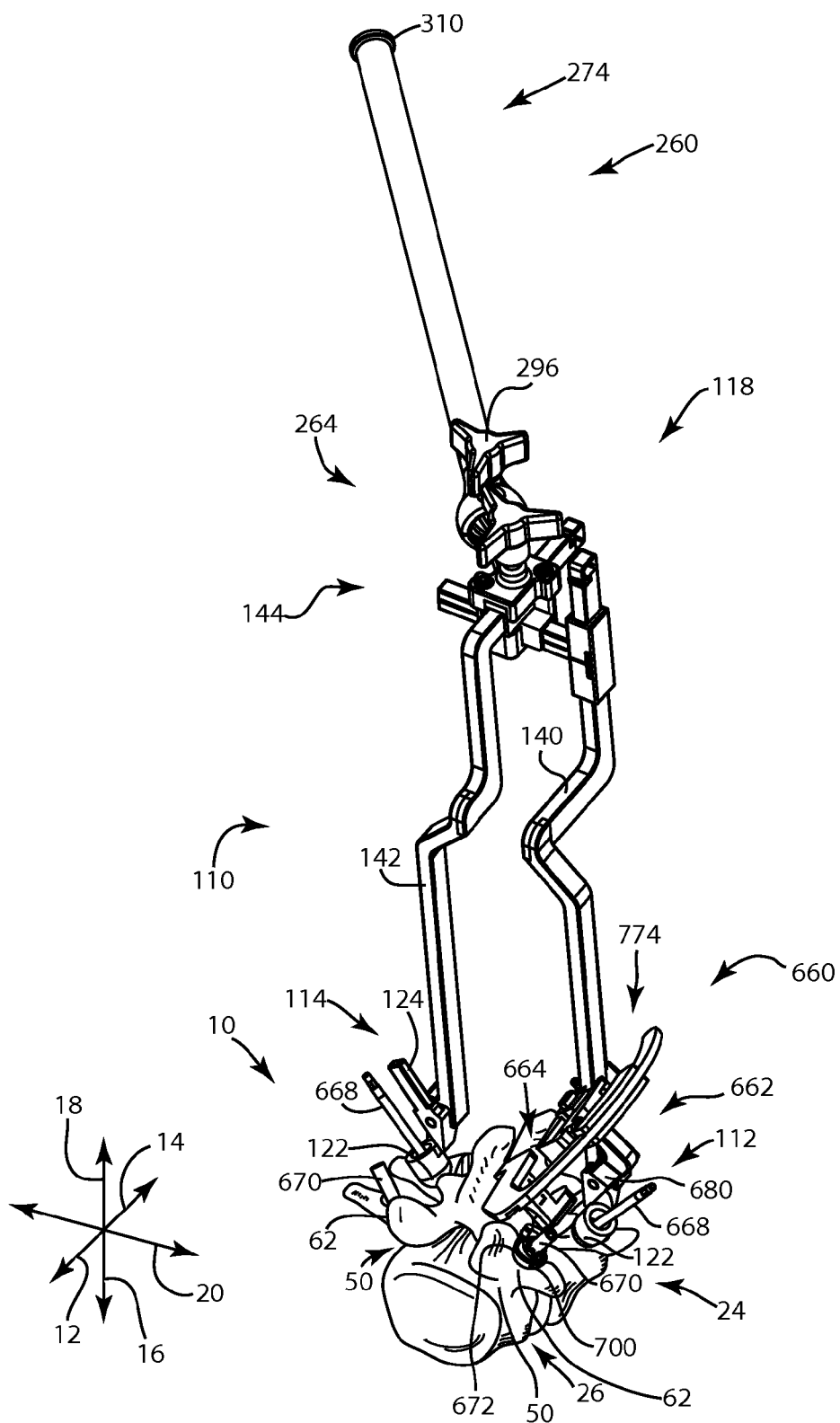
FIG. 39 is a perspective view of the L4 and L5 vertebrae with the L5 guide wires, L4 pedicle screws, frame, and stationary external support in place, with one of the inferior facets of the L4 vertebra resected, and with the inferior resection tool registered to the frame and coupled to the L4 vertebra via the castle nut to facilitate resection of the other inferior facet of the L4 vertebra.

Referring to FIG. 39, a perspective view illustrates the first and second vertebrae 24, 26 with the guide wires 668, pedicle screws 670, frame 110, and stationary external support 260 in place, and with the inferior resection tool 660 registered to the frame 110 and anchored to the second vertebra 26. The joints 802, 804, 806 of the inferior resection tool 660 have moved to positions in which the relative positions and orientations of the registration interface 680 and the anchoring feature 700 are adapted to the morphology of the spine 10. Thus, the slot 714 of the guide feature 702 of the inferior resection tool 660 is positioned at the proper orientation to guide a reciprocating blade of a cutting tool (not shown) to resect the inferior facet 60 of the left-hand side of the second vertebra 26. The cutting tool may be an oscillating saw or another cutting tool designed specifically for spinal applications.

Figure 40:
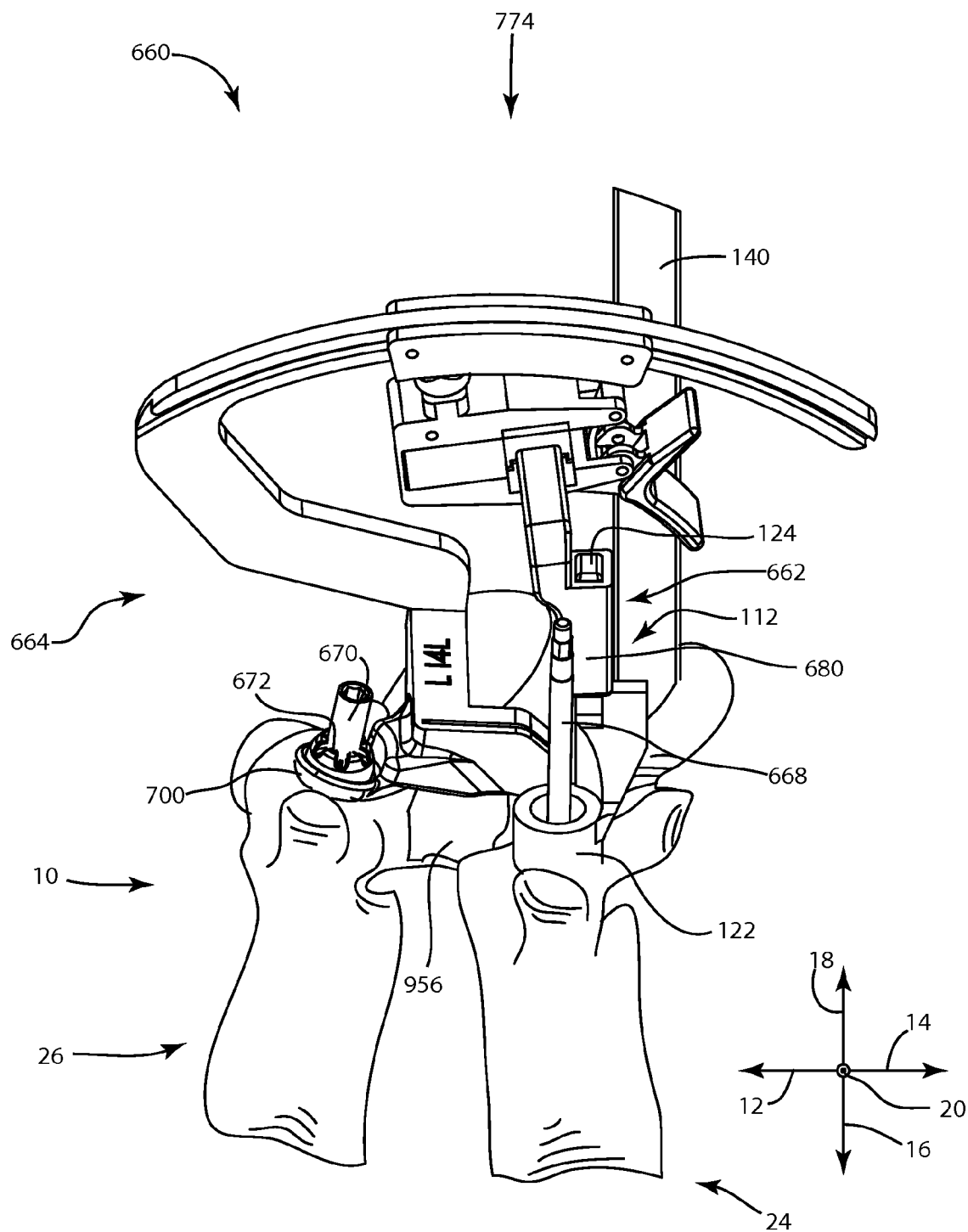
FIG. 40 is a lateral view of the L4 and L5 vertebrae with the L5 guide wires, L4 pedicle screws, castle nut, frame, stationary external support, and inferior resection tool in place.

Referring to FIG. 40, a lateral view illustrates the first and second vertebrae 24, 26 with the guide wires 668, pedicle screws 670, frame 110, and stationary external support 260 in place, and with the inferior resection tool 660 registered to the frame 110 and anchored to the second vertebra 26. Before the inferior facet 60 is resected, the lever 734 may be actuated into the locked position to lock the first joint 802 in place to stabilize the position and orientation of the slot 714. In alternative embodiments, the second and third joints 804, 806 may be lockable in addition to or in the alternative to the first joint 802 to stabilize the position and orientation of the slot 714.

After the cutting tool has been used to resect the inferior facet 60, the castle nuts 672 may then be removed, and the inferior resection tool 660 may be removed from the spine 10. If the surgeon decides not to drive the oscillating saw completely through the facet 58, to avoid entry into the central canal of the spine 10, an osteotome or other similar tool may be used to complete resection of the inferior facets 60 of the second vertebra 26. Manual tools may be required to complete resection of the medial margins of the inferior facets 58 of the second vertebra 26. An inferior resection surface 956 has then been formed on each side of the second vertebra 26, as shown in FIG. 40.

After the inferior facets 60 of the second vertebra 26 have been resected, the superior facets 38 of the first vertebra 24 are relatively easily accessible. Thus, the superior facet 38 of the left-hand side of the first vertebra 24 may be resected through the use of the kit 510 of superior cutting tools.

The cutting guide 630 is selected from a kit of multiple cutting guides based on the selection of the superior facet prosthesis. The cutting guide 630 may be registered on the frame 110, and the short, long, and curved cutting tools 512, 514, 516 may be sequentially registered on the cutting guide 630 to perform resection of the superior facet 38. The short cutting tool 512 may be used first to commence forming a resection surface, then the curved cutting tool 516 may be used to broaden the resection surface, and then the long cutting tool 514 may be used to further broaden the resection surface.

Figure 41:
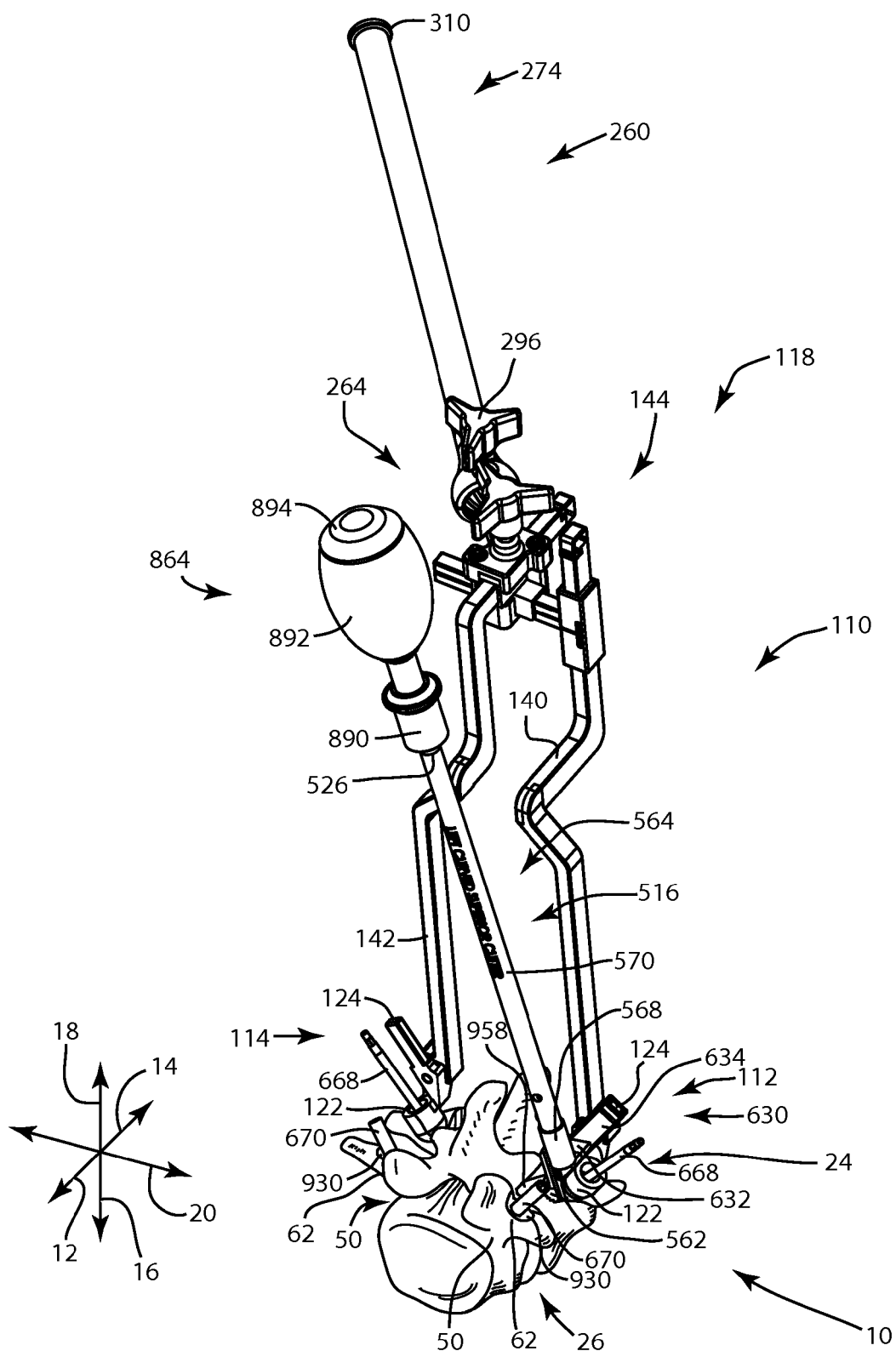
FIG. 41 is a perspective view of the L4 and L5 vertebrae with the L5 guide wires, L4 pedicle screws, frame, and stationary external support in place, with one superior facet of the L5 vertebra partially resected, and with the curved cutting tool registered to the frame to facilitate resection of the other superior facet of the L5 vertebra.

Referring to FIG. 41, a perspective view illustrates the first and second vertebrae 24, 26 with the guide wires 668, pedicle screws 670, frame 110, and stationary external support 260 in place, and with the cutting guide 630 registered on the frame 110 and the curved cutting tool 516 registered on the cutting guide 630 to carry out resection of the superior facet 38 of the left-hand side of the first vertebra 24. The registration interface 634 of the cutting guide 630 is registered on the first anchor 112 of the frame 110 by sliding the bore 650 of the registration interface 634 over the guide post 124 of the first anchor 112. The post 652 of the registration feature 636 of the cutting guide 630 then protrudes at an angle offset from that of the guide post 124. The post 652 extends substantially perpendicular to the plane along which resection of the superior facet 38 is to be carried out.

The curved cutting tool 516 is registered on the cutting guide 630, and thereby registered on the frame 110, by sliding the bore 600 of the registration interface 532 of the curved cutting tool over the post 652. Relative motion between the curved cutting tool 516 and the first vertebra 24 is then limited to translation along the post 652 and rotation about the axis of the post 652. As shown, the grip member 864 may be coupled to the curved cutting tool 516 by inserting the torque receiver 526 of the shaft 560 of the curved cutting tool 516 into the coupling 890 of the grip member 864.

The grip 892 may thus be grasped and rotated by hand in reciprocating fashion, while slight pressure is applied to urge the cutting surface 576 of the curved cutting tool 516 against the surface of the bone, to remove bone tissue from the superior facet 38. As bone tissue is removed, the bore 600 progresses further along the post 652 until the distal cap 568 of the shaft 560 of the curved cutting tool 516 abuts the shoulder 646 of the main body 632 of the cutting guide 630.

At the time the curved cutting tool 516 is used, the short cutting tool 512 has already been applied in a similar manner. The short cutting tool 512 has been rotated clockwise such that the cutting surface 536 of the short cutting tool 512 sweeps from the foraminal space until the arm 534 of the short cutting tool 512 contacts the first anchor 112 of the frame 110. The curved cutting tool 516 is used in a similar manner to simply broaden the radius of the resection surface and to extend the resection surface around the semispherical surface 128 of the first anchor 112. After the curved cutting tool 516 is applied, the long cutting tool 514 may be used in a similar manner to further broaden the resection surface. The resulting resection surface, which is a superior resection surface 958, is substantially planar and continuous despite the use of multiple different cutting tools 512, 514, 516 to form it.

Figure 42:
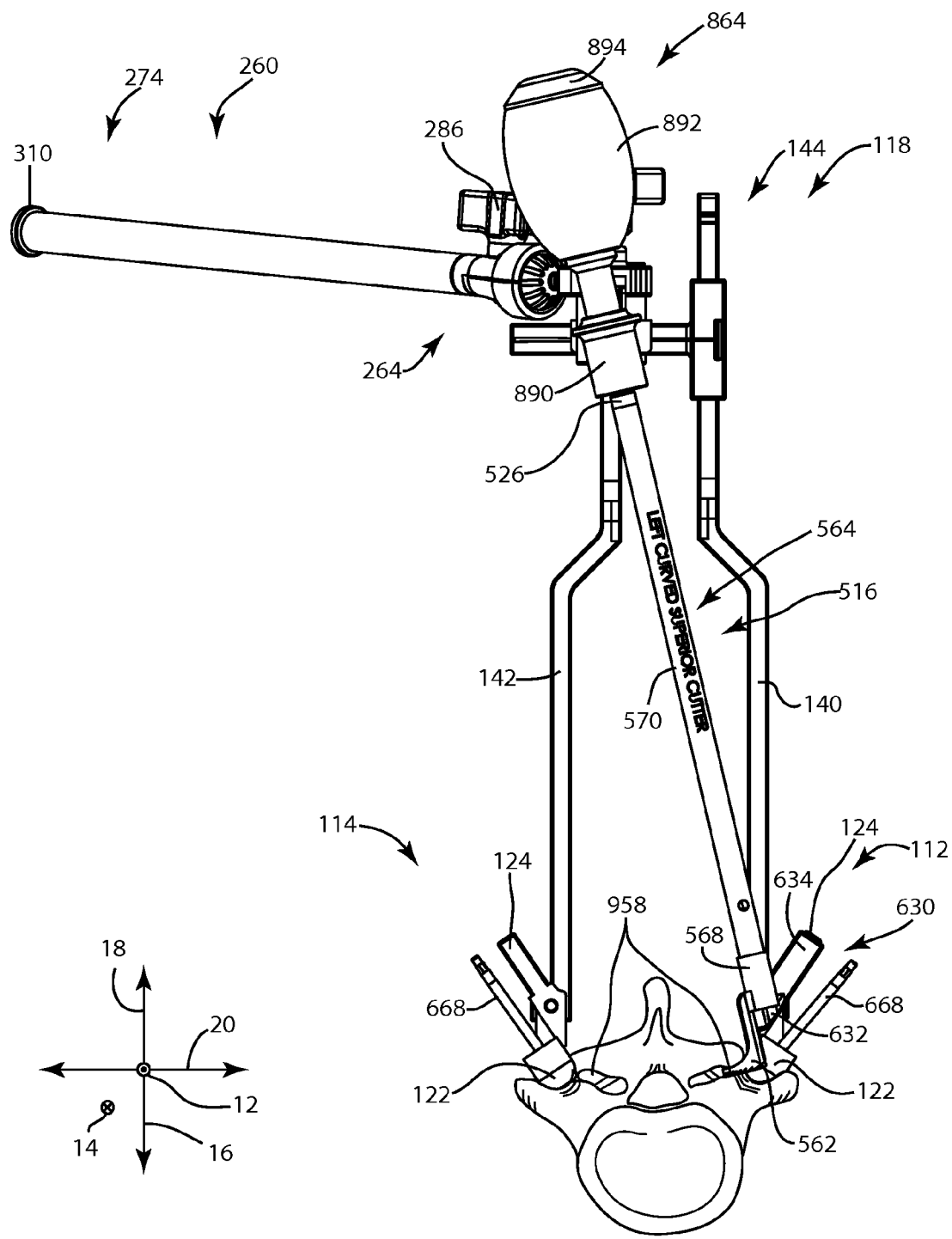
FIG. 42 is a cephalad view of the L5 vertebra with the L5 guide wires, frame, stationary external support, and curved cutting tool in place.

Referring to FIG. 42, a cephalad view illustrates the first vertebra 24 with the guide wires 668, pedicle screws 670, frame 110, and stationary external support 260 in place, and with the cutting guide 630 registered on the frame 110 and the curved cutting tool 516 registered on the cutting guide 630 to carry out resection of the superior facet 38 of the left-hand side of the first vertebra 24. FIG. 42 provides an edge view of the superior resection surface 958 formed through the use of the cutting tools 512, 514, 516. As in other drawings previously described, the same operation has already been performed on the right-hand side of the first vertebra 24.

After the short, long, and curved cutting tools 512, 514, 516 have been applied and removed in sequence, the cutting guide 630 and the frame 110 may be removed, and the seat cutting tool 518 may be used. The seat cutting tool 518 does not register on the cutting guide 630 and is not designed to contribute to formation of the superior resection surface 958. Rather, the seat cutting tool 518 provides a flat surface proximate the semispherical interfaces 920 of the saddle points 42 of the first vertebra 24. The flat surface formed by the seat cutting tool 518 may correspond to a flat surface of the selected superior facet prosthesis, and may help prevent rotation of the selected superior facet prosthesis against the first vertebra 24 after the selected superior facet prosthesis has been attached to the first vertebra 24.

Figure 43:
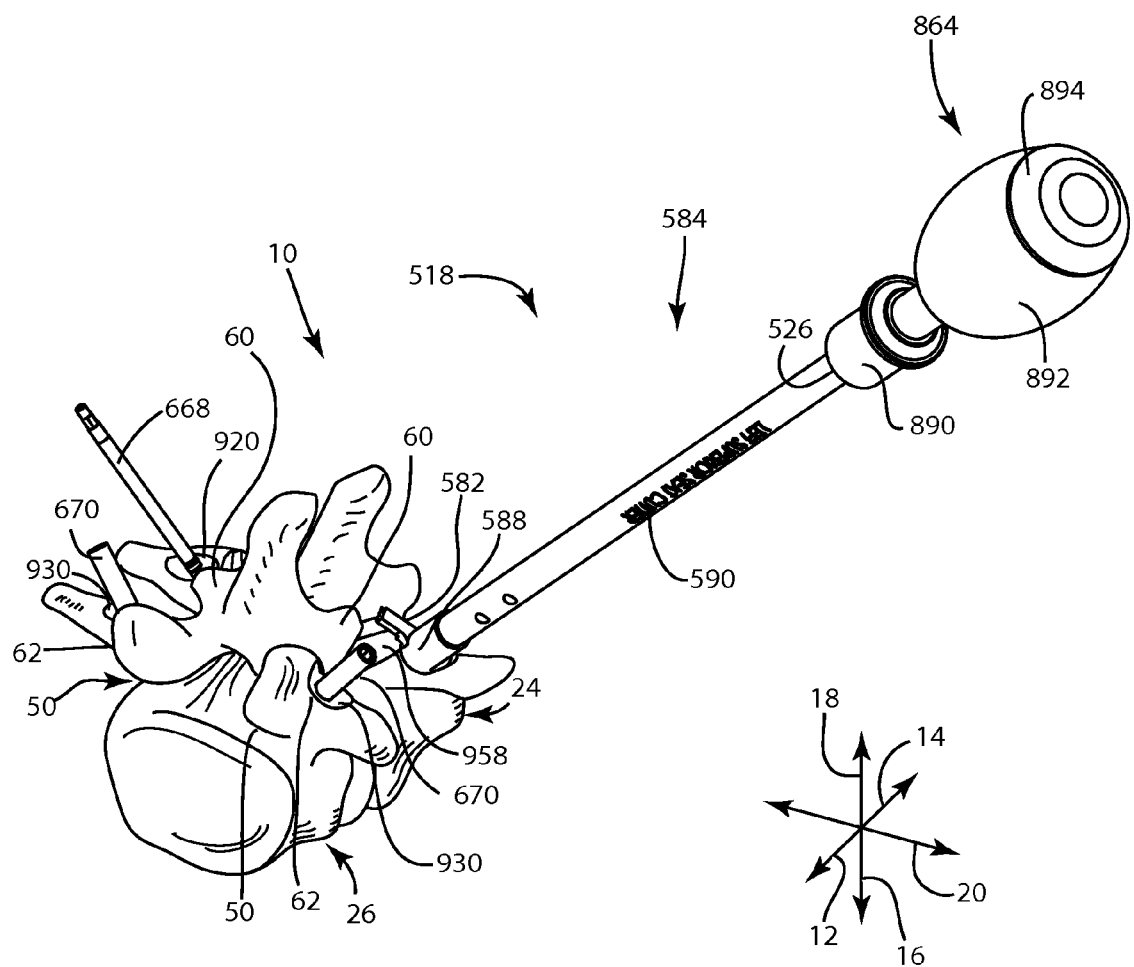
FIG. 43 is a perspective view of the L4 and L5 vertebrae with the L5 guide wires and L4 pedicle screws in place, with one superior facet of the L5 vertebra fully resected, and with the seat cutting tool registered to one of the guide wires to facilitate further resection of the other superior facet of the L5 vertebra.

Referring to FIG. 43, a perspective view illustrates the first and second vertebrae 24, 26 with the guide wires 668 and the pedicle screws 670 in place, and with the seat cutting tool 518 positioned to provide a flat surface proximate the semispherical interface 920 of the left-hand side of the first vertebra 24. The seat cutting tool 518 is registered to the guide wire 668 extending from the saddle point 42 of the left-hand side of the first vertebra 24.

More precisely, the registration interface 592 of the shaft 580 of the seat cutting tool is registered on the guide wire 668 by sliding a bore (not visible in FIG. 43) of the shaft over the exposed portion of the guide wire 668. Relative motion between the seat cutting tool 518 and the first vertebra 24 is thus constrained to translation along the guide wire 668, or rotation about the axis of the guide wire 668. The guide wire 668 is substantially collinear with an axis of the corresponding pedicle 30; accordingly, the seat cutting tool 518 is registered to form a flat surface substantially perpendicular to the axis of the pedicle 30.

Figure 44:
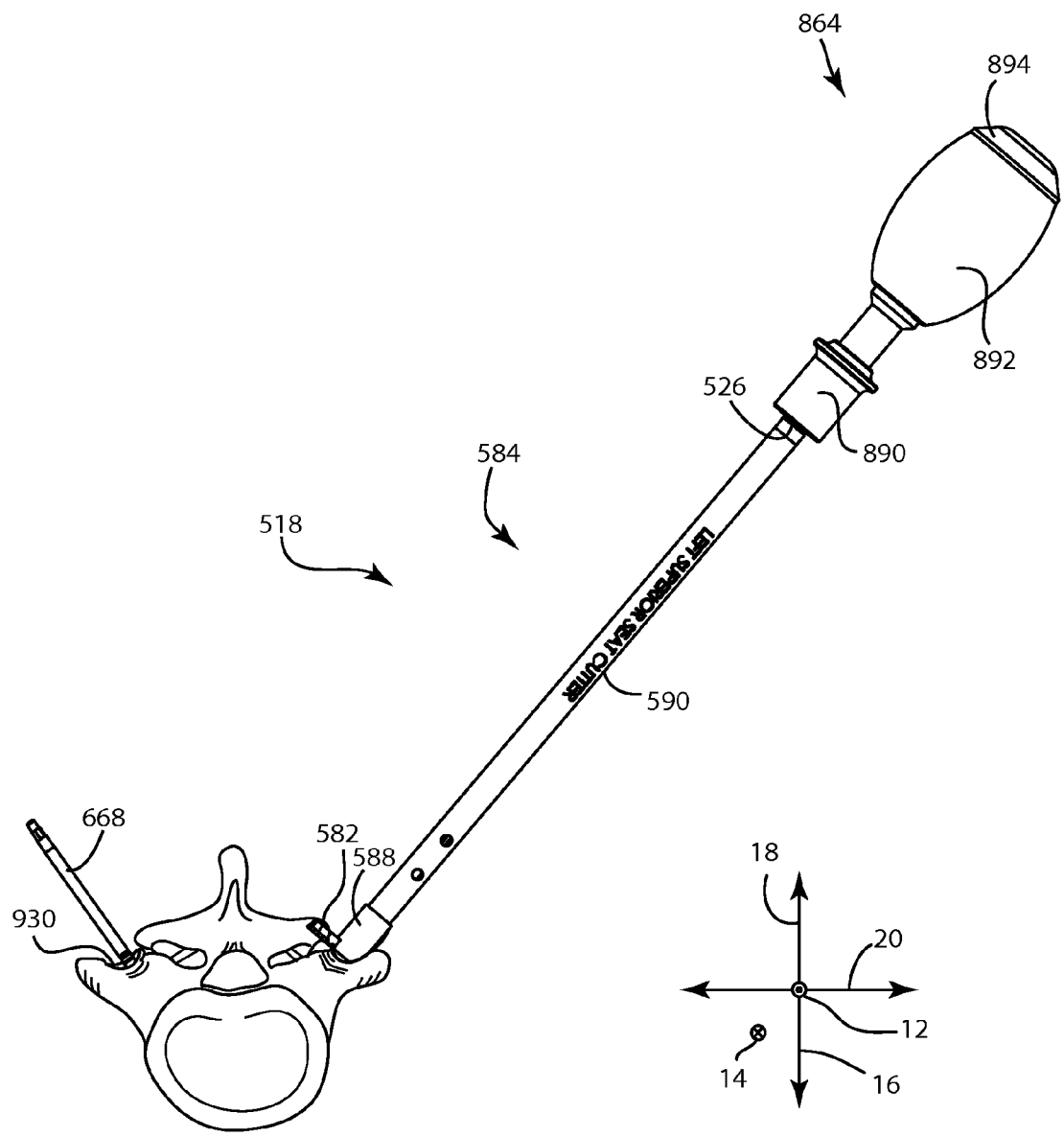
FIG. 44 is a cephalad view of the L5 vertebra with the L5 guide wires and the seat cutting tool in place.

Referring to FIG. 44, a cephalad view illustrates the first vertebra 24 with the guide wires 668 and the pedicle screws 670 in place, and with the seat cutting tool 518 positioned to provide a flat surface proximate the semispherical interface 920 of the left-hand side of the first vertebra 24. The size of the flat surface formed by the seat cutting tool 518 varies according to the selection of the superior facet prosthesis. In FIG. 44, the seat cutting tool 518 has little bone to resect because the superior resection surface 958 extends substantially to the edge of the semispherical interface 920. However, in alternative embodiments, the seat cutting tool 518 may resect away more bone tissue to provide a more distinct flat surface.

After resection of the superior facets 38 of the first vertebra 24 has been completed, the guide wires 668 may be removed from the pedicles 30 of the first vertebra 24. The remaining canals may be tapped, and pedicle screws 670 may be inserted into the resulting tapped holes in preparation for attachment of facet joint prostheses to the vertebrae 24, 26.

Figure 45:
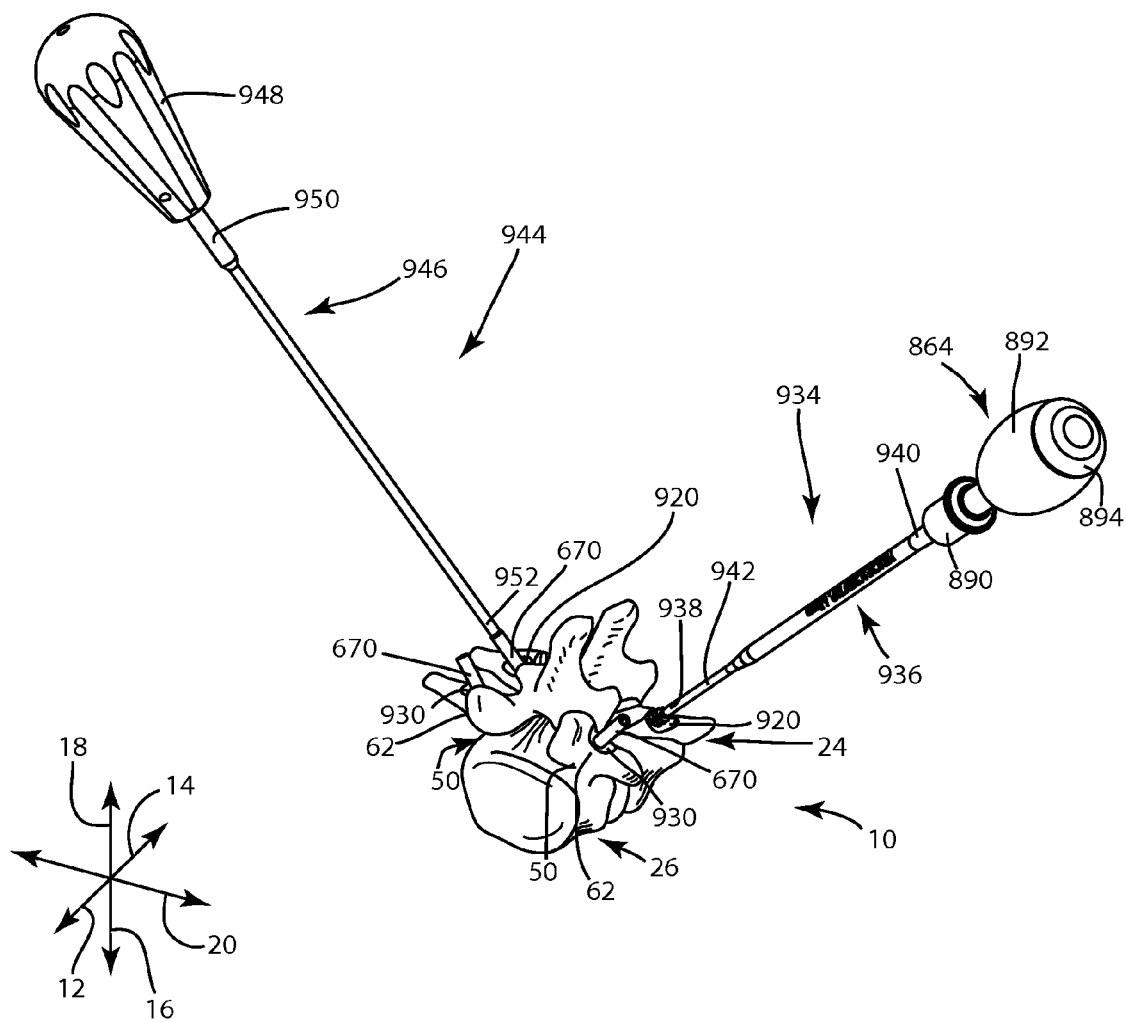
FIG. 45 is a perspective view of the L4 and L5 vertebrae with the L4 pedicle screws in place, with a pedicle tapping tool positioned to tap one pedicle of the L5 vertebra, and the screw insertion tool positioned to insert a pedicle screw in the other pedicle of the L5 vertebra.

Referring to FIG. 45, a perspective view illustrates the first and second vertebrae 24, 26 with the pedicle screws 670 of the second vertebra 26 in place. Furthermore, in FIG. 45, the pedicle tapping tool 934 is positioned to tap the pedicle 30 of the left-hand side of the first vertebra 24, and the screw insertion tool 944 is positioned to insert one of the pedicle screws 670 into the pedicle 30 of the right-hand side of the first vertebra 24.

The end (not shown) of the tapping head 938 is inserted into the canal left by removal of the guide wire 668 from the left-hand pedicle 30 of the first vertebra 24. Then, the tapping head 938 is rotated clockwise to cause the threads of the tapping head 938 to cut a threaded path into the wall of the canal. The tapping head 938 may be rotated counterclockwise to withdraw the threads from the canal, thereby leaving a tapped hole in the pedicle 30 of the first vertebra 24. The tapped hole may also be sounded through the use of a sounder (not shown) having any of a variety of known configurations, if desired.

The right-hand side pedicle 30 has already been tapped and sounded, and is therefore ready to receive the pedicle screw 670. The end (not shown) of the pedicle screw 670 is inserted into the tapped hole of the pedicle 30. Then, the grip 948 is rotated clockwise to cause the threaded end 790 of the pedicle screw 690 to engage the threads of the tapped hole. The working end 952 may then be drawn free of the torque receiver 792 of the pedicle screw 670. The pedicle screw 670 may remain implanted in the pedicle 30, with the shank 788 and a portion of the threaded end 790 exposed.

After the pedicle screws 670 have been implanted in the pedicles 30 of the first vertebra 24, trial facet prostheses may be coupled to the vertebrae 24, 26 and checked for proper fit. If the fit is not proper, different prostheses may be selected and/or additional resections may be carried out on the first and second vertebrae 24, 26 to obtain the desired fit. Then, the selected facet prostheses may be coupled to the vertebrae 24, 26. The facet prostheses may be secured to the vertebrae 24, 26 via the castle nuts 672.

Figure 46:
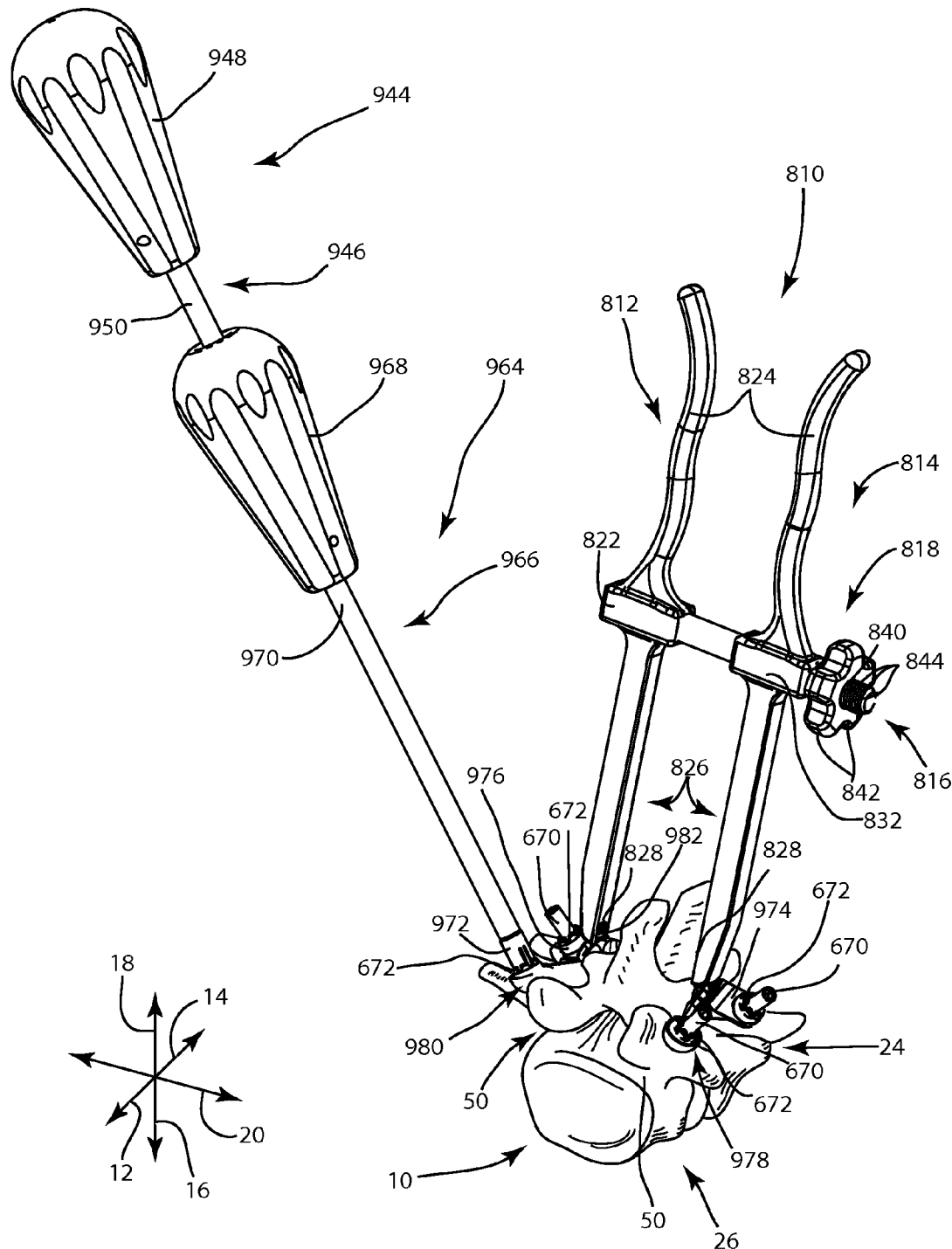
FIG. 46 is a perspective view of the L4 and L5 vertebrae with the L4 and L5 pedicle screws in place, with superior facet prostheses attached to replace the superior facets of the L5 vertebra via castle nuts, with inferior facet prostheses positioned to replace the inferior facets of the L4 vertebra, with a nut tightening tool positioned in cooperation with the screw insertion tool to secure one of the inferior facet prostheses to the L4 vertebra via a castle nut, and with the clamping tool positioned to retain the inferior facet prostheses.

Referring to FIG. 46, a perspective view illustrates the vertebrae 24, 26 with the pedicle screws 670 in place, with facet prostheses attached, with a nut tightening tool 964 positioned to secure the facet prostheses via the castle nuts 672. In FIG. 46, the clamping tool is used to clamp the inferior facet prostheses in place as they are secured to the second vertebra 26.

As shown, the nut tightening tool 964 is used in combination with the screw insertion tool 944 of FIG. 38. The nut tightening tool 964 has a shaft 966 and a grip 968, which may be shaped similarly to the grip 948 of the screw insertion tool 944, except that the grip 968 is cannulated to receive the shaft 946 of the screw insertion tool 944. The shaft 966 has a grip attachment end 970 attached to the grip 968 and a working end 972. The shaft 966 is hollow so that the shaft 946 of the screw insertion tool 944 is able to pass through the shaft 966 to reach the corresponding pedicle screw 670. Thus, a user may hold the grip 948 of the screw insertion tool 944 substantially stationary while rotating the grip 968 of the nut tightening tool 964 to tighten the corresponding castle nut 672 without significant rotation of the pedicle screw 670 about which the castle nut 672 is tightened. The castle nut 672 may engage exposed threads of the threaded end 790 of the pedicle screw 670.

In FIG. 46, a first superior prosthesis 974 and a second superior prosthesis 976 may be attached to the first vertebra 24, and a first inferior prosthesis 978 and a second inferior prosthesis 980 may be attached to the second vertebra 26. The prostheses 974, 976 replace the superior facets 38 of the first vertebra 24 that were resected away previously, while the prostheses 978, 980 replace the inferior facets 60 of the second vertebra 26 that were also resected away previously. Although FIG. 46 illustrates full, bi-lateral replacement of both of the facet joints 64 of the vertebrae 24, 26, the systems and methods of the present invention apply equally to unilateral replacement operations, or operations in which only superior or inferior facets are replaced.

The process of tightening the castle nuts 672 to secure the inferior prostheses 978, 980 transmits torque to the inferior prostheses 978, 980 that could potentially move them from their optimal positions. Accordingly, the clamping tool 810 may be used to hold the inferior prostheses 978, 980 in place while the corresponding castle nuts 672 are tightened using the nut tightening tool 964 and the screw insertion tool 944. More precisely, each of the inferior prostheses 978, 980 may have a projection 982 that extends posteriorly and terminates in a semispherical surface or the like. The projections 982 may be designed for use with a cross-link (not shown) that permanently stabilizes the inferior prostheses 978, 980.

As shown, the clamping tool 810 is positioned such that the grip portions 826 of the first and second clamping members 812, 814 are spread apart. The knob 818 has been rotated counterclockwise to retract the knob 818 along the threaded post 816, thereby permitting the clamping members 812, 814 to move apart. The projections 982 have been positioned in the recesses 828 of the grip portions 826, and the knob 818 has been rotated clockwise to draw the clamping members 812, 814 slightly together, thereby pressing the projections 982 snugly toward each other. As a result, the first and second inferior prostheses 978, 980 are held securely against the intervening bony body of the second vertebra 26. Thus, the clamping tool 810 prevents either of the inferior prostheses 978, 980 from rotating against the second vertebra 26.

Once the castle nuts 672 have all been tightened, the nut tightening tool 964 and the screw insertion tool 944 may be set aside, and the clamping tool may be removed by once again rotating the knob 818 counterclockwise to permit the clamping members 812, 814 to move apart sufficiently to withdraw the projections 982 from the recesses 828 of the grip portions 826. Attachment of the prostheses 974, 976, 978, 980 is now complete.

Figure 47:
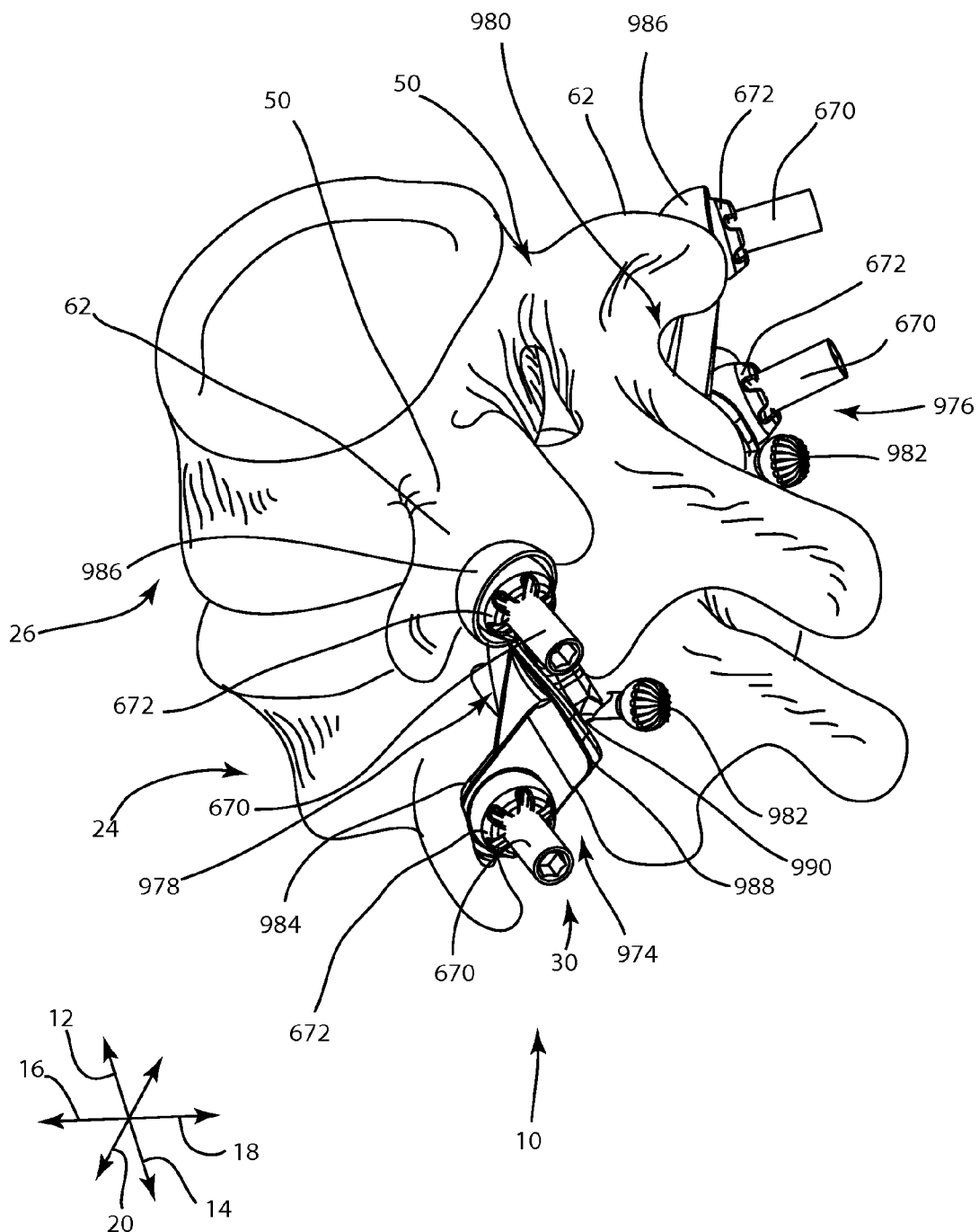
FIG. 47 is a perspective view of the L4 and L5 vertebra with the L4 and L5 pedicle screws, castle nuts, superior facet prostheses, and inferior facet prostheses in place.

Referring to FIG. 47, a perspective view illustrates the first and second vertebrae 24, 26, with the first and second superior prostheses 974, 976 attached to the first vertebra 24 and with the first and second inferior prostheses 978, 980 attached to the second vertebra 26. As illustrated in FIG. 47, each of the superior prostheses 974, 976 has an anchoring surface 984 with a generally semispherical shape that fits within the corresponding semispherical interface 920 of each saddle point 42 of the first vertebra 24. Similarly, each of the inferior prostheses 978, 980 has an anchoring surface 986 with a generally semispherical shape that fits within the corresponding semispherical interface 930 of each saddle point 62 of the second vertebra 26.

Additionally, each of the superior prostheses 974, 976 has an articulating surface 988 that faces generally medially (i.e., inward). The articulating surfaces 988 are generally trough-shaped to replicate the natural shapes of the superior facets 38 of the first vertebra 24. Each of the inferior prostheses 978, 980 has an articulating surface 990 that faces generally laterally (i.e., outward). The articulating surfaces 990 are generally semispherical to replicate the natural shapes of the inferior facets 60 of the second vertebra 26. Accordingly, the articulating surfaces 988, 990 may articulate against each other to provide ball-in-trough motion characteristic of the natural facet joints 64 of the vertebrae 24, 26.

Figure 48:
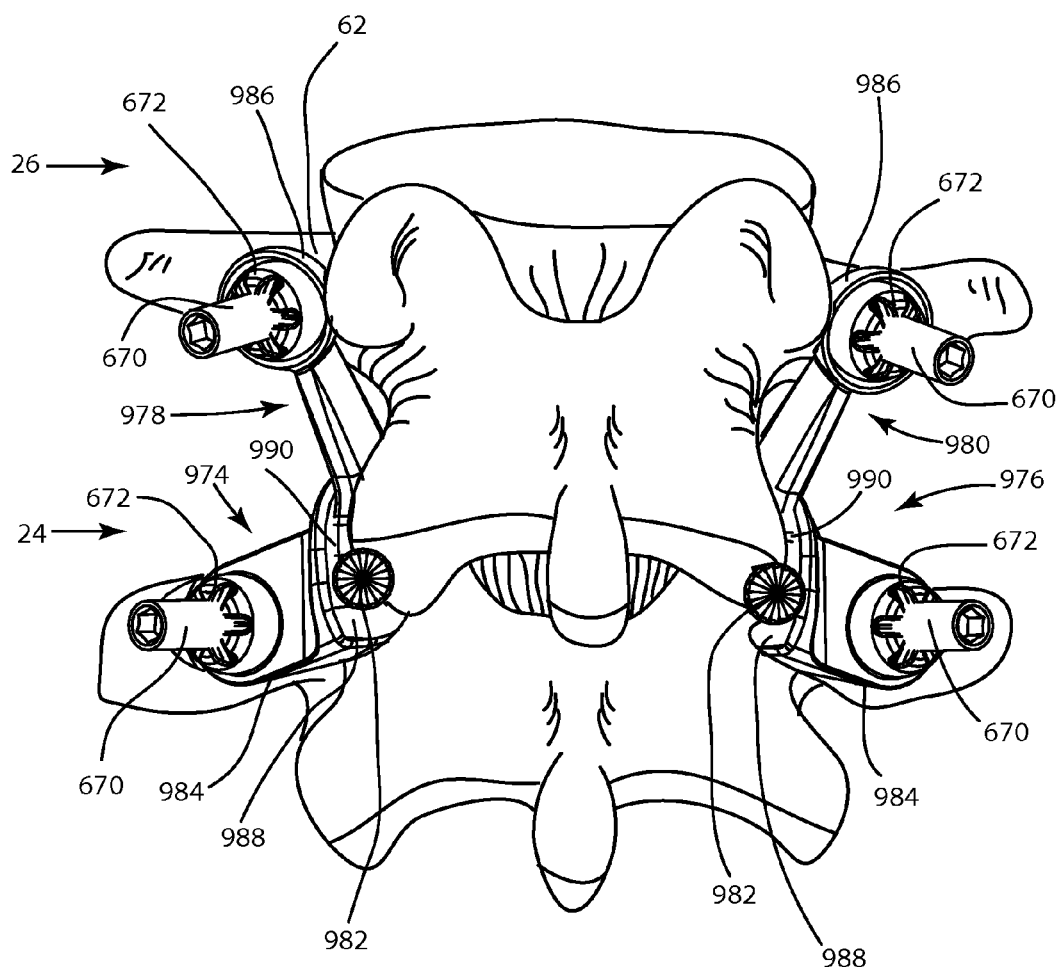
FIG. 48 is a posterior view of the L4 and L5 vertebra with the L4 and L5 pedicle screws, castle nuts, superior facet prostheses, and inferior facet prostheses in place.
Figure 48:

Referring to FIG. 48, a posterior view illustrates the first and second vertebrae 24, 26, with the first and second superior prostheses 974, 976 attached to the first vertebra 24 and with the first and second inferior prostheses 978, 980 attached to the second vertebra 26. The articulating surfaces 988, 990 are more clearly visible in FIG. 48. If desired, a cross-link (not shown) may be attached to the projections 982 of the inferior prostheses 978, 980 to help keep them in place. Such a cross-link may, if desired, be attached to the spinous process 56 of the second vertebra 26, or separate linking structures may attach the projections 982 to the spinous process 56 to provide additional stability.

As a result of the manner in which the prostheses 974, 976, 978, 980 articulate against each other, the spine 10 maintains its natural kinematics in flexion/extension, lateral bending, and rotation, or twisting. Additionally, the loads on the vertebrae 24, 26 and on the surrounding bone structures, ligaments, and musculature will be substantially the same as before the facet joints 64 were replaced. Accordingly, the prostheses 974, 976, 978, 980 may correct facet joint problems without disrupting the normal functioning of the spine 10. Furthermore, through the use of the various surgical instruments and methods presented herein, prostheses 974, 976, 978, 980 may be accurately selected and safely attached to vertebrae of patients having a wide variety of spinal morphologies.

The present invention has particular relevance to surgery, and more particularly to facet joint replacement. However, the principles, structures, and methods of the present invention may also be extended to other fields including measurement and resection of bone for installation of other implants such as hip and knee implants.

The present invention may be embodied in other specific forms without departing from its spirit or essential characteristics. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for conducting surgery on a spine of a patient, the system comprising:
a frame comprising:
a first anchoring feature configured to be coupled to a first bone portion of the patient;
a second anchoring feature configured to be coupled to a second bone portion of the patient, wherein the first and second bone portions are spaced apart from each other;
a first registration feature shaped to guide at least one surgical instrument; and
a bridging structure configured to couple the first and second anchoring features and the first registration feature together such that the second anchoring feature is positionable at any of a variety of positions with respect to the first anchoring feature, wherein the first and second anchoring features are configured to be coupled to pedicles of the spine;
wherein the bridging structure is configured to couple the first and second anchoring features and the first registration feature together such that the second anchoring feature is movable along three dimensions with respect to the first anchoring feature;
wherein the bridging structure comprises two arms, each of which has a first end and a second end, wherein the first ends are coupled to each other via three sliding joints that provide relative motion between the first ends along three orthogonal linear axes, and the second ends are coupled to the first and second anchoring features;
wherein the bridging structure further comprises a locking mechanism that is movable into a locked position in which the locking mechanism substantially prevents relative motion between the first ends along all three orthogonal linear axes in response to user actuation of a single element;
wherein the locking mechanism comprises a deformable component that cooperates in at least two of the sliding joints, wherein compression of a portion of the deformable component in the first of the two sliding joints causes deformation of a portion of the deformable component in the second of the two sliding joints which frictionally locks the second sliding joint.

2. The system of claim 1, further comprising the surgical instrument, wherein the surgical instrument comprises a measurement tool configured to measure a displacement between the first registration feature and a bony landmark of the spine.

3. The system of claim 1, further comprising the surgical instrument, wherein the surgical instrument comprises a resection tool configured to resect a facet of the spine.

4. The system of claim 1, wherein the first registration feature comprises a guide post that is receivable by a corresponding bore of the surgical instrument, the guide post having a non-circular cross section selected to substantially prevent rotation of the surgical instrument about an axis of the guide post.

5. The system of claim 1, wherein the frame further comprises an external anchoring feature attachable to a stationary external support to stabilize the frame.

6. The system of claim 1, wherein the frame further comprises a second registration feature, wherein the first and second registration features cooperate to enable performance of two distinct functions substantially symmetrically across a sagittal plane of the patient.

7. The system of claim 6, wherein the first and second anchoring features are configured to be attached coupled to the spine, on either side of the sagittal plane.

8. The system of claim 7, wherein the first and second bone portions comprise first and second pedicles of a vertebra of the spine, the system further comprising first and second guide wires configured to be driven into the first and second pedicles, wherein each of the first and second anchoring features comprises an opening sized to receive one of the guide wires so that the guide wires are able to guide positioning of the first and second anchoring features on the pedicles.

9. The system of claim 1, wherein each of the first and second anchoring features comprises a pivot feature, wherein the pivot features cooperate to permit rotation of the frame about an axis extending generally parallel to a displacement between the first and second pivot features.

10. The system of claim 9, wherein each of the pivot features comprises a semispherical surface shaped to seat within a correspondingly semispherical interface of each of the first and second pedicles.

11. The system of claim 1, further comprising at least one prosthesis shaped to replace at least a portion of a facet of a vertebra of the spine.

12. The system of claim 1, further comprising:
at least two prostheses shaped to replace two facets of a vertebra of the spine; and a cross-linking member attachable to the prostheses to couple the prostheses together.

13. A system for measuring a bony landmark on a spine of a patient, the system comprising:
a frame comprising:
an external anchoring feature;
a first registration feature shaped to guide at least one measurement tool configured to measure a displacement between the first registration feature and the bony landmark of the spine; and
a bridging structure configured to couple the external anchoring feature and the first registration feature together; and
a stationary external support comprising:
a fixed end attachable to a stationary structure; and
a grip configured to be coupled to the fixed end, wherein the grip is attachable to the external anchoring feature to restrict motion of the frame during measurement;
wherein the bridging structure comprises:
three sliding joints that provide relative motion along three orthogonal linear axes; and
a locking mechanism that is movable into a locked position in which the locking mechanism substantially prevents relative motion along all three orthogonal linear axes in response to user actuation of a single element;
wherein the locking mechanism comprises a deformable component that cooperates in at least two of the sliding joints, wherein compression of a portion of the deformable component in the first of the two sliding joints causes deformation of a portion of the deformable component in the second of the two sliding joints which frictionally locks the second sliding joint.

14. The system of claim 13, wherein the frame further comprises a second registration feature coupled to the first registration feature and the external anchoring feature via the bridging structure, wherein the first and second registration features cooperate to enable performance of two distinct measurement functions substantially symmetrically across a sagittal plane of the patient.

15. The system of claim 14, wherein the first and second registration features are spaced apart such that they can be positioned adjacent to first and second pedicles of a vertebra of the spine.

16. The system of claim 13, wherein the bridging structure is configured to couple the first registration feature and the external anchoring feature together such that the first registration feature is lockably movable with respect to the external anchoring feature along at least two dimensions.

17. The system of claim 16, wherein the bridging structure is configured to couple the first registration feature and the external anchoring feature together such that the first registration feature is lockably translatable along three orthogonal axes with respect to the external anchoring feature.

18. The system of claim 13, wherein the external anchoring feature comprises a generally spherical surface grippable by the grip in any of a plurality of relative orientations between the grip and the external anchoring feature.

19. The system of claim 18, wherein the stationary external support further comprises at least one joint that couples the grip to the fixed end such that the grip is lockably movable with respect to the fixed end.

20. The system of claim 13, further comprising at least one prosthesis shaped to replace at least a portion of a facet of a vertebra of the spine.

21. A system for conducting surgery on a spine of a patient, the system comprising:
   a left facet joint replacement prosthesis shaped to replace a left natural facet of the spine;
   a right facet joint replacement prosthesis shaped to replace a right natural facet of the spine; and
   a frame comprising:
      a first anchoring feature configured to be coupled to a first bone portion of the patient;
      a second anchoring feature configured to be coupled to a second bone portion of the patient, wherein the first and second bone portions are spaced apart from each other;
      a first registration feature shaped to guide at least one surgical instrument; and
      a bridging structure configured to couple the first and second anchoring features and the first registration feature together such that the second anchoring feature is positionable at any of a variety of positions with respect to the first anchoring feature, wherein the first and second anchoring features are configured to be coupled to pedicles of the spine to facilitate proper positioning of the left and right facet joint replacement prostheses;
   wherein the bridging structure comprises:
      three sliding joints that provide relative motion along three orthogonal linear axes; and
      a locking mechanism that is movable into a locked position in which the locking mechanism substantially prevents relative motion along all three orthogonal linear axes in response to user actuation of a single element;
      wherein the locking mechanism comprises a deformable component that cooperates in at least two of the sliding joints, wherein compression of a portion of the deformable component in the first of the two sliding joints causes deformation of a portion of the deformable component in the second of the two sliding joints which frictionally locks the second sliding joint.

22. The system of claim 21, further comprising the surgical instrument, wherein the surgical instrument comprises a measurement tool configured to measure a displacement between the first registration feature and a bony landmark of the spine.

23. The system of claim 21, further comprising the surgical instrument, wherein the surgical instrument comprises a resection tool configured to resect a facet of the spine.

24. The system of claim 21, wherein the first registration feature comprises a guide post that is receivable by a corresponding bore of the surgical instrument, the guide post having a noncircular cross section selected to substantially prevent rotation of the surgical instrument about an axis of the guide post.

25. The system of claim 21, wherein the bridging structure is configured to couple the first and second anchoring features and the first registration feature together such that the second anchoring feature is movable along three dimensions with respect to the first anchoring feature.

26. The system of claim 25, wherein the bridging structure comprises two arms, each of which has a first end and a second end, wherein the first ends are coupled to each other via three sliding joints that provide relative motion between the first ends along three orthogonal linear axes, and the second ends are coupled to the first and second anchoring features.

27. The system of claim 21, wherein the frame further comprises an external anchoring feature attachable to a stationary external support to stabilize the frame.

28. The system of claim 21, wherein the frame further comprises a second registration feature, wherein the first and second registration features cooperate to enable performance of two distinct functions substantially symmetrically across a sagittal plane of the patient.

29. The system of claim 28, wherein the first and second anchoring features are configured to be attached to the spine, on either side of the sagittal plane.

30. The system of claim 29, wherein the first and second bone portions comprise first and second pedicles of a vertebra of the spine, the system further comprising first and second guide wires configured to be driven into the first and second pedicles, wherein each of the first and second anchoring features comprises an opening sized to receive one of the guide wires so that the guide wires are able to guide positioning of the first and second anchoring features on the pedicles.

31. The system of claim 21, wherein each of the first and second anchoring features comprises a pivot feature, wherein the pivot features cooperate to permit rotation of the frame about an axis extending generally parallel to a displacement between the first and second pivot features.

32. The system of claim 22, wherein each of the pivot features comprises a semispherical surface shaped to seat within a correspondingly semispherical interface of each of the first and second pedicles.

33. The system of claim 21, further comprising:
   a left adjacent facet joint replacement prosthesis shaped to replace a left adjacent natural facet of the spine such that the left adjacent facet joint replacement prosthesis is positioned to articulate with the left facet joint replacement prosthesis; and
   a right adjacent facet joint replacement prosthesis shaped to replace a right adjacent natural facet of the spine such that the right adjacent facet joint replacement prosthesis is positioned to articulate with the right facet joint replacement prosthesis.

34. The system of claim 21, further comprising a crosslinking member attachable to the left and right facet joint prostheses to attach the left and right facet joint prostheses together.

* * * * *

UNITED STATES PATENT AND TRADEMARK OFFICE
CERTIFICATE OF CORRECTION

| | | |
|---|---|---|
| PATENT NO. | : 7,507,242 B2 | Page 1 of 4 |
| APPLICATION NO. | : 10/990191 | |
| DATED | : March 24, 2009 | |
| INVENTOR(S) | : Daniel J. Triplett et al. | |

It is certified that error appears in the above-identified patent and that said Letters Patent is hereby corrected as shown below:

Column 1, Line 8 insert --Applicants' Docket No. FSI-02 NPROV,-- after "10/860,778,"; Line 12 insert --Applicants' Docket No. FSI-03 NPROV,-- after "10/860,543,"; Line 16 insert --Applicants' Docket No. FSI-04,-- after "10/860,495,"; Line 19 insert --Applicants' Docket No. FSI-05,-- after "10/860,487,".

Column 6, Line 44, "60;" should be changed to --60,--.

Column 7, Line 6 insert --, Fig. 1,-- after "62", and --, Fig. 1,-- after "26,"; Line 41, "though" should be changed to --through--; Line 45, what reads "an (not shown)" should read --an axis (not shown)--; Line 66 insert --, Fig. 1 ,-- after "10".

Column 8, Line 2 insert --, Fig. 1,-- after "22"; Line 3 insert --, as in Fig. 1-- after "24".

Column 10, Line 31 insert --, as in Fig. 1-- after "24".

Column 11, Line 37 insert --, as in Fig. 1-- after "24"; Line 38 insert --, as in Fig. 4-- after "144"; Line 49 insert --, as in Fig. 4,-- after "224"; Line 50 insert --, as in Fig. 4,-- after "226"; Line 52 insert --, as in Fig. 4,-- after "204"; Line 67 insert --, as in Fig. 4,-- after "118".

Column 12, Line 6 insert --, as in Fig. 4,-- after "110"; Line 12 insert --, as in Fig. 4,-- after "110"; Line 23 insert --, Fig. 4-- after "110"; Line 48, "prevents" should be changed to --prevent--.

Column 13, Line 49 insert --, as in Fig. 4-- after "116"; Line 50 insert --, as in Fig. 4,-- after "116"; Line 53 insert --, Fig. 4,-- after "136"; Line 55 insert --, as in Fig. 4,-- after "136"; Line 57 insert --, Fig. 4,-- after "116"; Line 61 insert --, as in Fig. 5,-- after "110".

Column 14, Line 5 insert --, as in Fig. 5-- after "110"; Line 35 insert --, as in Fig. 5,-- after "110".

Signed and Sealed this
Thirteenth Day of March, 2012

David J. Kappos
*Director of the United States Patent and Trademark Office*

Column 15, Line 17 insert --, Fig. 8,-- after "380" and insert --, Fig. 8-- after "374"; Line 18 insert --, Fig. 8,-- after "366"; Line 20 insert --, Fig. 8,-- after "380"; Line 43 insert --, Fig. 8,-- after "380"; Line 44 insert --, Fig. 8,-- after "380"; Line 46 insert --, Fig. 8,-- after "374"; Line 51 insert --, Fig. 8-- after "374"; Line 56 insert --, Fig. 5,-- after "110"; Line 59 insert --, Fig. 1-- after "26"; Line 65 insert --, as in Fig. 9-- after "330".

Column 16, Line 8 insert --476-- after "second slider"; Line 21 insert --476-- after "slider"; Line 23, "434" should be changed to --476--; Line 16 insert --, as in Fig. 1,-- after "26".

Column 17, Line 13 insert --, Fig. 10,-- after "440"; Line 16 insert --, Fig. 10,-- after "440"; Line 26 insert --, Fig. 11 ,-- after "500"; Line 27 insert --, Fig. 11-- after "494"; Line 29 insert --, Fig. 11,-- after "500"; Line 47 insert --, as in Fig. 1-- after "24"; Line 50 insert --, Fig. 1,-- after "10"; Line 55 insert --, as in Fig. 1,-- after "24"; Line 58 insert --, as in Fig. 1-- after "24".

Column 18, Line 10 insert --, Fig. 1-- after "24"; Line 57, "534" should be changed to --574--; Line 58, "534" should be changed to --574--.

Column 19, Line 22 insert --, as in Fig. 13-- after "520"; Line 27 insert --, as in Fig. 13-- after "526"; Line 38 insert --, as in Fig. 13,-- after "512"; Line 39 insert --, as in Fig. 1-- after "24"; Line 49 insert --, Fig. 13,-- after "512"; Line 50 insert --, Fig. 13,-- after "538"; Line 65 insert --, as in Fig. 13-- after "526".

Column 20, Line 4 insert --, Fig. 14,-- after "536"; Line 12 insert --, as in Fig. 13,-- after "514"; Line 23 insert --, Fig. 13-- after "516"; Line 29 insert --, Fig. 13-- after "516"; Line 34 insert --, as in Fig. 1-- after "24"; Line 38 insert --, as in Fig. 7,-- after "330"; Line 39 insert --, as in Fig. 10-- after "430"; Line 44 insert --of Fig. 5-- after "110"; Line 46 insert --, Fig. 5,-- after "110"; Line 49 insert --of Fig. 13-- after "516"; Line 52 insert --, Fig. 13,-- after "568"; Line 58 insert --as in Fig. 1-- after "26"; Line 61 insert --, Fig. 1-- after "10".

Column 21, Line 11 insert --, as in Figs. 4 and 5,-- after "110"; Line 21 insert --, Fig. 1,-- after "26"; Line 26 insert --, Fig. 1,-- after "26"; Line 40 insert --, as in Fig. 1-- after "24"; Line 45 insert --, as in Figs. 7 and 8,-- after "330"; Line 46 insert --, as in Figs. 10 and 11-- after "430"; Line 59, following "The first pair of apertures", "742" should be changed to --740--.

Column 23, Line 24 insert --, as in Fig. 1-- after "26".

Column 24, Line 10 insert --, as in Fig. 1-- after "respectively"; Line 13 insert --, Fig. 1-- after "10"; Line 16 insert --, Fig. 1-- after "10"; Line 25 insert --, Fig. 1-- after "24"; Line 28 insert --, Fig. 1-- after "30"; Line 35 insert --, not visible in Fig. 18,-- after "712"; Line 39 insert --, Fig. 1-- after "50"; Line 48 insert --, Fig. 1-- after "26"; Line 58 insert --, Fig. 1-- after "14"; Line 67 insert --, Fig. 1-- after "20".

CERTIFICATE OF CORRECTION (continued)

U.S. Pat. No. 7,507,242 B2

Column 25, Line 11 insert --, Fig. 1-- after "18"; Line 16 insert --, Fig. 1-- after "respectively"; Line 18 insert --, Fig. 1,-- after "20"; Line 21 insert --, Fig. 1-- after "22"; Line 28 insert --, Fig. 1-- after "24"; Line 34 insert --, as in Fig. 1-- after "26"; Line 37 insert --, Fig. 1,-- after "26"; Line 40 insert --, Fig. 1-- after "60"; Line 44, "16" should be changed to --17--; Line 49 insert --, Fig. 1-- after "26"; Line 60 insert --, Fig. 1,-- after "26".

Column 26, Line 33 insert --, Fig. 1-- after "26"; Line 43 insert --, Fig. 1,-- after "26".

Column 27, Line 6 insert --, Fig. 1-- after "10"; Line 10 insert --, Fig. 1-- after "26"; Line 17 insert --, as in Fig. 1,-- after "26"; Line 23 insert --, Fig. 1,-- after "26"; Line 24 insert --, Fig. 1,-- after "64"; Line 63 insert --, not shown in Fig. 21,-- after "668".

Column 28, Line 48 insert --, not shown in Fig. 22-- after "430".

Column 29, Line 41 insert --, shown in Fig. 1,-- after "22"; Line 51 insert --, shown in Fig. 22,-- after "42"; Line 63 insert --, Fig. 22,-- after "64".

Column 30, Line 15 insert --, Fig. 22-- after "24"; Line 21 insert --, Fig. 20,-- after "64" and insert --, Fig. 22,-- after "60"; Line 36 insert --, not shown in Fig. 24-- after "110"; Line 45 insert --(not visible)-- after "88"; Line 55 insert --(not visible)-- after "90"; Line 66 insert --, Fig. 25,-- after "42".

Column 31, Line 26 insert --, Fig. 27-- after "42"; Line 35, "11" should be changed to --110, as in Fig. 29,--; Line 40 insert --As in Fig. 29-- before "The frame 110"; Line 41 insert --, Fig. 4,-- after "144"; Line 44 insert --, as in Figs. 4 and 5,-- after "210"; Line 53 insert --, Fig. 4,-- after "122"; Line 54 insert --, Fig. 28,-- after "920"; Line 55 insert --, Fig. 4,-- after "128" and insert --, Fig. 28,-- after "920"; Line 63 insert --, Fig. 28-- after "850"; Line 64 insert --, Fig. 6,-- after "260"; Line 65 insert --, Fig. 4-- after "110".

Column 32, Line 2 insert --, Fig. 6,-- after "260"; Line 9 insert --, Fig. 6,-- after "264"; Line 11 insert --, Fig. 4,-- after "116"; Line 14 insert --, Fig. 6-- after "280"; Line 17 insert --, Fig. 4-- after "116"; Line 19 insert --, as in Fig. 29,-- after "110"; Line 51 insert --, Fig. 27,-- after "60"; Line 53 insert --, Fig. 27,-- after "38"; Line 55 insert --, as in Fig. 7,-- after "330".

Column 33, Line 3 insert --, as in Fig. 7-- after "374"; Line 5 insert --, as in Fig. 1,-- after "24"; Line 8 insert --, Fig. 31,-- after "26"; Line 14 insert --, Fig. 28,-- after "26"; Line 16 insert --, Fig. 28,-- after "24"; Line 21 insert --, not shown in Fig. 32,-- after "430"; Line 24 insert --, Fig. 27,-- after "24"; Line 26 insert --, not shown in Fig. 32,-- after "348"; Line 28 insert --, Fig. 10,-- after "440"; Line 45 insert --, Fig. 33,-- after "26"; Line 46 insert --, Fig. 33,-- after "110"; Line 51 insert --, Fig. 33,-- after "62".

Column 34, Line 5 insert --, Fig. 22-- after "862"; Line 22 insert --42-- after "points", and "42" should be changed to --24--; Line 23 insert --72-- after "70,"; Line 39 insert --, Fig. 3,-- after "92"; Line 41 insert --, not visible in Fig. 36,--after "90; Line 54 insert --, as in Fig. 3,-- after "102"; Line 55 insert --, Fig. 36,-- after "926"; Line 56 insert --, Fig. 3,-- after "100"; Line 60, "The" should be changed to --the--.

Column 35, Line 19 insert --, not shown in Fig. 38-- after "668"; Line 40 insert --, not visible in Fig.

CERTIFICATE OF CORRECTION (continued)
U.S. Pat. No. 7,507,242 B2

38,-- after "790"; Line 48 insert --, Fig. 17,-- after "660"; Line 58 insert --, as in Fig. 17,-- after "806".

Column 36, Line 3 insert --, as in Fig. 17,-- after "806"; Line 15 insert --, not visible in Fig. 40-- after "110" and insert --, not visible in Fig. 40,-- after "260"; Line 20 insert --, as in Fig. 17,-- after "714"; Line 40 insert --, not shown in Fig. 40-- after "tools"; Line 42 insert --, Fig. 16,-- after "630"; Line 45 insert --, not shown in Fig. 40-- after "110"; Line 46 insert --, as in Fig. 13-- after "516"; Line 58 insert --, not visible in Fig. 41,-- after "38"; Line 61 insert --, not visible in Fig. 41,-- after "650".

Column 37, Line 3 insert --, not visible in Fig. 41,-- after "600"; Line 19 insert --, not shown in Fig. 41,-- after "512"; Line 36 insert --, not visible in Fig. 42-- after "670"; Line 43 insert --, not shown-- after "516"; Line 62 insert --, not visible in Fig. 43,-- after "518".

Column 38, Line 3 insert --580-- after "shaft"; Line 14 insert --(not visible)-- after "670"; Line 21 insert --, as in Fig. 43-- after "920"; Line 25 insert --, Fig. 1,-- after "24"; Line 53 insert --(not visible)-- after "790"; Line 56 insert --(not visible)-- after "792"; Line 67 insert --, not shown in Fig. 45-- after "672".